US012180298B2

(12) United States Patent
van Schooten et al.

(10) Patent No.: US 12,180,298 B2
(45) Date of Patent: Dec. 31, 2024

(54) HEAVY CHAIN ANTIBODIES BINDING TO PSMA

(71) Applicant: TENEOBIO, INC., Newark, CA (US)

(72) Inventors: Wim van Schooten, Newark, CA (US); Starlynn Clarke, Newark, CA (US); Kevin Dang, Newark, CA (US); Ben Buelow, Newark, CA (US)

(73) Assignee: TENEOBIO, INC., Thousand Oaks, CA (US)

( * ) Notice: Subject to any disclaimer, the term of this patent is extended or adjusted under 35 U.S.C. 154(b) by 588 days.

(21) Appl. No.: 17/601,417

(22) PCT Filed: Apr. 3, 2020

(86) PCT No.: PCT/US2020/026686
§ 371 (c)(1),
(2) Date: Oct. 4, 2021

(87) PCT Pub. No.: WO2020/206330
PCT Pub. Date: Oct. 8, 2020

(65) Prior Publication Data
US 2022/0195068 A1 Jun. 23, 2022

Related U.S. Application Data

(60) Provisional application No. 62/830,130, filed on Apr. 5, 2019.

(51) Int. Cl.
*C07K 16/30* (2006.01)
*A61P 35/00* (2006.01)
*C07K 16/28* (2006.01)
*A61K 39/00* (2006.01)

(52) U.S. Cl.
CPC .......... *C07K 16/3069* (2013.01); *A61P 35/00* (2018.01); *C07K 16/2809* (2013.01); *A61K 2039/505* (2013.01); *C07K 2317/24* (2013.01); *C07K 2317/31* (2013.01); *C07K 2317/33* (2013.01); *C07K 2317/565* (2013.01); *C07K 2317/569* (2013.01); *C07K 2317/60* (2013.01); *C07K 2317/92* (2013.01)

(58) Field of Classification Search
CPC .......... C07K 16/3069; C07K 2317/569; C07K 16/2809; C07K 2317/31
USPC ............................................ 424/133.1, 136.1
See application file for complete search history.

(56) References Cited

U.S. PATENT DOCUMENTS

| 4,816,567 A | 3/1989 | Cabilly et al. |
| 5,500,362 A | 3/1996 | Robinson et al. |
| 5,585,097 A | 12/1996 | Bolt et al. |
| 5,821,337 A | 10/1998 | Carter et al. |
| 5,929,212 A | 7/1999 | Jolliffe et al. |
| 5,968,509 A | 10/1999 | Gorman et al. |
| 6,706,265 B1 | 3/2004 | Bolt et al. |
| 6,750,325 B1 | 6/2004 | Jolliffe et al. |
| 7,262,276 B2 | 8/2007 | Huang et al. |
| 7,381,803 B1 | 6/2008 | Weiner et al. |
| 7,541,513 B2 | 6/2009 | Bruggeman et al. |
| 7,635,472 B2 | 12/2009 | Kufer et al. |
| 7,728,114 B2 | 6/2010 | Mach et al. |
| 7,862,813 B2 | 1/2011 | Bjork, Jr. |
| 8,236,308 B2 | 8/2012 | Kischel et al. |
| 8,367,888 B2 | 2/2013 | Brüggemann et al. |
| 8,883,150 B2 | 11/2014 | Craig et al. |
| 9,034,324 B2 | 5/2015 | Kalled et al. |
| 9,150,664 B2 | 10/2015 | Kufer et al. |
| 9,340,621 B2 | 5/2016 | Kufer et al. |
| 9,365,655 B2 | 6/2016 | Craig et al. |
| 10,934,363 B2 | 3/2021 | Fan et al. |
| 11,186,639 B2 * | 11/2021 | Harris ................ C07K 16/3069 |
| 11,390,681 B2 * | 7/2022 | Harris ................ C07K 16/2878 |
| 11,434,299 B2 | 9/2022 | Force Aldred et al. |
| 11,505,606 B2 | 11/2022 | Trinklein et al. |
| 11,613,572 B2 | 3/2023 | Trinklein et al. |
| 2004/0229310 A1 | 11/2004 | Simmons |
| 2005/0048572 A1 | 3/2005 | Reilly et al. |
| 2007/0065437 A1 | 3/2007 | Elson et al. |
| 2007/0071675 A1 | 3/2007 | Wu et al. |
| 2007/0212733 A1 | 9/2007 | Martin |
| 2009/0098134 A1 | 4/2009 | Buelow |
| 2010/0122358 A1 | 5/2010 | Brüggemann et al. |
| 2013/0156769 A1 | 6/2013 | Kufer et al. |
| 2013/0273055 A1 | 10/2013 | Borges et al. |
| 2013/0273066 A1 | 10/2013 | Gokarn et al. |
| 2014/0056897 A1 | 2/2014 | Buelow et al. |
| 2014/0088295 A1 | 3/2014 | Smith et al. |

(Continued)

FOREIGN PATENT DOCUMENTS

| CN | 105968203 A | 9/2016 |
| CN | 105968204 A | 9/2016 |

(Continued)

OTHER PUBLICATIONS

U.S. Appl. No. 18/393,099, filed Oct. 20, 2022, Harris; Katherine.*
ClinicalTrials.gov Identifier: NCT04740034 for Amgen's drug AMG 340; pp. 1-7; Apr. 15, 2024.*
ClinicalTrials.gov Identifier: NCT05646550 for University Hospital Tuebingen's drug CC-1; pp. 1-9; Apr. 15, 2024.*
ClinicalTrials.gov Identifier: NCT04104607 for University Hospital Tuebingen's drug CC-1, PSMAxCD3; pp. 1-9; Apr. 15, 2024.*
"OMT Therapeutics Announces UniRat™ Alliance with Caltech," Business Wire (May 15, 2015, 1:00 AM EDT), http://www.businesswire.com/news/home/20150514006523/en/OMT-Therapeutics-Announces-UniRat(TM)-Alliance-Caltech.

(Continued)

*Primary Examiner* — Lynn A Bristol
(74) *Attorney, Agent, or Firm* — Amy C. Madl

(57) ABSTRACT

Anti-PSMA heavy chain antibodies are disclosed, along with methods of making such antibodies, compositions, including pharmaceutical compositions, comprising such antibodies, and their use to treat disorders that are characterized by the expression of PSMA.

28 Claims, 13 Drawing Sheets
Specification includes a Sequence Listing.

(56) References Cited

U.S. PATENT DOCUMENTS

| | | | |
|---|---|---|---|
| 2015/0118251 A1 | 4/2015 | Deslandes et al. | |
| 2015/0266966 A1 | 9/2015 | Smith et al. | |
| 2015/0337054 A1 | 11/2015 | Gardner et al. | |
| 2015/0368351 A1 | 12/2015 | Vu et al. | |
| 2015/0376287 A1 | 12/2015 | Vu et al. | |
| 2016/0046724 A1 | 2/2016 | Brogdon et al. | |
| 2016/0159894 A1 | 6/2016 | Hartmann et al. | |
| 2016/0166689 A1 | 6/2016 | Adler et al. | |
| 2016/0194399 A1 | 7/2016 | Irving et al. | |
| 2016/0355591 A1 | 12/2016 | Goldenberg et al. | |
| 2017/0051068 A1 | 2/2017 | Pillarisetti et al. | |
| 2017/0174770 A1 | 6/2017 | Bruggemann et al. | |
| 2017/0275363 A1 | 9/2017 | Chang et al. | |
| 2019/0106504 A1 | 4/2019 | Wu et al. | |
| 2019/0225671 A1 | 7/2019 | van Schooten et al. | |
| 2020/0085839 A1 | 3/2020 | Sidransky et al. | |
| 2020/0138865 A1 | 5/2020 | Kochenderfer et al. | |
| 2020/0157232 A1 | 5/2020 | Trinklein et al. | |
| 2020/0339685 A1 | 10/2020 | Schellenberger et al. | |
| 2021/0047402 A1 | 2/2021 | Trinklein et al. | |
| 2021/0095022 A1 | 4/2021 | Force Aldred et al. | |
| 2021/0147564 A1 | 5/2021 | Trinklein et al. | |
| 2021/0332133 A1 | 10/2021 | Force Aldred et al. | |
| 2021/0340255 A1 | 11/2021 | Harris et al. | |
| 2021/0355215 A1 | 11/2021 | Jorgensen et al. | |
| 2021/0388106 A1 | 12/2021 | van Schooten et al. | |
| 2021/0403587 A1 | 12/2021 | Buelow et al. | |
| 2022/0025047 A1 | 1/2022 | Trinklein et al. | |
| 2022/0089729 A1 | 3/2022 | Harris et al. | |
| 2022/0332820 A1* | 10/2022 | Harris | A61P 35/00 |
| 2023/0045100 A1 | 2/2023 | Force Aldred et al. | |
| 2023/0203161 A1* | 6/2023 | Harris | C07K 16/2818 |
| | | | 424/133.1 |
| 2023/0242668 A1 | 8/2023 | Van Schooten | |
| 2023/0265218 A1* | 8/2023 | Desjarlais | C07K 16/468 |
| | | | 530/387.3 |
| 2023/0322961 A1* | 10/2023 | Desjarlais | C07K 16/468 |
| | | | 530/387.3 |

FOREIGN PATENT DOCUMENTS

| | | |
|---|---|---|
| EP | 2762496 A1 | 8/2014 |
| WO | 1996/027011 A1 | 9/1996 |
| WO | 1996/032478 A1 | 10/1996 |
| WO | 1997/034631 A1 | 9/1997 |
| WO | 1998/050431 A2 | 11/1998 |
| WO | 2000/040716 A2 | 7/2000 |
| WO | 2001/012812 A2 | 2/2001 |
| WO | 2001/024811 A1 | 4/2001 |
| WO | 2001/024812 A1 | 4/2001 |
| WO | 2001/077342 A1 | 10/2001 |
| WO | 2001/087977 A2 | 11/2001 |
| WO | 2002/066516 A2 | 8/2002 |
| WO | 2004/106383 A1 | 12/2004 |
| WO | 2005/040220 A1 | 5/2005 |
| WO | 2005/058815 A2 | 6/2005 |
| WO | 2005/061547 A2 | 7/2005 |
| WO | 2006/008548 A2 | 1/2006 |
| WO | 2006/089232 A2 | 8/2006 |
| WO | 2007/042261 A2 | 4/2007 |
| WO | 2007/066109 A1 | 6/2007 |
| WO | 2007/117600 A2 | 10/2007 |
| WO | 2008/119565 A2 | 10/2008 |
| WO | 2008/119566 A2 | 10/2008 |
| WO | 2008/119567 A2 | 10/2008 |
| WO | 2009/132058 A2 | 10/2009 |
| WO | 2010/032061 A1 | 3/2010 |
| WO | 2010/037835 A2 | 4/2010 |
| WO | 2010/037836 A2 | 4/2010 |
| WO | 2010/037837 A2 | 4/2010 |
| WO | 2010/037838 A2 | 4/2010 |
| WO | 2010/104949 A2 | 9/2010 |
| WO | 2010/109165 A2 | 9/2010 |
| WO | 2011/097603 A1 | 8/2011 |
| WO | 2011/121110 A1 | 10/2011 |
| WO | 2012/066058 A1 | 5/2012 |
| WO | 2012/122512 A1 | 9/2012 |
| WO | 2012/122528 A1 | 9/2012 |
| WO | 2012/143498 A1 | 10/2012 |
| WO | 2012/145714 A2 | 10/2012 |
| WO | 2012/163805 A1 | 12/2012 |
| WO | 2013/072406 A1 | 5/2013 |
| WO | 2013/072415 A1 | 5/2013 |
| WO | 2013/158856 A2 | 10/2013 |
| WO | 2014/022540 A1 | 2/2014 |
| WO | 2014/047231 A1 | 3/2014 |
| WO | 2014/068079 A1 | 5/2014 |
| WO | 2014/089335 A2 | 6/2014 |
| WO | 2014/093908 A2 | 6/2014 |
| WO | 2014/122144 A1 | 8/2014 |
| WO | 2014/140248 A1 | 9/2014 |
| WO | 2014/141192 A1 | 9/2014 |
| WO | 2015/095412 A1 | 6/2015 |
| WO | 2015/121383 A1 | 8/2015 |
| WO | 2015/149077 A1 | 10/2015 |
| WO | 2016/014974 A2 | 1/2016 |
| WO | 2016/062990 A1 | 4/2016 |
| WO | 2016/079081 A1 | 5/2016 |
| WO | 2016/079177 A1 | 5/2016 |
| WO | 2016/094304 A2 | 6/2016 |
| WO | 2016/113555 A1 | 7/2016 |
| WO | 2016/187546 A1 | 11/2016 |
| WO | 2016/187594 A1 | 11/2016 |
| WO | 2017/023761 A1 | 2/2017 |
| WO | 2017/025038 A1 | 2/2017 |
| WO | 2017/031104 A1 | 2/2017 |
| WO | 2015/063339 A1 | 5/2017 |
| WO | 2017/081211 A2 | 5/2017 |
| WO | 2017/122018 A1 | 7/2017 |
| WO | 2017/122019 A1 | 7/2017 |
| WO | 2017/134134 A1 | 8/2017 |
| WO | 2017/223111 A1 | 12/2017 |
| WO | 2018/039180 A1 | 3/2018 |
| WO | 2018/052503 A1 | 3/2018 |
| WO | 2018098354 A1 | 5/2018 |
| WO | 2018/119215 A1 | 6/2018 |
| WO | 2018/237006 A1 | 12/2018 |
| WO | 2018/237037 A2 | 12/2018 |
| WO | 2019/000223 A1 | 1/2019 |
| WO | 2019/006072 A1 | 1/2019 |
| WO | 2019/012260 A1 | 1/2019 |
| WO | 2019/055689 A1 | 3/2019 |
| WO | 2019/075413 A1 | 4/2019 |
| WO | 2019/126756 A1 | 6/2019 |
| WO | 2019/133761 A1 | 7/2019 |
| WO | 2020/018922 A1 | 1/2020 |
| WO | 2020/061478 A2 | 3/2020 |
| WO | 2020/087065 A1 | 4/2020 |
| WO | 2020/252366 A1 | 12/2020 |
| WO | 2021/127489 A1 | 6/2021 |
| WO | 2021/222578 A1 | 11/2021 |
| WO | 2021/222616 A1 | 11/2021 |
| WO | 2021/228783 A1 | 11/2021 |
| WO | 2022/006316 A1 | 1/2022 |
| WO | 2022/109010 A1 | 5/2022 |
| WO | 2022/183074 A2 | 9/2022 |
| WO | 2022/183101 A1 | 9/2022 |
| WO | 2022/212848 A1 | 10/2022 |
| WO | 2022/216864 A1 | 10/2022 |
| WO | 2022/221698 A1 | 10/2022 |
| WO | WO 2023086336 * | 11/2022 |
| WO | 2022/271987 A1 | 12/2022 |
| WO | 2023/004197 A1 | 1/2023 |
| WO | WO 2023164510 * | 2/2023 |
| WO | WO 2023193015 * | 3/2023 |

OTHER PUBLICATIONS

"Teneobio Announces US FDA Approval of the Investigational New Drug Application for TNB-383B and the Initiation of Phase I Clinical Studies in Multiple Myeloma Patients," Global Newswire (Apr. 29, 2019, 8:00 ET), https://www.globenewswire.com/news-

(56) References Cited

OTHER PUBLICATIONS release/2019/04/29/1811199/0/en/Teneobio-Announces-US-FDA-Approval-of-the-Investigational-New-Drug-Application-for-TNB-383B-and-the-Initiation-of-Phase-I-Clinical-Studies-in-Multiple-Myeloma-Patients.html.

Adams et al., "Prolonged in Vivo Tumour Retention of a Human Diabody Targeting the Extracellular Domain of Human HER2/neu," (1998) British Journal of Cancer 77(9):1405-1412.

Alderson et al., "CAT-8015: A Second-Generation Pseudomonas Exotoxin A-Based Immunotherapy Targeting CD22-Expressing Hematologic Malignancies," (2009) Clinical Cancer Research 15(3):832-839.

Ali et al., "T cells expressing an anti-B-cell maturation antigen chimeric antigen receptor cause remissions of multiple myeloma," (2016) Blood 128(13):1688-1700.

Almagro, "Identification of differences in the specificity-determining residues of antibodies that recognize antigens of different size: implications for the rational design of antibody repertoires," (2004) Journal of Molecular Recognition 17(2):132-143.

Amiri et al., "A Novel Anti-CD22 scFv-apoptin Fusion Protein Induces Apoptosis in Malignant B-cells," (2017) AMB Express 7:112, 11 pages.

Anonymous, "A Study of TNB-383B in Subjects with Relapsed or Refractory Multiple Myeloma," (2019), Retrieved from the Internet on May 1, 2019, from <https://clinicaltrials.gov/ct2/show/NCT03933735>, 4 pages.

Anonymous, "Antibody Therapeutics—TeneoBio's Next Generation of Multispecific Antibody Therapeutics," (2018), Retrieved from the Internet: <https://drug-dev.com/antibody-therapeutics-teneobios-next-generation-of-multispecific-antibody-therapeutics/>.

Anonymous, "Flow Cytometry Antibody: CD3e Cat. No. CT026-R301, SinoBiological Inc,—Antibody-Catalogue," (2017) Sinobiological, Inc., Retrieved from the Internet: <https://www.sinobiological.com/antibodies/human-cynomolgus-cd3d-cd3e-ct026-r301>.

Armour et al., "Recombinant human IgG molecules lacking Fcγ receptor I binding and monocyte triggering activities," (1999) Eur J Immunol. 29(8):2613-2624.

Arnett et al., "Crystal Structure of a Human CD3-epsilon/delta Dimer in Complex with a UCHT1 Single-chain Antibody Fragment," (2004) Proc Natl Acad Sci USA 101(46):16268-16273.

Baas et al., "Superhuman Mice," (2014) Science-Business exchange 7(17):1-2.

Baeuerle et al., "Bispecific T-cell engaging antibodies for cancer therapy," (2009) Cancer Research 69(12):4941-4944.

Baeuerle et al., "BiTE: A new class of antibodies that recruit T-cells," (2008) Drugs of the Future 33(2):137-147.

Baeuerle et al., "BiTE: Teaching antibodies to engage T-cells for cancer therapy," (2009) Current Opinion in Molecular Therapeutics 11(1):22-30.

Bargou et al., "Tumor Regression in Cancer Patients by Very Low Doses of a T Cell-Engaging Antibody," (2008) Science 321:974-977.

BCMA (Vicky-1): ALX-804-151 product datasheet, Enzo Life Sciences, last revised Dec. 20, 2019.

BCMA (Vicky-1): sc-57037 datasheet, Santa Cruz Biotechnology, https://datasheets.scbt.com/sc-57037.pdf (last visited Apr. 12, 2022).

Bellucci et al., "Complete response to donor lymphocyte infusion in multiple myeloma is associated with antibody responses to highly expressed antigens," (2004) Blood 103(2):656-663.

Bellucci et al., "Complete response to donor lymphocyte infusion in patients with multiple myeloma is associated with antibody response to BCMA, a plasma cell membrane receptor," (2003) Blood 102(11):192a-193a.

Bellucci et al., "Graft-versus-tumor response in patients with multiple myeloma is associated with antibody response to BCMA, a plasma-cell membrane receptor," (2005) Blood 105(10):3945-3950.

Bluemel et al., "Epitope Distance to the Target Cell Membrane and Antigen Size Determine the Potency of T Cell-mediated Lysis by BiTE Antibodies Specific for a Large Melanoma Surface Antigen," (2010) Cancer Immunol Immunother 59(8):1197-1209.

Bodmer et al., "The molecular architecture of the TNF superfamily," (2002) Trends in Biochemical Sciences 27(1):19-26.

Boesch et al., "Highly parallel characterization of IgG Fc binding interactions," (2014) mAbs 6(4):915-927.

Borchmann et al., "Phase 1 trial of the Novel Bispecific Molecule H22xKi-4 in Patients with Refractory Hodgkin Lymphoma," (2002) Blood 100(9):3101-3107.

Bossen et al., "BAFF, APRIL and their receptors: Structure, function and signaling," (2006) Seminars in Immunology 18:263-275.

Brüggemann et al., "Heavy-Chain-Only Antibody Expression and B-Cell Development in the Mouse," (2006) Crit. Rev. Immunol. 26(5):377-390.

Brüggemann et al., "Human Antibody Production in Transgenic Animals," (2015) Archivum Immunologiae et Therapiae Experimentalis 63(2):101-108.

Buelow et al., "Development of a Fully Human T Cell Engaging Bispecific Antibody for the Treatment of Multiple Myeloma," (2017), Retrieved from the Internet: <http://www.teneobio.com/wp-content/uploads/2018/01/Poster_1.pdf> [Inactive Link].

Buelow et al., "Effect of modulation of CD3 binding in a PSMAxCD3 T-cell engaging bispecific antibody on maintenance of efficient tumor cell kill cytokine release," (2020) J. Clin. Oncol. 38(15):Suppl. e17583, DOI: 10.1200/JCO.2020.38.15_suppl.e17583.

Buelow et al., "Evaluation of monovalent versus biparatopic CD3xPSMA bispecific antibodies for tcell mediated killing of prostate tumor cells with minimal cytokine release," (2019) J. Clin. Oncol. 37(15);Suppl.e16519. DOI: 10.1200/JCO.2019.37.15_suppl.e16519.

Buelow et al., "TNB585.001: A multicenter, phase 1, open-label, dose-escalation and expansion study of TNB-585, a bispecific T-cell engager targeting PSMA in subjects with metastatic castrate resistant prostate cancer," (2021) J. Clin. Oncol. 39(15): Suppl. TPS5092, DOI: 10.1200/JCO.2021.39.15_suppl.TPS5092.

Buelow et al., "Development of a fully human T cell engaging bispecific antibody for the treatment of multiple myeloma," (2017) J. Clin. Oncol. 35, No. 15_suppl (May 20, 2017) 8017-8017, DOI: 10.1200/JCO.2017.35.15_suppl.8017.

Buelow et al., "TNB3838.0001: A Multicenter, Phase 1, Open-Label, Dose-Escalation and expansion Study of TNB-3838, a Bispecific Antibody Targeting BCMA in Subjects with Relapsed or Refractory Multiple Myeloma," (2019) Blood 134(Supplement 1):1874.

Canfield et al., "The Binding Affinity of Human IgG for its High Affinity Fc Receptor Is Determined by Multiple Amino Acids in the CH2 Domain and Is Modulated by the Hinge Region," (1991) J. Exp. Med. 173(6):1483-1491.

Caraccio et al., "Bispecific Antibodies for Multiple Myeloma: A Review of Targets, Drugs, Clinical Trials and Future Directions," (2020) Frontiers in Immunology 11, Article 501, 25 pages.

Carpenter et al., "B-cell Maturation Antigen Is a Promising Target for Adoptive T-cell Therapy of Multiple Myeloma," (2013) Clin Cancer Res 19(8):2048-2060.

Chames et al., "Bispecific antibodies for cancer therapy," (2009) Current Opinion in Drug Discovery & Development 12(2):276-283.

Chames et al., "Bispecific Antibodies for Cancer Therapy," (2009) mAbs 1(6):539-547.

Chassaing et al., "Dextran Sulfate Sodium (DSS)-Induced Colitis in Mice," (2014) Current Protocols in Immunology 15(25):1-14.

Chatenoud, et al., "CD3 Monoclonal Antibodies: A First Step Towards Operational Immune Tolerance in the Clinic", (2012) The Review of Diabetic Studies, vol. 9, No. 4: 372-381.

Chen et al., "Fusion protein linkers: Property, design and functionality," (2013) Advanced Drug Delivery Reviews 65(10): 1357-1369.

Chini et al., "The Pharmacology of CD38/NADase: An Emerging Target in Cancer and Diseases of Aging," (2018) Trends in Pharmacological Sciences 39(4):424-436.

Choi et al., "Bispecific antibodies engage T cells for antitumor immunotherapy," (2011) Expert Opinion on Biological Therapy 11(7):843-853.

Chothia et al., "Conformations of immunoglobulin hypervariable regions," (1989) Nature 342:877-883.

(56) References Cited

OTHER PUBLICATIONS

Chothia et al., "Canonical structures for the hypervariable regions of immunoglobulins," (1987) Journal of Molecular Biology 196(4):901-917.
Chou et al., "Quantitative Analysis of Dose-Effect Relationships: The Combined Effects of Multiple Drugs or Enzyme Inhibitors," (1984) Adv Enzyme Regul. 22:27-55.
Clarke et al., "A novel CD3xPSMA bispecific antibody for efficient T cell mediated killing of prostate tumor cells with minimal cytokine release," (2019) Journal of Clinical Oncology 37, No. 7_suppl, DOI: 10.1200/JCO.2019.37.7_suppl.324.
Clarke et al., "Multispecific antibody development platform based on human heavy chain antibodies." (2019) Frontiers in Immunology 9:3037.
Clayton et al., "CD3η and CD3ζ are alternatively spliced products of a common genetic locus and are transcriptionally and/or post-transcriptionally regulated during T-cell development," (1991) Proceedings of the National Academy of Sciences USA 88:5202-5206.
Clinicaltrials.gov, "A Study of AMG 340 in Subjects with Metatstatic Castrate-Resistant Prostate Carcinoma," (2021) ID: NCT04740034; 8 pages.
Clinicaltrials.gov, "Study of CC-93269, a BCMA x CD3 T Cell Engaging Antibody, In Participants with Relapsed and Refectory Multiple Myeloma", (2022) ID: NCT03486067; 3 pages.
Clynes et al., "Fc Receptors are Required in Passive and Active Immunity to Melanoma," (1998) PNAS (USA) 95(2):652-656.
Concepcion et al., "Label-Free Detection of Biomolecular Interactions Using BioLayer Interferometry for Kinetic Characterization," (2009) Combinatorial Chemistry & High Throughput Screening 12(8):791-800.
Conference abstracts of the International Myeloma Society 19th Annual Meeting and Exposition (2022).
Cui et al., "Targeted Integration in Rat and Mouse Embryos with Zinc-finger Nucleases," (2011) Nature Biotechnology 29(1):64-67.
Dai et al., "Chimeric Antigen Receptors Modified T-Cells for Cancer Therapy," (2016) J Natl Cancer Inst 108(7):dvj439.
Dang et al., "Attenuating CD3 affinity in a PSMAxCD3 bispecific antibody enables killing of prostate tumor cells with reduced cytokine release," (2021) J Immunother Cancer 9:e002488; 14 pages.
DaSilva, "Abstract 34: A Met x MET Bispecific Antibody that Induces Receptor Degradation Potently Inhibits the Growth of MET-addicted Tumor Xenografts," (2017) AACR Annual Meeting 1-2.
Davies et al., "Affinity improvement of single antibody VH domains: residues in all three hypervariable regions affect antigen binding," (1996) Immunotechnology 2(3):169-179.
Declaration of Dr. Rui Zhu, Ph. D., dated Jun. 9, 2020, in EP Opposition No. 2780375 for EP Application No. 12805432.7.
Declaration of Kara Olson, dated May 14, 2021, in EP Opposition No. 2780375 for EP Application No. 12805432.7.
Declaration of Kevin C. Lindquist, dated Jun. 9, 2020, in EP Opposition No. 2780375 for EP Application No. 12805432.7.
Declaration of Nathan D. Trinklein, Ph.D., in EP Opposition No. 2780375 for EP Application No. 12805432.7.
Desmyter et al., "Antigen Specificity and High Affinity Binding Provided by One Single Loop of a Camel Single-Domain Antibody," (2001) Journal of Biological Chemistry 276(28):26285-26290.
DiLillo et al., "A BCMAxCD3 Bispecific T Cell-Engaging Antibody Demonstrates Robust Antitumor Efficacy Similar to that of Anti-BCMA CAR T Cells," (2021) Blood Advances 5(5):1291-1304.
Dillon et al., "An APRIL to remember: Novel TNF ligands as therapeutic targets," (2006) Nat Rev Drug Discov. 5(3):235-246.
Dimopoulos et al., "Daratumumab, Lenalidomide, and Dexamethasone for Multiple Myeloma," (2016) New England Journal of Medicine 375(14):1319-1331.
DiPippo et al., "Efficacy studies of an antibody-drug conjugate PSMA-ADC in patient-derived prostate cancer xenografts," (2015) Prostate 75:303-313, DOI: 10.1002/pros.22916.
Dondelinger et al., "Understanding the Significance and Implications of Antibody Numbering and Antigen-binding Surface/Residue Definition," (2018) Frontiers in Immunology 9:1-15, DOI: 10.3389/fimmu.2018.02278.
Dong et al., "Structural Basis of Assembly of the Human T Cell Receptor—CD3 Complex", (2019) Nature, vol. 573: 546-552.
Dooley et al., "Selection and Characterization of Naturally Occurring Single-domain (IgNAR) Antibody Fragments from Immunized Sharks by Phage Display," (2003) Molecular Immunology 40(1):25-33.
Duncan et al., "Localization of the binding site for the human high-affinity Fc receptor on IgG," (1988) Nature 332:563-564.
Durben et al., "Characterization of a Bispecific FLT3 X CD3 Antibody in an Improved, Recombinant Format for the Treatment of Leukemia," (2015) Molecular Therapy 23(4):648-655.
Excerpt of examination report from EP Application No. 12805432.7, dated Oct. 31, 2016, p. 1.
Faraji et al., "Development and Characterization of a Camelid Single-domain Antibody Directed to Human CD22 Biomarker," (2018) Biotechnology and Applied Biochemistry 65(5):718-725.
Figure 6.8 of Antigen receptor structure and signaling pathways, Immunobiology: The Immune System in Health and Disease. 5th Edition, Janeway CA Jr, Travers P, Walport M, et al., New York: Garland Science; 2001.
Fitzgerald et al., "The Cytokine FactsBook," 2nd ed. (2001) Academic Press, pp. 151-152.
Foote et al., "Antibody Framework Residues Affecting the Conformation of the Hypervariable Loops," (1992) Journal of Molecular Biology 224(2):487-499.
Force Aldred et al., "Winning the Numbers Game: Novel Multispecific Therapeutics from a Divers Collection of Human Domain Antibodies," (2016), Retrieved from the Internet: <https://2019.lakepharma.com/files/symposiums/Winning%20the%20Numbers%20Game%20-%20Novel%20Multi-specific%20Therapeutics%20from%20a%20Diverse%20Collection%20of%20Human%20Domain%20Antibodies%20-%20Shelley%20Force%20Aldred.pdf> [Inactive Link].
Frenken et al., "Isolation of Antigen Specific Llama $V_{HH}$ Antibody Fragments and Their High Level Secretion by *Saccharomyces cerevisiae*," (2000) J. Biotechnol. 78:11-21.
Fry et al., "CD22-targeted CAR T Cells Induce Remission in B-ALL that is Naïve or Resistant to CD19-targeted CAR Immunotherapy," (2018) Nature Medicine 24(1):20-28.
Gazzano-Santoro et al., "A non-radioactive complement-dependent cytotoxicity assay for anti-CD20 monoclonal antibody," (1996) Journal of Immunological Methods 202(2):163-171.
GenBank Accession No. AB052772.1, "*Homo sapiens* gene for BCMA, complete cds," available at https://www.ncbi.nlm.nih.gov/nuccore/AB052772 (last visited Apr. 23, 2020).
GenBank Accession No. NM_000733, "*Homo sapiens* CD3e molecule (CD3E), mRNA," available at https://www.ncbi.nlm.nih.gov/nuccore/NM_000733.3 (last visited Apr. 23, 2020).
Gershoni et al., "Epitope Mapping—The First Step in Developing Epitope-based Vaccines," (2007) Biodrugs, Adis International, Ltd. NZ 21(3):145-156.
Geurts et al., "Knockout Rats via Embryo Microinjection of Zinc-Finger Nucleases," (2009) Science 325(5939):433.
Ghahroudi et al., "Selection and Identification of Single Domain Antibody Fragments from Camel Heavy-chain Antibodies," (1997) FEBS Letters 414(3):521-526.
Giavridis et al., "CAR T cell-induced cytokine release syndrome is mediated by macrophages and abated by IL-1 blockade," (2018) Nature Medicine 24(6):731-738.
Glennie et al., "Preparation and Performance of Bispecific F(ab' gamma)2 Antibody Containing Thioether-linked Fab' gamma Fragments," (1987) Journal of Immunology 139(7):2367-2375.
Goldstein et al., "AMG 701 Induces Cytotoxicity of Multiple Myeloma Cells and Depletes Plasma Cells in Cynomolgus Monkeys," (2020) Blood Advances, vol. 4, No. 17:B1 4180-4194.

(56) References Cited

OTHER PUBLICATIONS

Gras et al., "BCMAp: an integral membrane protein in the Golgi apparatus of human mature B lymphocytes," (1995) Int. Immunol. 7(7):1093-1106.
Gruss et al., "Structural and Biological Features of the TNF Receptor and TNF Ligand Superfamilies: Interactive Signals in the Pathobiology of Hodgkin's Disease," (1996) Ann Oncol, 7 (Suppl 4):S19-S26.
Gust et al., "Endothelial Activation and Blood-Brain Barrier Disruption in Neurotoxicity after Adoptive Immunotherapy with CD19 CAR-T Cells," (2017) Cancer Discovery 7(12):1404-1419.
Guy et al., "Organization of Proximal Signal at the TCR:CD3 Complex," (2009) Immunol Rev 232(1):7-21.
Haffner et al., "Discovery, Synthesis and Biological Evaluation of Thiazoloquin(az)olin(one)es as Potent CD38 Inhibitors," (2015) Journal of Medical Chemistry 58(8):3548-3571.
Hamers-Casterman et al., "Naturally Occurring Antibodies Devoid of Light Chains," (1993) Nature 363:446-448.
Hamilton et al., "Humanization of Yeast to Produce Complex Terminally Sialylated Glycoproteins," (2006) Science 313(5792):1441-1443.
Hagner et al., "Targeting B-Cell Maturation Antigen (BCMA) with CC-93269, a 2+1 T Cell Engager, Elicits Significant Apoptosis in Diffuse Large B-Cell Lymphoma Preclinical Models," (2019) The American Society of Hematology bloodjournal Blood blood, 134(Suppl. 1), 1580.
Hanes et al., "New advances in microsphere-based single-dose vaccines," (1997) Advanced Drug Delivery Reviews 28(1):97-119.
Harris et al., "Lymphoma classification—from controversy to consensus: The R.E.A.L. and WHO Classification of lymphoid neoplasms," Annals of Oncology 11 (Suppl. 1): S3-S10 (2000).
Harris et al., "Sequence-based discovery demonstrates that fixed light chain human transgenic rats produce a diverse repertoire of antigen-specific antibodies," (2018) Frontiers in Immunology 9:889, DOI: 10.3389/fimmu.2018.00889.
Hassani et al., "Construction of a chimeric antigen receptor bearing a nanobody against prostate a specific membrane antigen in prostate cancer," (2019) J Cell Biochem. 120(6):10787-10795.
Hernandez-Hoyos et al., "MOR209/ES414, a Novel Bispecific Antibody Targeting PSMA for the Treatment of Metastatic Castration-Resistant Prostate Cancer," (2016) Mol Cancer Ther 15(9):2155-2165.
Hipp et al., "A novel BCMA/CD3 bispecific T-cell engager for the treatment of multiple myeloma induces selective lysis in vitro and in vivo," (2017) Leukemia 31:1743-1751.
Hlavacek et al., "Steric Effects on Multivalent Ligand-Receptor Binding: Exclusion of Ligand Sites by Bound Cell Surface Receptors," (1999) Biophysical Journal 76(6):3031-3043.
Hofman et al., "[$^{177}$Lu]-PSMA-617 Radionuclide Treatment in Patients with Metastatic Castration-Resistant Prostate Cancer (LuPSMA trial): A Single-Centre Single-Arm, Phase 2 Study," (2018) The Lancet Oncology 19(6):825-833.
Honegger et al., "Yet Another numbering scheme for immunoglobulin variable domains: an automatic modeling and analysis tool," (2001) Journal of Molecular Biology 309(3):657-670.
Hönemann et al., "A Novel Recombinant Bispecific Single-Chain Antibody, bscWue-1 x CD3, Induces T-Cell-Mediated Cytotoxicity Towards Human Multiple Myeloma Cells," (2004) Leukemia 18(3):636-644.
Hötzel et al., "A strategy for risk mitigation of antibodies with fast clearance," (2012) mAbs 4(6):753-760.
Hymowitz et al., "Structures of APRIL-Receptor Complexes," (2005) Journal of Biological Chemistry 280(8):P7218-P7227.
International Search Report for PCT Application No. PCT/US2020/026686, mailed on Jul. 27, 2020.
Iri-Sofla et al., "Nanobody-based chimeric receptor gene integration in Jurkat cells mediated by φC31 integrase," (2011) Experimental Cell Research 317(18):2630-2641.
Jabbour et al., "Monoclonal Antibodies in Acute Lymphoblastic Leukemia," (2015) Blood 125(26):4010-4016.
Jackson et al., "Driving CAR T-cells forward," (2016) Nature Reviews Clinical Oncology 13(6):370-383.
Jamnani et al., "T Cells Expressing VHH-directed Oligoclonal Chimeric HER2 Antigen Receptors: Towards Tumor-Directed Oligoclonal T Cell Therapy," (2014) Biochimica et Biophysica Acta 1840(1):378-386.
Janssens et al., "Generation of Heavy-Chain-Only Antibodies in Mice," (2006) Proceedings of the National Academy of Sciences of the USA 103(41):15130-15135.
Jaton et al., "Recovery of antibody activity on reoxidation of completely reduced polyalanyl heavy chain and its Fd fragment derived from anti-2,4-dinitrophenyl antibody," (1968) Biochemistry 7(12):4185-4195.
Jemal et al., "Cancer Statistics, 2008," (2008) CA Cancer J Clin 58(2):71-96.
Jones, "Analysis of Polypeptides and Proteins," (1993) Advanced Drug Delivery 10(1):29-90.
Kanda et al., "Establishment of a GDP-mannose 4,6-dehydratase (GMD) knockout host cell line: A new strategy for generating completely non-fucosylated recombinant therapeutics," (2007) Journal of Biotechnology 130(3):300-310.
Kaneko et al., "Anti-Inflammatory Activity of Immunoglobulin G Resulting from Fc Sialylation," (2006) Science 313(5787):670-673.
Kapoor et al., "Anti-CD20 Monoclonal Antibody Therapy in Multiple Myeloma," (2008) Br J Haematol 141(2):135-148.
Kim et al., "Mutational approaches to improve the biophysical properties of human single-domain antibodies," (2014) Biochim Biophys Acta 1844(11):1983-2001.
Kjer-Nielsen et al., "Crystal Structure of the Human T Cell Receptor CD3 εγ Heterodimer Complexed to the Therapeutic mAb OKT3," (2004) Proceedings of the National Academy of Sciences 101(20):7675-7680.
Kishimoto et al., "Physical Dissociation of the TCR-CD3 Complex Accompanies Receptor Ligation," (1995) Journal of Experimental Medicine, vol. 182: 1997-B1762006.
Koarada et al., "Autoantibody-Producing RP105(-) B Cells, from Patients with Systematic Lupus Erythematosus, Showed More Preferential Expression of BCMA Compared with BAFF-R than Normal Subjects," (2010) Rheumatology 49(4):662-670.
Köhler et al., "Continuous cultures of fused cells secreting antibody of predefined specificity," (1975) Nature 256:495-497.
Koide et al., "Exploring the capacity of minimalist protein interfaces: interface energetics and affinity maturation to picomolar KD of a single-domain antibody with a flat paratope," (2007) J Mol Biol. 373(4):941-953.
Kontermann, "Bispecific Antibodies," (2011) Springer-Verlag Berlin Heidelberg, Chapters 1, 2, 7, 11, 13, 14, and 15.
Kontermann, "Recombinant bispecific antibodies for cancer therapy," (2005) Acta Pharmacologica Sinica 26(1):1-9.
Kufer et al., "A revival of bispecific antibodies," (2004) Trends in Biotechnology 22(5):238-244.
Kuhns et al., "Deconstructing the Form and Function of the TCR/CD3 Complex," (2006) Immunity 24(2):133-139.
Kumar et al., "Improved survival in multiple myeloma and the impact of novel therapies," (2008) Blood 111(5):2516-2520.
Kumar et al., "International Myeloma Working Group consensus criteria for response and minimal residual disease assessment in multiple myeloma," (2016) The Lancet Oncology 17(8):e328-e346.
Labrijn et al., "Bispecific Antibodies: A Mechanistic Review of the Pipeline," (2019) Nature Reviews Drug Discovery 18(8):585-608.
Langer, "New Methods of Drug Delivery," (1990) Science 249(4976):1527-1533.
Lefranc et al., "The Immunoglobulin FactsBook," (2001).
Lefranc et al., "IMGT, the international ImMunoGeneTics database," (1999) Nucleic Acids Research, 27(1):209-212.
Leiba et al., "Activation of B cell maturation antigen (BCMA) on human multiple myeloma cells by a proliferation-inducing ligand (APRIL) promotes myeloma cell function in the bone marrow microenvironment," (2007) Blood 110(11):1503.
Leow et al., "Single Domain Antibodies as New Biomarker Detectors," (2017) Diagnostics 7(4):52.
Levine, "Mechanisms of Soluble Cytokine Generation," (2004) J Immunol 173(9):5343-5348.

(56) References Cited

OTHER PUBLICATIONS

Lindhofer et al., "Preferential Species-Restricted Heavy/Light Chain Pairing in Rat/Mouse Quadromas. Implications for a Single-Step Purification of Bispecific Antibodies," The Journal of Immunology, 155(1):219-225.
Link et al., "Anti-CD3-Based Bispecific Antibody Designed for Therapy of Human B-Cell Malignancy can Induce T-cell Activation by Antigen-dependent and Antigen-independent Mechanisms," (1998) Int. J. Cancer 77(2):251-256.
Liu et al., "Ligand-receptor binding revealed by the TNF family member TALL-1," (2003) Nature 423:49-56.
Lund et al., "Expression and characterization of truncated forms of humanized L243 IgG1," (2000) European Journal of Biochemistry 267(24):7246-7257.
MAB193 data sheet, Human BCMA/TNFRSF17 Antibody, R&D Systems, last revised Feb. 7, 2018.
Macaque CD3 Epsilon Sequence, "Sequence Alignment Macaque CD3 Epsilon and SEQ ID Nos. 2, 4, 6, and 8 of D14," [online], Retrieved from the Internet: <https://www.uniprot.org/uniprotkb/Q95LI5/entry#sequences>.
Mack et al., "A Small Bispecific Antibody Construct Expressed as a Functional Single-Chain Molecule with High Tumor Cell Cytotoxicity," (1995) PNAS 92(15):7021-7025.
Mailankody et al., "T-Cell Engagers—Modern Immune-Based Therapies for Multiple Myeloma", (2022) The New England Journal of Medicine, vol. 387, No. 6: 558-561.
Mariuzza et al., "The Structural Basis of Antigen-Antibody Recognition," (1987) Ann Ref Biophys Biophys Chem 16:139-159.
Ménoret et al., "Transgenic Animals and Genetic Engineering Techniques," (2015) Transgenic Res 24(6):1079-1085.
Ménoret et al., "Characterization of Immunoglobulin Heavy Chain Knockout Rats," (2010) Eur J Immunol. 40(1):2932-2941.
Merchant et al., "An Efficient Route to Human Bispecific IgG," (1998) Nature Biotechnology, 16(7):677-681.
Mikkilineni et al., "Chimeric antigen receptor T-cell therapies for multiple myeloma," (2017) Blood 130(24):2594-2602, DOI: 10.1182/blood-2017-06-793869.
Miller et al., "Design, Construction, and In Vitro Analyses of Multivalent Antibodies," (2003) Journal of Immunology 170(9):4854-4861.
Moreau et al., "Teclistamab in Relapsed or Refractory Multiple Myeloma", (2022) The New. England Journal of Medicine, vol. 387, No. 6: 495-505.
Moreaux et al., "APRIL and TACI interact with syndecan-1 on the surface of multiple myeloma cells to form an essential survival loop," (2009) Eur J Heamatol 83:119-129.
Müller et al., "Bispecific antibodies for cancer immunotherapy," (2010) Biodrugs 24(2):89-98.
Müller et al., "Recombinant bispecific antibodies for cellular cancer immunotherapy," (2007) Current Opinion in Molecular Therapeutics 9(4):319-326.
Muyldermans, "Single domain camel antibodies: current status," (2001) J Biotechnol 74(4):277-302.
Neisig et al., "Assembly of the T-Cell Antigen Receptor. Participation of the CD3 omega chain," (1993) Journal of Immunology 151:870-879.
Nguyen et al., "Functional Heavy-Chain Antibodies in Camelidae," (2001) Adv Immunol. 79:261-296.
Nguyen et al., "Heavy-chain Only Antibodies Derived from Dromedary are Secreted and Displayed by Mouse B Cells," (2003) Immunology 109(1):93-101.
Nishimoto et al., "Adoptive Therapy with Cord Blood T Regulatory Cells Enhances Anti-myeloma Efficacy of T Cell Based Immunotherapies," (2020) Blood 136(Supp 1): 26-27.
Armitage, Non-Hodgkin's Lymphoma Classification Project, "A clinical evaluation of the International Lymphoma Study Group classification of non-Hodgkin's lymphoma," (1997p) Blood 89(11):3909-3918.

Norelli et al., "Monocyte-derived IL-1 and IL-6 are differentially required for cytokine-release syndrome and neurotoxicity due to CAR T cells," (2018) Nature Medicine 24(6):739-748.
Novak et al., "Expression of BCMA, TACI, and BAFF-R in multiple myeloma: a mechanism for growth and survival," (2004) Blood 103(2):689-694.
Nuttall et al., "Isolation and Characterization of an IgNAR Variable Domain Specific for the Human Mitochondrial Translocase Receptor Tom70," (2003) Eur. J. Biochem. 270:3543-3554.
Nuttall et al., "Selection and Affinity Maturation of IgNAR Variable Domains Targeting Plasmodium falciparum AMA1," (2004) Proteins; Structure, Function and Bioinformatics 55:187-197.
Ofran et al. "Automated identification of complementarity determining regions (CDRs) reveals peculiar characteristics of CDRs and B-cell epitopes," (2008) Journal of Immunology 181(9):6230-6235.
Omniab: Naturally Optimized Human Antibodies (2016), Retrieved from the Internet: <http://content.stockpr.com/omniab/db/252/746/file/OmniAb.pdf>.
Opposition to European Patent No. EP 2780375 B1, Opponent 06: James Poole Limited, Experimental Report 1: Cytotoxic Activity.
Padlan et al., "Identification of specificity-determining residues in antibodies," (1995) FASEB Journal 9(1):133-139.
Palumbo et al., "Daratumumab, Bortezomib, and Dexamethasone for Multiple Myeloma," (2016) New England Journal of Medicine 375(8):754-766.
Panowski et al., "Preclinical efficacy and safety comparison of CD3 bispecific and ADC modalities targeting BCMA for the treatment of multiple myeloma," (2019) Mol Cancer Ther 18(11):2008-2020.
Patel et al., "Engineering an APRIL-specific B Cell Maturation Antigen," (2004) Journal of Biological Chemistry 279(16):16727-16735.
Patentee's Response to EP Communication under Article 94(3), dated May 10, 2017 in EP Application No. 12805432.7.
Patentee's Response to EP Communication under Article 94(3), dated Apr. 13, 2016 in EP Application No. 12805432.7.
Pelekanou et al., "Expression of TNF-superfamily members BAFF and APRIL in Breast Cancer: Immunohistochemical Study in 52 Invasive Ductal Breast Carcinomas," (2008) BMC Cancer 8(76):1-9.
Pessano et al., "The T3/T Cell Receptor Complex: Antigenic Distinction Between the Two 20-kd T3 (Tδ-0 and T3-ε) Subunits," (1985) The EMBO Journal, vol. 4, No. 2: 337-344.
Pick et al., "Daratumumab resistance is frequent in advanced-stage multiple myeloma patients irrespective of CD38 expression and is related to dismal prognosis," (2018) European Journal of Haematology 100(5):494-501.
Plückthun et al., "New protein engineering approaches to multivalent and bispecific antibody fragments," (1997) Immunology 3(2):83-105.
Presta et al., "Generation of Humanized, High Affinity Anti-Tissue Factor Antibody Use as a Novel Antithrombotic Therapeutic," (2001) Thromb Haemost 85:379-389.
Presta et al., "Humanization of an Antibody Directed Against IgE," (1993) Journal of Immunology 151:2623-2632.
Product Summary for Cd3e Monoclonal Antibody (SPV-T3b) [online], Retrieved from the Internet: <https://www.labome.com/product/Invitrogen/07-0303.html>.
Product Summary for Milteniy Biotec CD3 Antibodies Recombinant [online], Retrieved from the Internet: <https://www.miltenyibiotec.com/US-en/products/cd3-antibodies-rea613.html#fitc:1-ml>.
Proprietor's Remarks in Response to Office Action dated Dec. 16, 2014 in U.S. Pat. No. 9,340,621.
Proprietor's Remarks in Response to Office Action dated Jun. 19, 2014 in U.S. Pat. No. 9,150,664.
Pulte et al., "CD39 Expression on T Lymphoctyes Correlates with Severity of Disease in Patients with Chronic Lymphocytic Leukemia," (2011) Clinical Lymphoma, Myeloma & Leukemia 11(4):367-372.
Pulte et al., "Improvement in Survival of Older Adults with Multiple Myeloma: Results of an Updated Period Analysis of SEER Data," (2011) The Oncologist 16(11):1600-1603.
Qin et al., "Paralleled comparison of vectors for the generation of CAR-T cells," (2016) Anti-Cancer Drugs 27(8):711-722.

(56) References Cited

OTHER PUBLICATIONS

Rangaswamy et al., "A Novel T-cell Bispecific Antibody Platform for Efficient T-Cell Mediated Killing of Tumor Cells with Minimal Cytokine Oncology," (2018) Journal of Clinical Oncology No. 5_suppl: 209-209, DOI: 10.1200/JCO.2018.36.5_suppl.209.
Ravetch et al., "Fc Receptors," (1991) Annual Review of Immunology 9:457-492.
Reichert et al., "Development Trends for Monoclonal Antibody Cancer Therapeutics," (2007) Nat Rev Drug Discov 6(5):349-356.
Rennert et al., "A Soluble Form of B Cell Maturation Antigen, a Receptor for the Tumor Necrosis Factor Family Member APRIL, Inhibits Tumor Cell Growth," (2000) J Exp Med. 192(11):1677-1684.
Revets et al., "Nanobodies as novel agents for cancer therapy," (2005) Expert Opin Biol Ther. 5(1):111-124.
Ridgway et al., ""Knobs-into-holes" Engineering of Antibody CH3 Domains for Heavy Chain Heterodimerization, (1996) Protein Engineering 9(7):617-621.
Rodriguez et al., "Initial Results of a Phase I Study of TNB-383B, a BCMA x CD3 Bispecific T-Cell Redirecting Antibody, in Relapsed/Refractory Multiple Myeloma," (2020) Blood 136 (Supp 1):43-44.
Roit, Immunology, translated from English, Moscow: Mir; 2000.
Rossi et al., "Redirected T-cell Killing of Solid Cancers Targeted with an Anti-CD3/Trop-2-Bispecific Antibody is Enhanced in Combination with Interferon-α," (2014) Molecular Cancer Therapeutics 13(10):2341-2351.
Rouet et al., "Fully Human VH Single Domains that Rival the Stability and Cleft Recognition of Camelid Antibodies," (2015) Journal of Biological Chemistry 290(19):11905-11917.
Roux et al., "Comparisons of the Ability of Human IgG3 Hinge Mutants, IgM, IgE, and IgA2, to Form Small Immune Complexes: A Role for Flexibility and Geometry," (1998) Journal of Immunology 161(8):4083-4090.
Ryan et al., "Antibody targeting of B-cell maturation antigen on malignant plasma cells," (2007) Mol Cancer Ther 6(11):3009-3018.
Salmerón et al., "A conformational epitope expressed upon association of CD3-epsilon with either CD3-delta or CD3-gamma is the main target for recognition by anti-CD3 monoclonal antibodies," (1991) J Immunol. 147(9):3047-3052.
Sanchez et al., "Serum B-cell Maturation Antigen Elevated in Multiple Myeloma and Correlates with Disease Status and Survival," (2012) Br J Haematol. 158(6):727-738.
Sanz et al., "B cells as therapeutic targets in SLE" (2010) Nat Rev Rheumatol 6(6):326-337.
Seckinger et al., "Target Expression, Generation, Preclinical Activity, and Pharmacokinetics of the BCMA-T Cell Bispecific Antibody EM801 for Multiple Myeloma Treatment," (2017) Cancer Cell 31(3):396-410.
Serganova et al., "LDH-A Regulates the Tumor Microenvironment via HIF-Signaling and Modulates the Immune Response," (2018) PLoS One 13(9):e0203965, 22 pages.
Shallis et al., "The Multi-Faceted Potential of CD38 Antibody Targeting in Multiple Myeloma," (2017) Cancer Immunol Immunother 66:697-703.
Shields et al., "High Resolution Mapping of the Binding Site on Human IgG1 for FcγRI, FcγRII, FcγRIII, and FcRn and Design of IgG1 Variants with Improved Binding to the FcγR," (2001) J Biol Chem. 276(9):6591-6604.
Shoji-Hosaka et al., "Enhanced Fc-Dependent Cellular Cytotoxicity of Fc Fusion Proteins Derived from TNF Receptor II and LFA-3 by Fucose Removal from Asn-linked Oligosaccharides," (2006) Journal of Biochemistry 140(6):777-783.
Sitia et al., "Developmental Regulation of IgM Secretion: The Role of the Carboxy-Terminal Cysteine," (1990) Cell 60(5):781-790.
Tai et al., "APRIL and BCMA promote human multiple myeloma growth and immunosuppression in the bone marrow microenvironment," (2016) Blood 127(25):3225-3236, DOI: 10.1182/blood-2016-01-691162.
Tai et al., "Novel anti-B-cell maturation antigen antibody-drug conjugate (GSK2857916) selectively induces killing of multiple myeloma," (2014) Blood 123(20):3128-3138.
Tao et al., "Structural features of human immunoglobulin G that determine isotype-specific differences in complement activation," (1993) Journal of Experimental Medicine 178(2):661-667.
Tarte et al., "BAFF is a survival factor for multiple myeloma cells," Myeloma Biology II (2002) p. 811a (Abstract #3203).
Thakur et al., "Cancer therapy with bispecific antibodies: Clinical experience," (2010) Current Opinion in Molecular Therapeutics 12(3):340-349.
Tiller et al., "Facile Affinity Maturation of Antibody Variable Domains Using Natural Diversity Mutagenesis," (2017) Front Immunol. 8:986, DOI: 10.3389/fimmu.2017.00986.
Topp et al., "Anti-B-Cell Maturation Antigen BiTE Molecule AMG 420 Induces Responses in Multiple Myeloma," (2020) J Clin Oncol. 38(8):775-783.
Trinklein et al., "Abstract LB-090: Sequence-based Discovery of Fully Human Anti-CD3 and Anti-PDL1 Single Domain Antibodies Using Novel Transgenic Rats," (2016) Cancer Research 76(14 Suppl), DOI: 10.1158/1538-7445.AM2016-LB-090.
Trinklein et al., "Efficient Tumor Killing and Minimal Cytokine Release with Novel T-Cell Agonist Bispecific Antibodies," (2019) mAbs 11(4):639-652.
Turesson et al., "Patterns of Improved Survival in Patients with Multiple Myeloma in the Twenty-First Century: A Population-Based Study," (2010) Journal of Clinical Oncology 28(5):830-834.
Vafa et al., "Perspective: Designing T-cell engagers with better therapeutic windows," (2020) *Frontiers in Oncology* 10:446, DOI: 10.3389/fonc.2020.00446.
Van der Linden et al., "Comparison of Physical Chemical Properties of Llama $V_{HH}$ Antibody Fragments and Mouse Monoclonal Antibodies," (1999) Biochimica et Biophysica Acta 1431(1):37-46.
Van Schooten et al., "A Novel CD3/BCMA Bispecific Antibody Selectively Kills Plasma Cells in Bone Marrow of Healthy Individuals with Improved Safety," (2019) Lupus Science and Medicine 6, DOI: 10.1136/lupus-2019-lsm.293.
Verkleij et al., "T-Cell Redirecting Bispecific Antibodies Targeting BCMA for the Treatment of Multiple Myeloma," (2020) Oncotarget 11(45):4076-4081, DOI: 10.18632/oncotarget.27792.
Vidal-Laliena et al., "Characterization of antibodies submitted to the B cell section of the 8th Human Leukocyte Differentiation Antigens Workshop by flow cytometry and immunohistochemistry," (2005) Cellular Immunol. 236:6-16.
Vincke et al., "General strategy to humanize a camelid single-domain antibody and identification of a universal humanized nanobody scaffold," (2009) J Biol Chem. 284(5):3273-3284.
Vu et al., "A New Class of T-cell Bispecific Antibodies for the Treatment of Multiple Myeloma, Binding to B Cell Maturation Antigen and CD3 and Showing Potent, Specific Antitumor Activity in Myeloma Cells and Long Duration of Action in Cynomolgus Monkeys," (2015) Blood 126(23):2998, DOI: 10.1182/blood.V126.23.2998.2998.
Wagner et al., "A Two-Step Approach for the Design and Generation of Nanobodies," (2018) Int J Mol Sci 19(11):3444, DOI: 10.3390/ijms19113444, 16 pages.
Walker et al., "CD22: An Inhibitory Enigma," (2008) Immunology 123(3):314-325.
Wallweber et al., "The Crystal Structure of a Proliferation-Inducing Ligand, APRIL," (2004) J Mol Biol. 343(2):283-290.
Waxman et al., "Racial disparities in incidence and outcome in multiple myeloma: a population-based study," (2010) Blood 116(25):5501-5506, DOI: 10.1182/blood-2010-07-298760.
Wayback Machine Snapshot of BCMA UniprotKB/Swiss-Prot Entry, Aug. 3, 2011, Retrieved from the Internet: <https://web.archive.org/web/20110803071256/ https://www.uniprot.orq/uniprot/Q02223> [Inactive Link].
Werther et al., "Humanization of Anti-Lymphocyte Function-Associated Antigen (LFA)-1 Monoclonal Antibody and Reengineering of the Humanized Antibody for Binding to Rhesus LFA-1," (1996) Journal of Immunology 157:4986-4995.
Winter et al., "Humanized Antibodies," (1993) Immunol Today 14(6):243-246.

(56) References Cited

OTHER PUBLICATIONS

Written Opinion for PCT Application No. PCT/US2020/026686, mailed on Jul. 27, 2020.
Wu et al., "CD38-Expressing Macrophages Drive Age-Related NAD+ Decline," (2020) Nature Metabolism 2:1186-1187.
Wu et al., "Simultaneous Targeting of Multiple Disease Mediators by a Dual-Variable-Domain Immunoglobulin," (2007) Nature Biotechnology 25:1290-1297.
Yau et al., "Affinity maturation of a V(H)H by mutational hotspot randomization," (2005) Journal of Immunological Methods 297 (Issues 1-2):213-224.
Yoon et al., "Both High and Low Avidity Antibodies to the T Cell Receptor Can Have Agonist or Antagonist Activity," (1994) Immunity 1(7):563-569.
Zare et al., "Production of nanobodies against prostate-specific membrane antigen (PSMA) recognizing LnCaP cells," (2014) Int J Biol Markers 29(2):e169-e179, DOI: 10.5301/jbm.5000063.
Zarei et al., "High Efficient Expression of a Functional Humanized Single-Chain Variable Fragment (scFv) Antibody Against CD22 in Pichia Pastoris," (2014) Applied Microbiology and Biotechnology 98(24):10023-10039.
Zavrtanik et al., "Structural Basis of Epitope Recognition by Heavy-Chain Camelid Antibodies," (2018) J Mol Biol. 430(21):4369-4386.
Zhao et al., "A germline knowledge based computational approach for determining antibody complementarity determining regions," (2010) Molecular Immunology 47(4):694-700.
Zou et al., "Heavy Chain-Only Antibodies are Spontaneously Produced in Light Chain-Deficient," (2007) J Exp Med. 204(13):3271-3283.
Beckman et al., "Antibody Constructs in Cancer Therapy: Protein Engineering Strategies to Improve Exposure in Solid Tumors", Cancer, vol. 109 (2), pp. 170-179 (2007).
Bostrom et al., "Improving antibody binding affinity and specificity for therapeutic development," Methods Mol Biol., 525: 353-376 (2009).
Chiu et al., "A PSMA-Targeting CD3 Bispecific Antibody Induces Antitumor Responses that Are Enhanced by 4-1BB Costimulation," Cancer Immunol. Res., vol. 8, pp. 596-608 (2020).
Fujimori et al., "A Modeling Analysis of Monoclonal Antibody Percolation Through Tumors: A Binding-Site Barrier", J. Nucl. Med., vol. 31 (7), pp. 1191-1198 (1990).
Gonzales et al., "Minimizing the Immunogenicity of Antibodies for Clinical Application," Tumor Biol., 26(1): 31-43 (2005).
Huang et al., "Recombinant immunotherapeutics: current state and perspectives regarding the feasibility and market," Appl. Microbiol. Biotechnol., vol. 87, pp. 401-410 (2010).
Kunik et al., "Structural consensus among antibodies defines the antigen binding site," PLoS Comput Biol., vol. 8 (2; e1002388), pp. 1-12 (2012).
Rudnick and Adams, "Affinity and Avidity in Antibody-Based Tumor Targeting", Cancer Biother. Radiopharm., vol. 24 (2), pp. 155-162 (2009).
Thurber et al., "Antibody tumor penetration: Transport opposed by systemic and antigen-mediated clearance," Adv. Drug Deliv. Rev., vol. 60, pp. 1421-1434 (2008).
Wark et al., "Latest technologies for the enhancement of antibody affinity," Adv. Drug Deliv. Rev., vol. 58, pp. 657-670 (2006).
Falchook et al., "Phase 1 clinical trial of AMG 340, a prostate-specific membrane antigen (PSMA)-targeted T-cell engager with a novel low-affinity CD3 binding domain designed to mitigate toxicity for the treatment of metastatic castration-resistant prostate cancer (mCRPC)," J. Clin. Oncol., vol. 42(16), Suppl., e14587 (2024).

* cited by examiner

Anti-CD3 x bivalent, biparatopic anti-PSMA

Anti-CD3 x bivalent, monospecific anti-PSMA

Anti-CD3 x monovalent, monospecific anti-PSMA

HEAVY CHAIN ANTIBODIES BINDING TO PSMA

CROSS-REFERENCE TO RELATED APPLICATIONS

This application is a U.S. national stage application under 35 U.S.C. § 371 of International Application No. PCT/US2020/026686, filed Apr. 3, 2020, which claims priority benefit of the filing date of U.S. Provisional Patent Application No. 62/830,130, filed on Apr. 5, 2019, the disclosure of each of which is herein incorporated by reference in its entirety.

FIELD OF THE INVENTION

The present invention concerns human heavy chain antibodies (e.g., UniAbs™) binding to PSMA. The invention further concerns methods of making such antibodies, compositions, including pharmaceutical compositions, comprising such antibodies, and their use to treat disorders that are characterized by the expression of PSMA.

BACKGROUND OF THE INVENTION

PSMA

PSMA, also known as Prostate Specific Membrane Antigen and Glutamate Carboxypeptidase 11 (UniProt Q04609), is a type 11 transmembrane protein that has N-acetylated-alpha-linked-acidic dipeptidase, folate hydrolase and dipeptidyl-peptidase activity. It is encoded by the FOLH1 gene in humans and consists of a 19 amino acid cytoplasmic domain, a 24 amino acid transmembrane portion, and a 707 amino acid extracellular portion. The protein is enzymatically active as a non-covalent homodimer. PSMA is expressed on prostate epithelium tissue and is upregulated in prostate cancer and the neovasculature of solid tumors. It is also expressed at low levels in healthy tissues such as the brain, kidney, and salivary glands, but its overexpression in malignant prostate tissue makes it an attractive target for the therapeutic treatment of prostate cancer. It may also be relevant for therapy or imaging of solid tumors, given its high expression in malignant neovasculature. Monoclonal antibodies, antibody-drug conjugates and chimeric antigen receptor T-cells targeting PSMA have been described for treatment of metastatic prostate cancer (Hernandez-Hoyos et al 2016, PMID: 27406985, DiPippo et al 2014, PMID: 25327986, Serganova et al 2016, PMID: 28345023). In addition, radionuclide conjugates specific to PSMA are being investigated for imaging and treatment of prostate cancer (e.g., Hofman et al., 2018 PMID: 29752180).

Heavy Chain Antibodies

In a conventional IgG antibody, the association of the heavy chain and light chain is due in part to a hydrophobic interaction between the light chain constant region and the CH1 constant domain of the heavy chain. There are additional residues in the heavy chain framework 2 (FR2) and framework 4 (FR4) regions that also contribute to this hydrophobic interaction between the heavy and light chains.

It is known, however, that sera of camelids (sub-order Tylopoda which includes camels, dromedaries and llamas) contain a major type of antibodies composed solely of paired H-chains (heavy-chain only antibodies or UniAbs™). The UniAbs™ of Camelidae (*Camelus dromedarius, Camelus bactrianus, Lama glama, Lama guanaco, Lama* alpaca and *Lama vicugna*) have a unique structure consisting of a single variable domain (VHH), a hinge region and two constant domains (CH2 and CH3), which are highly homologous to the CH2 and CH3 domains of classical antibodies. These UniAbs™ lack the first domain of the constant region (CH1) which is present in the genome, but is spliced out during mRNA processing. The absence of the CH1 domain explains the absence of the light chain in the UniAbs™, since this domain is the anchoring place for the constant domain of the light chain. Such UniAbs™ naturally evolved to confer antigen-binding specificity and high affinity by three CDRs from conventional antibodies or fragments thereof (Muyldermans, 2001; *J Biotechnol* 74:277-302; Revets et al., 2005; *Expert Opin Biol Ther* 5:111-124). Cartilaginous fish, such as sharks, have also evolved a distinctive type of immunoglobulin, designated as IgNAR, which lacks the light polypeptide chains and is composed entirely by heavy chains. IgNAR molecules can be manipulated by molecular engineering to produce the variable domain of a single heavy chain polypeptide (vNARs) (Nuttall et al. *Eur. J. Biochem.* 270, 3543-3554 (2003); Nuttall et al. *Function and Bioinformatics* 55, 187-197 (2004); Dooley et al., *Molecular-Immunology* 40, 25-33 (2003)).

The ability of heavy chain-only antibodies devoid of light chain to bind antigen was established in the 1960s (Jaton et al. (1968) *Biochemistry*, 7, 4185-4195). Heavy chain immunoglobulin physically separated from light chain retained 80% of antigen-binding activity relative to the tetrameric antibody. Sitia et al. (1990) *Cell*, 60, 781-790 demonstrated that removal of the CH1 domain from a rearranged mouse gene results in the production of a heavy chain-only antibody, devoid of light chain, in mammalian cell culture. The antibodies produced retained VH binding specificity and effector functions.

Heavy chain antibodies with a high specificity and affinity can be generated against a variety of antigens through immunization (van der Linden, R. H., et al. *Biochim. Biophys. Acta.* 1431, 37-46 (1999)) and the VHH portion can be readily cloned and expressed in yeast (Frenken, L. G. J., et al. *J. Biotechnol.* 78, 11-21 (2000)). Their levels of expression, solubility and stability are significantly higher than those of classical F(ab) or Fv fragments (Ghahroudi, M. A. et al. *FEBS Lett.* 414, 521-526 (1997)).

Mice in which the λ (lambda) light (L) chain locus and/or the λ and κ (kappa) L chain loci have been functionally silenced and antibodies produced by such mice are described in U.S. Pat. Nos. 7,541,513 and 8,367,888. Recombinant production of heavy chain-only antibodies in mice and rats has been reported, for example, in WO2006008548; U.S. Application Publication No. 20100122358; Nguyen et al., 2003, *Immunology;* 109(1), 93-101; Brüggemann et al., *Crit. Rev. Immunol.;* 2006, 26(5):377-90; and Zou et al., 2007, *J Exp Med;* 204(13): 3271-3283. The production of knockout rats via embryo microinjections of zinc-finger nucleases is described in Geurts et al., 2009, *Science,* 325(5939):433. Soluble heavy chain-only antibodies and transgenic rodents comprising a heterologous heavy chain locus producing such antibodies are described in U.S. Pat. Nos. 8,883,150 and 9,365,655. CAR-T structures comprising single-domain antibodies as binding (targeting) domain are described, for example, in Tri-Sofla et al., 2011, *Experimental Cell Research* 317:2630-2641 and Jamnani et al., 2014, *Biochim Biophys Acta,* 1840:378-386.

SUMMARY OF THE INVENTION

Aspects of the invention relate to heavy chain antibodies, including but not limited to UniAbs™, with binding affinity to PSMA. Further aspects of the invention relate to methods of making such antibodies, compositions comprising such antibodies, and their use in the treatment of disorders that are characterized by the expression of PSMA.

In some embodiments, an antibody binding to PSMA comprises a first heavy chain variable region comprising: (a) a CDR1 having two or fewer substitutions in any of the amino acid sequences of SEQ ID NOs: 1 to 10; and/or (b) a CDR2 having two or fewer substitutions in any of the amino acid sequences of SEQ ID NOs: 11 to 17; and/or (c) a CDR3 having two or fewer substitutions in any of the amino acid sequences of SEQ ID NOs: 18 to 23. In some embodiments, the antibody further comprises a second heavy chain variable region comprising: (a) a CDR1 having two or fewer substitutions in any of the amino acid sequences of SEQ ID NOs: 1 to 10; and/or (b) a CDR2 having two or fewer substitutions in any of the amino acid sequences of SEQ ID NOs: 11 to 17; and/or (c) a CDR3 having two or fewer substitutions in any of the amino acid sequences of SEQ ID NOs: 18 to 23. In some embodiments, the CDR1, CDR2, and CDR3 sequences are present in a human framework. In some embodiments, an antibody further comprises a heavy chain constant region sequence in the absence of a CH1 sequence.

In some embodiments, the first heavy chain variable region of the antibody comprises: (a) a CDR1 sequence selected from the group consisting of SEQ ID NOs: 1 to 10; and/or (b) a CDR2 sequence selected from the group consisting of SEQ ID NOs: 11 to 17; and/or (c) a CDR3 sequence selected from the group consisting of SEQ ID NOs: 18 to 23.

In some embodiments, the antibody further comprises a second heavy chain variable region which comprises: (a) a CDR1 sequence selected from the group consisting of SEQ ID NOs: 1 to 10; and/or (b) a CDR2 sequence selected from the group consisting of SEQ ID NOs: 11 to 17; and/or (c) a CDR3 sequence selected from the group consisting of SEQ ID NOs: 18 to 23.

In some embodiments, the antibody comprises: (a) a CDR1 sequence selected from the group consisting of SEQ ID NOs: 1 to 10; and (b) a CDR2 sequence selected from the group consisting of SEQ ID NOs: 11 to 17; and (c) a CDR3 sequence selected from the group consisting of SEQ ID NOs: 18 to 23. In some embodiments, the antibody comprises a second heavy chain variable region which comprises: (a) a CDR1 sequence selected from the group consisting of SEQ ID NOs: 1 to 10; and (b) a CDR2 sequence selected from the group consisting of SEQ ID NOs: 11 to 17; and (c) a CDR3 sequence selected from the group consisting of SEQ ID NOs: 18 to 23.

In some embodiments, the antibody comprises: (a) a CDR1 sequence of SEQ ID NO: 2, a CDR2 sequence of SEQ ID NO: 11, and a CDR3 sequence of SEQ ID NO: 18; or (b) a CDR1 sequence of SEQ ID NO: 7, a CDR2 sequence of SEQ ID NO: 15, and a CDR3 sequence of SEQ ID NO: 20. In some embodiments, the antibody comprises a heavy chain variable region sequence having at least 95% sequence identity to any one of the sequences of SEQ ID NOs: 24 to 58. In some embodiments, an antibody comprises a heavy chain variable region sequence selected from the group consisting of SEQ ID NOs: 24 to 58. In some embodiments, the antibody comprises a heavy chain variable region sequence is selected from the group consisting of: SEQ ID NO: 25 and SEQ ID NO: 38.

In some embodiments, an antibody binding to PSMA comprises a first heavy chain variable region comprising: (a) a CDR1 sequence of the formula:

$$G\ G\ S\ I\ S\ S\ X_1\ X_2\ Y\ X_3 \quad (\text{SEQ ID NO: 67})$$

where $X_1$ is S or N; $X_2$ is S or N; and $X_3$ is Y or F; and (b) a CDR2 sequence of the formula:

$$X_4\ X_5\ X_6\ S\ G\ X_7\ T \quad (\text{SEQ ID NO: 68})$$

where $X_4$ is I or V; $X_5$ is D or Y; $X_6$ is Y or D; and $X_7$ is Y or S; and (c) a CDR3 sequence of the formula:
  A R H K A A T A D F D Y (SEQ ID NO: 69), in a monovalent or bivalent format.

In some embodiments, a, antibody binding to PSMA comprises a first heavy chain variable region comprising: (a) a CDR1 sequence of the formula:

$$G\ F\ X_1\ F\ X_2\ X_3\ Y\ G \quad (\text{SEQ ID NO: 70})$$

where $X_1$ is S or I or T; $X_2$ is S or T or R or I; and $X_3$ is R or S; and (b) a CDR2 sequence of the formula:

$$I\ X_4\ Y\ D\ G\ S\ N\ X_5 \quad (\text{SEQ ID NO: 71})$$

where $X_4$ is W or S; and $X_5$ is R or K; and (c) a CDR3 sequence of the formula:

$$A\ R\ E\ P\ R\ X_6\ G\ Y\ Y\ Y\ X_7\ X_8\ S\ G\ Y\ X_9\ S\ L\ D\ Y \quad (\text{SEQ ID NO: 72})$$

where $X_6$ is I or V; $X_7$ is E or D; $X_8$ is S or T; and $X_9$ is Y or D, in a monovalent or bivalent format.

In some embodiments, an antibody binding PSMA comprises: a first heavy chain variable region comprising: (a) a CDR1 sequence of the formula:

$$G\ G\ S\ I\ S\ S\ X_1\ X_2\ Y\ X_3 \quad (\text{SEQ ID NO: 67})$$

where $X_1$ is S or N; $X_2$ is S or N; and $X_3$ is Y or F; and (b) a CDR2 sequence of the formula:

$$X_4\ X_5\ X_6\ S\ G\ X_7\ T \quad (\text{SEQ ID NO: 68})$$

where $X_4$ is I or V; $X_5$ is D or Y; $X_6$ is Y or D; and $X_7$ is Y or S; and (c) a CDR3 sequence of the formula:
  A R H K A A T A D F D Y (SEQ ID NO: 69), and a second heavy chain variable region comprising: (a) a CDR1 sequence of the formula:

$$G\ F\ X_1\ F\ X_2\ X_3\ Y\ G \quad (\text{SEQ ID NO: 70})$$

where $X_1$ is S or I or T; $X_2$ is S or T or R or I; and $X_3$ is R or S; and (b) a CDR2 sequence of the formula:

$$I\ X_4\ Y\ D\ G\ S\ N\ X_5 \quad (\text{SEQ ID NO: 71})$$

where $X_4$ is W or S; and $X_5$ is R or K; and (c) a CDR3 sequence of the formula:

A R E P R $X_6$ G Y Y Y $X_7$ $X_8$ S G Y $X_9$ S L D Y (SEQ ID NO: 72)

where $X_6$ is I or V; $X_7$ is E or D; $X_8$ is S or T; and $X_9$ is Y or D.

In some embodiments, the antibody comprises a first and a second heavy chain variable region, wherein the first heavy chain variable region is located nearer to the N-terminus relative to the second heavy chain variable region. In some embodiments, the first heavy chain variable region is located nearer to the C-terminus relative to the second heavy chain variable region.

In some embodiments, an antibody binding to PSMA comprises a heavy chain variable region comprising CDR1, CDR2 and CDR3 sequences in a human VH framework, wherein the CDR sequences comprise a sequence having two or fewer substitutions in a CDR sequence selected from the group consisting of SEQ ID NOs: 1-23.

In some embodiments, an antibody binding to PSMA comprises a heavy chain variable region comprising CDR1, CDR2 and CDR3 sequences in a human VH framework, wherein the CDR sequences are selected from the group consisting of SEQ ID NOs: 1-23.

In some embodiments, an antibody binding to PSMA comprises: a heavy chain variable region comprising a CDR1 sequence of SEQ ID NO: 2, a CDR2 sequence of SEQ ID NO: 11, and a CDR3 sequence of SEQ ID NO: 18 in a human VH framework.

In some embodiments, an antibody binding to PSMA comprises: a heavy chain variable region comprising a CDR1 sequence of SEQ ID NO: 2, a CDR2 sequence of SEQ ID NO: 11, and a CDR3 sequence of SEQ ID NO: 18 in a human VH framework, in a monovalent or bivalent configuration.

In some embodiments, an antibody binding to PSMA comprises: a heavy chain variable region comprising a CDR1 sequence of SEQ ID NO: 7, a CDR2 sequence of SEQ ID NO: 15, and a CDR3 sequence of SEQ ID NO: 20 in a human VH framework.

In some embodiments, an antibody binding to PSMA comprises: a heavy chain variable region comprising a CDR1 sequence of SEQ ID NO: 7, a CDR2 sequence of SEQ ID NO: 15, and a CDR3 sequence of SEQ ID NO: 20 in a human VH framework, in monovalent or bivalent configuration.

In some embodiments, an antibody binding to PSMA comprises: a first heavy chain variable region comprising: a CDR1 sequence of SEQ ID NO: 2, a CDR2 sequence of SEQ ID NO: 11, and a CDR3 sequence of SEQ ID NO: 18; and a second heavy chain variable region comprising: a CDR1 sequence of SEQ ID NO: 7, a CDR2 sequence of SEQ ID NO: 15, and a CDR3 sequence of SEQ ID NO: 20, in a human VH framework. In some embodiments, the antibody comprises a first heavy chain variable region which is located nearer to the N-terminus relative to the second heavy chain variable region. In some embodiments, the first heavy chain variable region is located nearer to the C-terminus relative to the second heavy chain variable region.

In some embodiments, an antibody is monospecific. In some embodiments, an antibody is multi-specific. In some embodiments, an antibody is bispecific. In some embodiments, an antibody has binding affinity to a CD3 protein and a PSMA protein. In some embodiments, an antibody has binding affinity to two different epitopes on the same PSMA protein. In some embodiments, an antibody has binding affinity to an effector cell. In some embodiments, an antibody has binding affinity to a T-cell antigen. In some embodiments, an antibody has binding affinity to CD3. In some embodiments, an antibody is in a CAR-T format.

Aspects of the invention include a bispecific antibody comprising: (i) a heavy chain variable region having binding affinity to CD3, comprising a CDR1 sequence of SEQ ID NO: 59, a CDR2 sequence of SEQ ID NO: 60, and CDR3 sequence of SEQ ID NO: 61, in a human VH framework; (ii) a light chain variable region comprising a CDR1 sequence of SEQ ID NO: 62, a CDR2 sequence of SEQ ID NO: 63, and CDR3 sequences of SEQ ID NO: 64, in a human VL framework; and (iii) an antigen-binding domain of an anti-PSMA heavy chain antibody, comprising a CDR1 sequence of SEQ ID NO: 2, a CDR2 sequence of SEQ ID NO: 11, and a CDR3 sequence of SEQ ID NO: 18, in a human VH framework.

Aspects of the invention include a bispecific antibody comprising: (i) a heavy chain variable region having binding affinity to CD3, comprising a CDR1 sequence of SEQ ID NO: 59, a CDR2 sequence of SEQ ID NO: 60, and CDR3 sequence of SEQ ID NO: 61, in a human VH framework; (ii) a light chain variable region comprising a CDR1 sequence of SEQ ID NO: 62, a CDR2 sequence of SEQ ID NO: 63, and CDR3 sequences of SEQ ID NO: 64, in a human VL framework; and (iii) an antigen-binding domain of an anti-PSMA heavy chain antibody, comprising a CDR1 sequence of SEQ ID NO: 2, a CDR2 sequence of SEQ ID NO: 11, and a CDR3 sequence of SEQ ID NO: 18, in a human VH framework, in a monovalent or bivalent configuration.

Aspects of the invention include a bispecific antibody comprising: (i) a heavy chain variable region having binding affinity to CD3, comprising a CDR1 sequence of SEQ ID NO: 59, a CDR2 sequence of SEQ ID NO: 60, and CDR3 sequence of SEQ ID NO: 61, in a human VH framework; (ii) a light chain variable region comprising a CDR1 sequence of SEQ ID NO: 62, a CDR2 sequence of SEQ ID NO: 63, and CDR3 sequences of SEQ ID NO: 64, in a human VL framework; and (iii) an antigen-binding domain of an anti-PSMA heavy chain antibody, comprising a CDR1 sequence of SEQ ID NO: 7, a CDR2 sequence of SEQ ID NO: 15, and a CDR3 sequence of SEQ ID NO: 20, in a human VH framework.

Aspects of the invention include a bispecific antibody comprising: (i) a heavy chain variable region having binding affinity to CD3, comprising a CDR1 sequence of SEQ ID NO: 59, a CDR2 sequence of SEQ ID NO: 60, and CDR3 sequence of SEQ ID NO: 61, in a human VH framework; (ii) a light chain variable region comprising a CDR1 sequence of SEQ ID NO: 62, a CDR2 sequence of SEQ ID NO: 63, and CDR3 sequences of SEQ ID NO: 64, in a human VL framework; and (iii) an antigen-binding domain of an anti-PSMA heavy chain antibody, comprising a CDR1 sequence of SEQ ID NO: 7, a CDR2 sequence of SEQ ID NO: 15, and a CDR3 sequence of SEQ ID NO: 20, in a human VH framework, in a monovalent or bivalent configuration.

Aspects of the invention include a multi-specific antibody comprising: (i) a heavy chain variable region having binding affinity to CD3, comprising a CDR1 sequence of SEQ ID NO: 59, a CDR2 sequence of SEQ ID NO: 60, and CDR3 sequence of SEQ ID NO: 61, in a human VH framework; (ii) a light chain variable region comprising a CDR1 sequence of SEQ ID NO: 62, a CDR2 sequence of SEQ ID NO: 63, and CDR3 sequences of SEQ ID NO: 64, in a human VL framework; and (iii) an antigen-binding domain of an anti- PSMA heavy chain antibody, wherein the antigen-binding domain comprises a first and a second antigen-binding region, in a bivalent configuration, wherein: the first antigen-binding region comprises a CDR1 sequence of SEQ ID NO: 2, a CDR2 sequence of SEQ ID NO: 11, and a CDR3 sequence of SEQ ID NO: 18, in a human VH framework; and the second antigen-binding region comprises a CDR1 sequence of SEQ ID NO: 7, a CDR2 sequence of SEQ ID NO: 15, and a CDR3 sequence of SEQ ID NO: 20, in a human VH framework. In certain embodiments, the first antigen-binding region is located nearer to the N-terminus relative to the second antigen-binding region. In certain other embodiments, the first antigen-binding region is located nearer to the C-terminus relative to the second antigen-binding region.

Aspects of the invention include multispecific or bispecific antibodies wherein the first and second antigen-binding regions of the antigen-binding domain of the anti-PSMA heavy chain antibody are connected by a polypeptide linker. In some embodiments, the polypeptide linker is a GS linker. In some embodiments, the GS linker consists of the sequence of SEQ ID NO: 73 or SEQ ID NO: 74. In some embodiments, the antigen-binding domain of the anti-PSMA heavy chain antibody is monoparatopic, and induces less cytokine production as compared to a biparatopic antigen-binding domain. In some embodiments, the antigen-binding domain of the anti-PSMA heavy chain antibody is monoparatopic, and expands CD8+ T-cells to a greater extent than a biparatopic antigen-binding domain.

In some embodiments, an antibody is biparatopic and has increased affinity for PSMA as compared to a monoparatopic anti-PSMA antibody. In some embodiments, an antibody is biparatopic and has increased effector function as compared to a monoparatopic anti-PSMA antibody.

Aspects of the invention relate to pharmaceutical compositions comprising an antibody described herein.

Aspects of the invention relate to methods for the treatment of a disorder characterized by expression of PSMA, comprising administering to a subject with said disorder an antibody or a pharmaceutical composition described herein. In certain other aspects, the invention relates to uses of an antibody described herein, in the preparation of a medicament for the treatment of a disorder characterized by expression of PSMA. In yet other aspects, the invention relates to an antibody described herein for use in the treatment of a disorder characterized by expression of PSMA. In certain other aspects, the invention relates to methods of treatment, comprising administering to an individual in need an effective dose of an antibody or a pharmaceutical composition described herein. With respect to these aspects, and in some embodiments, the disorder is prostate cancer.

Aspects of the invention relate to polynucleotides encoding an antibody described herein, vectors comprising such polynucleotides, and cells comprising such vectors.

Aspects of the invention relate to methods of producing an antibody described herein, comprising growing a cell described herein under conditions permissive for expression of the antibody, and isolating the antibody from the cell.

Aspects of the invention relate to methods of making an antibody described herein, comprising immunizing a UniRat animal with a PSMA protein and identifying PSMA-binding antibody sequences.

These and further aspects will be further explained in the rest of the disclosure, including the Examples.

BRIEF DESCRIPTION OF THE DRAWINGS

FIG. 2, panel B is a graph showing cell binding to cynomolgus monkey PSMA.

FIG. 4, panel B is a Scatchard plot showing binding affinity to cell surface expressed PSMA of a bispecific antibody having binding affinity to CD3 and PSMA, wherein the PSMA arm is biparatopic according to an embodiment of the invention.

FIG. 11, panel B, is a graph depicting T-cell proliferation as a function of antibody concentration.

FIG. 11, panel C, is a graph depicting the ratio of CD8 to CD4 of proliferated T-cells.

FIG. 11, panel D, is a graph depicting the ratio of CD8 to CD4 of proliferated T-cells.

FIG. 12, panel B, is a graph depicting cytokine (IFNγ) release as a function of antibody concentration.

FIG. 12, panel C, is a graph depicting cytokine (IL-2) release as a function of antibody concentration.

DETAILED DESCRIPTION OF THE PREFERRED EMBODIMENTS

Figure 1A:
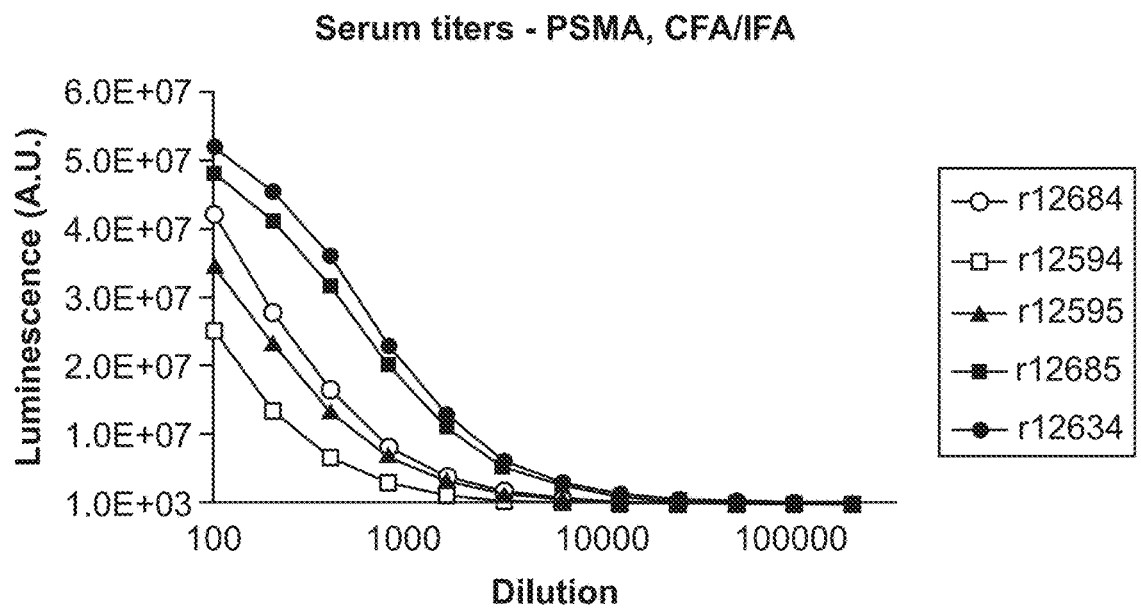
FIG. 1, panels A-B, provide a series of graphs showing serum titer as a function of dilution.

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, "*Molecular Cloning: A Laboratory Manual*", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "*Current Protocols in Molecular Biology*" (F. M. Ausubel et al., eds., 1987, and periodic updates); "PCR: The Polymerase Chain Reaction", (Mullis et al., ed., 1994); "*A Practical Guide to Molecular Cloning*" (Perbal Bernard V., 1988); "*Phage Display: A Laboratory Manual*" (Barbas et al., 2001); Harlow, Lane and Harlow, *Using Antibodies: A Laboratory Manual*: Portable Protocol No. I, Cold Spring Harbor Laboratory (1998); and Harlow and Lane, *Antibodies: A Laboratory Manual*, Cold Spring Harbor Laboratory; (1988).

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

Unless indicated otherwise, antibody residues herein are numbered according to the Kabat numbering system (e.g., Kabat et al., *Sequences of Immunological Interest.* 5th Ed. Public Health Service, National Institutes of Health, Bethesda, Md. (1991)).

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

All references cited throughout the disclosure, including patent applications and publications, are incorporated by reference herein in their entirety.

I. Definitions

By "comprising" it is meant that the recited elements are required in the composition/method/kit, but other elements may be included to form the composition/method/kit etc. within the scope of the claim.

By "consisting essentially of", it is meant a limitation of the scope of composition or method described to the specified materials or steps that do not materially affect the basic and novel characteristic(s) of the subject invention.

By "consisting of", it is meant the exclusion from the composition, method, or kit of any element, step, or ingredient not specified in the claim.

Antibody residues herein are numbered according to the Kabat numbering system and the EU numbering system. The Kabat numbering system is generally used when referring to a residue in the variable domain (approximately residues 1-113 of the heavy chain) (e.g., Kabat et al., *Sequences of Immunological Interest.* 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody. Unless stated otherwise herein, references to residue numbers in the variable domain of antibodies mean residue numbering by the Kabat numbering system. Unless stated otherwise herein, references to residue numbers in the constant domain of antibodies mean residue numbering by the EU numbering system.

Antibodies, also referred to as immunoglobulins, conventionally comprise at least one heavy chain and one light chain, where the amino terminal domain of the heavy and light chains is variable in sequence, hence is commonly referred to as a variable region domain, or a variable heavy (VH) or variable light (VL) domain. The two domains conventionally associate to form a specific binding region, although as will be discussed here, specific binding can also be obtained with heavy chain-only variable sequences, and a variety of non-natural configurations of antibodies are known and used in the art.

A "functional" or "biologically active" antibody or antigen-binding molecule (including heavy chain-only antibodies and multi-specific (e.g., bispecific) three-chain antibody-like molecules (TCAs, described herein) is one capable of exerting one or more of its natural activities in structural, regulatory, biochemical or biophysical events. For example, a functional antibody or other binding molecule, e.g., a TCA, may have the ability to specifically bind an antigen and the binding may in turn elicit or alter a cellular or molecular event such as signal transduction or enzymatic activity. A functional antibody or other binding molecule, e.g., a TCA, may also block ligand activation of a receptor or act as an agonist or antagonist. The capability of an antibody or other binding molecule, e.g., a TCA, to exert one or more of its natural activities depends on several factors, including proper folding and assembly of the polypeptide chains.

The term "antibody" herein is used in the broadest sense and specifically covers monoclonal antibodies, polyclonal antibodies, monomers, dimers, multimers, multispecific antibodies (e.g., bispecific antibodies), heavy chain-only antibodies, three chain antibodies, TCAs, single chain Fv (scFv), nanobodies, etc., and also includes antibody fragments, so long as they exhibit the desired biological activity (Miller et al (2003) *Jour. of Immunology* 170:4854-4861). Antibodies may be murine, human, humanized, chimeric, or derived from other species.

The term antibody may reference a full-length heavy chain, a full length light chain, an intact immunoglobulin molecule; or an immunologically active portion of any of these polypeptides, i.e., a polypeptide that comprises an antigen binding site that immunospecifically binds an antigen of a target of interest or part thereof, such targets including but not limited to, cancer cell or cells that produce autoimmune antibodies associated with an autoimmune disease. The immunoglobulin disclosed herein can be of any type (e.g., IgG, IgE, IgM, IgD, and IgA), class (e.g., IgG1, IgG2, IgG3, IgG4, IgA1 and IgA2) or subclass of immunoglobulin molecule, including engineered subclasses with altered Fc portions that provide for reduced or enhanced effector cell activity. Light chains of the subject antibodies can be kappa light chains (Vkappa) or lambda light chains (Vlambda). The immunoglobulins can be derived from any species. In one aspect, the immunoglobulin is of largely human origin.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen.

Monoclonal antibodies in accordance with the present invention can be made by the hybridoma method first described by Kohler et al. (1975) *Nature* 256:495, and can also be made via recombinant protein production methods (see, e.g., U.S. Pat. No. 4,816,567), for example.

The term "variable", as used in connection with antibodies, refers to the fact that certain portions of the antibody variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health, Bethesda, MD. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g., residues 31-35 (H1), 50-65 (H2) and 95-102 (H3) in the heavy chain variable domain; Kabat et al., *Sequences of Proteins of Immunological Interest*, 5th Ed. Public Health Service, National Institutes of Health, Bethesda, MD. (1991)) and/or those residues from a "hypervariable loop" residues 26-32 (H1), 53-55 (H2) and 96-101 (H3) in the heavy chain variable domain; Chothia and Lesk. *J. Mol. Biol.* 196:901-917 (1987)). In some embodiments, "CDR" means a complementary determining region of an antibody as defined in Lefranc, M P et al., IMGT, the international ImMunoGeneTics database, *Nucleic Acids Res.*, 27:209-212 (1999). "Framework Region" or "FR" residues are those variable domain residues other than the hypervariable region/CDR residues as herein defined.

Exemplary CDR designations are shown herein, however one of skill in the art will understand that a number of definitions of the CDRs are commonly in use, including the Kabat definition (see "Zhao et al. A germline knowledge based computational approach for determining antibody complementarity determining regions." *Mol Immunol.* 2010; 47:694-700), which is based on sequence variability and is the most commonly used. The Chothia definition is based on the location of the structural loop regions (Chothia et al. "Conformations of immunoglobulin hypervariable regions." *Nature.* 1989; 342:877-883). Alternative CDR definitions of interest include, without limitation, those disclosed by Honegger, "Yet another numbering scheme for immunoglobulin variable domains: an automatic modeling and analysis tool." *J Mol Biol.* 2001:309:657-670; Ofran et al. "Automated identification of complementarity determining regions (CDRs) reveals peculiar characteristics of CDRs and B-cell epitopes." *J Immunol.* 2008; 181:6230-6235; Almagro "Identification of differences in the specificity-determining residues of antibodies that recognize antigens of different size: implications for the rational design of antibody repertoires." *J Mol Recognit.* 2004; 17:132-143; and Padlan et al. "Identification of specificity-determining residues in antibodies." *Faseb J.* 1995; 9:133-139., each of which is herein specifically incorporated by reference.

The terms "heavy chain-only antibody," and "heavy chain antibody" are used interchangeably herein and refer, in the broadest sense, to antibodies, or more or more portions of an antibody, e.g., one or more arms of an antibody, lacking the light chain of a conventional antibody. The terms specifically include, without limitation, homodimeric antibodies comprising the VH antigen-binding domain and the CH2 and CH3 constant domains, in the absence of the CH1 domain; functional (antigen-binding) variants of such antibodies, soluble VH variants, Ig-NAR comprising a homodimer of one variable domain (V-NAR) and five C-like constant domains (C-NAR) and functional fragments thereof; and soluble single domain antibodies (sUniDabs™). In one embodiment, a heavy chain-only antibody is composed of a variable region antigen-binding domain composed of framework 1, CDR1, framework 2, CDR2, framework 3, CDR3, and framework 4. In another embodiment, a heavy chain-only antibody is composed of an antigen-binding domain, at least part of a hinge region and CH2 and CH3 domains. In another embodiment, a heavy chain-only antibody is composed of an antigen-binding domain, at least part of a hinge region and a CH2 domain. In a further embodiment, a heavy chain-only antibody is composed of an antigen-binding domain, at least part of a hinge region and a CH3 domain. Heavy chain-only antibodies in which the CH2 and/or CH3 domain is truncated are also included herein. In a further embodiment, a heavy chain is composed of an antigen binding domain, and at least one CH (CH1, CH2, CH3, or CH4) domain but no hinge region. The heavy chain-only antibody can be in the form of a dimer, in which two heavy chains are disulfide bonded or otherwise, covalently or non-covalently, attached with each other. The heavy chain-only antibody may belong to the IgG subclass, but antibodies belonging to other subclasses, such as IgM, IgA, IgD and IgE subclass, are also included herein. In a particular embodiment, a heavy chain antibody is of the IgG1, IgG2, IgG3, or IgG4 subtype, in particular the IgG1 subtype. In one embodiment, the heavy chain-only antibodies herein are used as a binding (targeting) domain of a chimeric antigen receptor (CAR). The definition specifically includes human heavy chain-only antibodies produced by human immunoglobulin transgenic rats (UniRat™), called UniAbs™. The variable regions (VH) of UniAbs™ are called UniDabs™, and are versatile building blocks that can be linked to Fc regions or serum albumin for the development of novel therapeutics with multi-specificity, increased potency and extended half-life. Since the homodimeric UniAbs™ lack a light chain and thus a VL domain, the antigen is recognized by one single domain, i.e., the variable domain of the heavy chain of a heavy-chain antibody (VH or VHH).

An "intact antibody chain" as used herein is one comprising a full length variable region and a full length constant region (Fc). An intact "conventional" antibody comprises an intact light chain and an intact heavy chain, as well as a light chain constant domain (CL) and heavy chain constant domains, CH1, hinge, CH2 and CH3 for secreted IgG. Other isotypes, such as IgM or IgA may have different CH domains. The constant domains may be native sequence constant domains (e.g., human native sequence constant domains) or amino acid sequence variants thereof. The intact antibody may have one or more "effector functions" which refer to those biological activities attributable to the Fc constant region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; and down regulation of cell surface receptors. Constant region variants include those that alter the effector profile, binding to Fc receptors, and the like.

Depending on the amino acid sequence of the Fc (constant domain) of their heavy chains, antibodies and various antigen-binding proteins can be provided as different classes. There are five major classes of heavy chain Fc regions: IgA, IgD, IgE, IgG, and IgM, and several of these may be further divided into "subclasses" (isotypes), e.g., IgG1, IgG2, IgG3, IgG4, IgA, and IgA2. The Fc constant domains that correspond to the different classes of antibodies may be referenced as α, δ, ε, γ, and, respectively. The subunit structures and three-dimensional configurations of different classes of immunoglobulins are well known. Ig forms include hinge-modifications or hingeless forms (Roux et al (1998) *J. Immunol.* 161:4083-4090; Lund et al (2000) *Eur. J. Biochem.* 267:7246-7256; US 2005/0048572; US 2004/0229310). The light chains of antibodies from any vertebrate species can be assigned to one of two types, called κ (kappa) and λ (lambda), based on the amino acid sequences of their constant domains. Antibodies in accordance with embodiments of the invention can comprise kappa light chain sequences or lambda light chain sequences.

A "functional Fc region" possesses an "effector function" of a native-sequence Fc region. Non-limiting examples of effector functions include C1q binding; CDC; Fc-receptor binding; ADCC; ADCP; down-regulation of cell-surface receptors (e.g., B-cell receptor), etc. Such effector functions generally require the Fc region to interact with a receptor, e.g., the FcγRI; FcγRIIA; FcγRIIB1; FcγRIIB2; FcγRIIIA; FcγRIIIB receptors, and the low affinity FcRn receptor; and can be assessed using various assays known in the art. A "dead" or "silenced" Fc is one that has been mutated to retain activity with respect to, for example, prolonging serum half-life, but which does not activate a high affinity Fc receptor, or which has a reduced affinity to an Fc receptor.

A "native-sequence Fc region" comprises an amino acid sequence identical to the amino acid sequence of an Fc region found in nature. Native-sequence human Fc regions include, for example, a native-sequence human IgG1 Fc region (non-A and A allotypes); native-sequence human IgG2 Fc region; native-sequence human IgG3 Fc region; and native-sequence human IgG4 Fc region, as well as naturally occurring variants thereof.

A "variant Fc region" comprises an amino acid sequence that differs from that of a native-sequence Fc region by virtue of at least one amino acid modification, preferably one or more amino acid substitution(s). Preferably, the variant Fc region has at least one amino acid substitution compared to a native-sequence Fc region or to the Fc region of a parent polypeptide, e.g., from about one to about ten amino acid substitutions, and preferably from about one to about five amino acid substitutions in a native-sequence Fc region or in the Fc region of the parent polypeptide. The variant Fc region herein will preferably possess at least about 80% homology with a native-sequence Fc region and/or with an Fc region of a parent polypeptide, and most preferably at least about 90% homology therewith, more preferably at least about 95% homology therewith.

Variant Fc sequences may include three amino acid substitutions in the CH2 region to reduce FcγRI binding at EU index positions 234, 235, and 237 (see Duncan et al., (1988) *Nature* 332:563). Two amino acid substitutions in the complement C1q binding site at EU index positions 330 and 331 reduce complement fixation (see Tao et al., *J. Exp. Med.* 178:661 (1993) and Canfield and Morrison, *J. Exp. Med.* 173:1483 (1991)). Substitution into human IgG1 or IgG2 residues at positions 233-236 and IgG4 residues at positions 327, 330 and 331 greatly reduces ADCC and CDC (see, for example, Armour KL. et al., 1999 *Eur J Immunol.* 29(8): 2613-24; and Shields RL. et al., 2001. *J Biol Chem.* 276(9): 6591-604). The human IgG4 Fc amino acid sequence (UniProtKB No. P01861) is provided herein as SEQ ID NO: 76. Silenced IgG1 is described, for example, in Boesch, A. W., et al., "Highly parallel characterization of IgG Fc binding interactions." *MAbs,* 2014. 6(4): p. 915-27, the disclosure of which is incorporated herein by reference in its entirety.

Other Fc variants are possible, including, without limitation, one in which a region capable of forming a disulfide bond is deleted, or in which certain amino acid residues are eliminated at the N-terminal end of a native Fc, or a methionine residue is added thereto. Thus, in some embodiments, one or more Fc portions of an antibody can comprise one or more mutations in the hinge region to eliminate disulfide bonding. In yet another embodiment, the hinge region of an Fc can be removed entirely. In still another embodiment, an antibody can comprise an Fc variant.

Further, an Fc variant can be constructed to remove or substantially reduce effector functions by substituting (mutating), deleting or adding amino acid residues to effect complement binding or Fc receptor binding. For example, and not limitation, a deletion may occur in a complement-binding site, such as a C1q-binding site. Techniques for preparing such sequence derivatives of the immunoglobulin Fc fragment are disclosed in International Patent Publication Nos. WO 97/34631 and WO 96/32478. In addition, the Fc domain may be modified by phosphorylation, sulfation, acylation, glycosylation, methylation, farnesylation, acetylation, amidation, and the like.

In some embodiments, an antibody comprises a variant human IgG4 CH3 domain sequence comprising a T366W mutation, which can optionally be referred to herein as an IgG4 CH3 knob sequence. In some embodiments, an antibody comprises a variant human IgG4 CH3 domain sequence comprising a T366S mutation, an L368A mutation, and a Y407V mutation, which can optionally be referred to herein as an IgG4 CH3 hole sequence. The IgG4 CH3 mutations described herein can be utilized in any suitable manner so as to place a "knob" on a first heavy chain constant region of a first monomer in an antibody dimer, and a "hole" on a second heavy chain constant region of a second monomer in an antibody dimer, thereby facilitating proper pairing (heterodimerization) of the desired pair of heavy chain polypeptide subunits in the antibody.

In some embodiments, an antibody comprises a heavy chain polypeptide subunit comprising a variant human IgG4 Fc region comprising an S228P mutation, an F234A mutation, an L235A mutation, and a T366W mutation (knob). In some embodiments, and antibody comprises a heavy chain polypeptide subunit comprising a variant human IgG4 Fc region comprising an S228P mutation, an F234A mutation, an L235A mutation, a T366S mutation, an L368A mutation, and a Y407V mutation (hole).

The term "Fc-region-comprising antibody" refers to an antibody that comprises an Fc region. The C-terminal lysine (residue 447 according to the EU numbering system) of the Fc region may be removed, for example, during purification of the antibody or by recombinant engineering of the nucleic acid encoding the antibody. Accordingly, an antibody having an Fc region according to this invention can comprise an antibody with or without K447.

Aspects of the invention include antibodies comprising a heavy chain-only variable region in a monovalent or bivalent configuration. As used herein, the term "monovalent configuration" as used in reference to a heavy chain-only variable region domain means that only one heavy chain-only variable region domain is present, having a single binding site (see FIG. 5, Panel A, right arm of antibody). In contrast, the term "bivalent configuration" as used in reference to a heavy chain-only variable region domain means that two heavy chain-only variable region domains are present (each having a single binding site), and are connected by a linker sequence (see FIG. 5, Panels B and C, right arms of antibodies). Non-limiting examples of linker sequences are discussed further herein, and include, without limitation, GS linker sequences of various lengths. When a heavy chain-only variable region is in a bivalent configuration, each of the two heavy chain-only variable region domains can have binding affinity to the same antigen, or to different antigens (e.g., to different epitopes on the same protein; to two different proteins, etc.). However, unless specifically noted otherwise, a heavy chain-only variable region denoted as being in a "bivalent configuration" is understood to contain two identical heavy chain-only variable region domains, connected by a linker sequence, wherein each of the two identical heavy chain-only variable region domains have binding affinity to the same target antigen.

Aspects of the invention include antibodies having multi-specific configurations, which include, without limitation, bispecific, trispecific, etc. A large variety of methods and protein configurations are known and used in bispecific monoclonal antibodies (BsMAB), tri-specific antibodies, etc.

Various methods for the production of multivalent artificial antibodies have been developed by recombinantly fusing variable domains of two or more antibodies. In some embodiments, a first and a second antigen-binding domain on a polypeptide are connected by a polypeptide linker. One non-limiting example of such a polypeptide linker is a GS linker, having an amino acid sequence of four glycine residues, followed by one serine residue, and wherein the sequence is repeated n times, where n is an integer ranging from 1 to about 10, such as 2, 3, 4, 5, 6, 7, 8, or 9. Non-limiting examples of such linkers include GGGGS (SEQ ID NO: 73) (n=1) and GGGGSGGGGS (SEQ ID NO: 74 (n=2). Other suitable linkers can also be used, and are described, for example, in Chen et al., *Adv Drug Deliv Rev.* 2013 October 15; 65(10): 1357-69, the disclosure of which is incorporated herein by reference in its entirety.

The term "three-chain antibody like molecule" or "TCA" is used herein to refer to antibody-like molecules comprising, consisting essentially of, or consisting of three polypeptide subunits, two of which comprise, consist essentially of, or consist of one heavy and one light chain of a monoclonal antibody, or functional antigen-binding fragments of such antibody chains, comprising an antigen-binding region and at least one CH domain. This heavy chain/light chain pair has binding specificity for a first antigen. The third polypeptide subunit comprises, consists essentially of, or consists of a heavy-chain only antibody comprising an Fc portion comprising CH2 and/or CH3 and/or CH4 domains, in the absence of a CH1 domain, and one or more antigen binding domains (e.g., two antigen binding domains) that binds an epitope of a second antigen or a different epitope of the first antigen, where such binding domain is derived from or has sequence identity with the variable region of an antibody heavy or light chain. Parts of such variable region may be encoded by $V_H$ and/or $V_L$ gene segments, D and $J_H$ gene segments, or $J_L$ gene segments. The variable region may be encoded by rearranged $V_H DJ_H$, $V_L DJ_H$, $V_H J_L$, or $V_L J_L$ gene segments.

A TCA binding compound makes use of a "heavy chain only antibody" or "heavy chain antibody" or "heavy chain polypeptide" which, as used herein, mean a single chain antibody comprising heavy chain constant regions CH2 and/or CH3 and/or CH4 but no CH1 domain. In one embodiment, the heavy chain antibody is composed of an antigen-binding domain, at least part of a hinge region and CH2 and CH3 domains. In another embodiment, the heavy chain antibody is composed of an antigen-binding domain, at least part of a hinge region and a CH2 domain. In a further embodiment, the heavy chain antibody is composed of an antigen-binding domain, at least part of a hinge region and a CH3 domain. Heavy chain antibodies in which the CH2 and/or CH3 domain is truncated are also included herein. In a further embodiment, the heavy chain is composed of an antigen binding domain, and at least one CH (CH1, CH2, CH3, or CH4) domain but no hinge region. The heavy chain only antibody can be in the form of a dimer, in which two heavy chains are disulfide bonded other otherwise covalently or non-covalently attached with each other, and can optionally include an asymmetric interface between one or more of the CH domains to facilitate proper pairing between polypeptide chains. The heavy-chain antibody may belong to the IgG subclass, but antibodies belonging to other subclasses, such as IgM, IgA, IgD and IgE subclass, are also included herein. In a particular embodiment, the heavy chain antibody is of the IgG1, IgG2, IgG3, or IgG4 subtype, in particular the IgG1 subtype or the IgG4 subtype. Non-limiting examples of a TCA binding compound are described in, for example, WO2017/223111 and WO2018/052503, the disclosures of which are incorporated herein by reference in their entirety.

Heavy-chain antibodies constitute about one fourth of the IgG antibodies produced by the camelids, e.g., camels and llamas (Hamers-Casterman C., et al. *Nature.* 363, 446-448 (1993)). These antibodies are formed by two heavy chains but are devoid of light chains. As a consequence, the variable antigen binding part is referred to as the VHH domain and it represents the smallest naturally occurring, intact, antigen-binding site, being only around 120 amino acids in length (Desmyter, A., et al. *J. Biol. Chem.* 276, 26285-26290 (2001)). Heavy chain antibodies with a high specificity and affinity can be generated against a variety of antigens through immunization (van der Linden, R. H., et al. *Biochim. Biophys. Acta.* 1431, 37-46 (1999)) and the VHH portion can be readily cloned and expressed in yeast (Frenken, L. G. J., et al. *J. Biotechnol.* 78, 11-21 (2000)). Their levels of expression, solubility and stability are significantly higher than those of classical F(ab) or Fv fragments (Ghahroudi, M. A. et al. *FEBS Lett.* 414, 521-526 (1997)). Sharks have also been shown to have a single VH-like domain in their antibodies, termed VNAR. (Nuttall et al. *Eur. J. Biochem.* 270, 3543-3554 (2003); Nuttall et al. *Function and Bioinformatics* 55, 187-197 (2004); Dooley et al., *Molecular Immunology* 40, 25-33 (2003)).

The term "PSMA" as used herein refers to a type II transmembrane protein that has N-acetylated-alpha-linked acidic dipeptidase, folate hydrolase and dipeptidyl-peptidase activity. The term "PSMA" includes a PSMA protein of any human and non-human animal species, and specifically includes human PSMA as well as PSMA of non-human mammals.

The term "human PSMA" as used herein includes any variants, isoforms and species homologs of human PSMA (UniProt Q04609), regardless of its source or mode of preparation. Thus, "human PSMA" includes human PSMA naturally expressed by cells and PSMA expressed on cells transfected with the human PSMA gene.

The terms "anti-PSMA heavy chain-only antibody," "PSMA heavy chain-only antibody," "anti-PSMA heavy chain antibody" and "PSMA heavy chain antibody" are used herein interchangeably to refer to a heavy chain-only antibody as hereinabove defined, immunospecifically binding to PSMA, including human PSMA, as hereinabove defined. The definition includes, without limitation, human heavy chain antibodies produced by transgenic animals, such as transgenic rats or transgenic mice expressing human immunoglobulin, including UniRats™ producing human anti-PSMA UniAb™ antibodies, as hereinabove defined.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR™) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

Antibodies of the invention include multi-specific antibodies. Multi-specific antibodies have more than one binding specificity. The term "multi-specific" specifically includes "bispecific" and "trispecific," as well as higher-order independent specific binding affinities, such as higher-order polyepitopic specificity, as well as tetravalent antibodies and antibody fragments. The terms "multi-specific antibody," "multi-specific heavy chain-only antibody," "multi-specific heavy chain antibody," and "multi-specific UniAb™," are used herein in the broadest sense and cover all antibodies with more than one binding specificity. The multi-specific heavy chain anti-PSMA antibodies of the present invention specifically include antibodies immunospecifically binding to two or more non-overlapping epitopes on a PSMA protein, such as a human PSMA (i.e., bivalent and biparatopic). The multi-specific heavy chain anti-PSMA antibodies of the present invention also specifically include antibodies immunospecifically binding to an epitope on a PSMA protein, such as human PSMA and to an epitope on a different protein, such as, for example, a CD3 protein, such as human CD3 (i.e., bivalent and biparatopic). The multi-specific heavy chain anti-PSMA antibodies of the present invention also specifically include antibodies immunospecifically binding to two or more non-overlapping or partially overlapping epitopes on a PSMA protein, such as a human PSMA protein, and to an epitope on a different protein, such as, for example, a CD3 protein, such as human CD3 protein (i.e., trivalent and biparatopic).

Antibodies of the invention include monospecific antibodies, having one binding specificity. Monospecific antibodies specifically include antibodies comprising a single binding specificity, as well as antibodies comprising more than one binding unit having the same binding specificity. The terms "monospecific antibody." "monospecific heavy chain-only antibody," "monospecific heavy chain antibody," and "monospecific UniAb™" are used herein in the broadest sense and cover all antibodies with one binding specificity. The monospecific heavy chain anti-PSMA antibodies of the present invention specifically include antibodies immunospecifically binding to one epitope on a PSMA protein, such as a human PSMA (monovalent and monospecific). The monospecific heavy chain anti-PSMA antibodies of the present invention also specifically include antibodies having more than one binding unit (e.g., multivalent antibodies) immunospecifically binding to an epitope on a PSMA protein, such as human PSMA. For example, a monospecific antibody in accordance with embodiments of the invention can include a heavy chain variable region comprising two antigen-binding domains, wherein each antigen-binding domain binds to the same epitope on a PSMA protein (i.e., bivalent and monospecific).

An "epitope" is the site on the surface of an antigen molecule to which a single antibody molecule binds. Generally, an antigen has several or many different epitopes and reacts with many different antibodies. The term specifically includes linear epitopes and conformational epitopes.

"Epitope mapping" is the process of identifying the binding sites, or epitopes, of antibodies on their target antigens. Antibody epitopes may be linear epitopes or conformational epitopes. Linear epitopes are formed by a continuous sequence of amino acids in a protein. Conformational epitopes are formed of amino acids that are discontinuous in the protein sequence, but which are brought together upon folding of the protein into its three-dimensional structure.

"Polyepitopic specificity" refers to the ability to specifically bind to two or more different epitopes on the same or different target(s). As noted above, the present invention specifically includes anti-PSMA heavy chain antibodies with polyepitopic specificities, i.e., anti-PSMA heavy chain antibodies binding to one or more non-overlapping epitopes on a PSMA protein, such as a human PSMA; and anti-PSMA heavy chain antibodies binding to one or more epitopes on a PSMA protein and to an epitope on a different protein, such as, for example, a CD3 protein. The term "non-overlapping epitope(s)" or "non-competitive epitope(s)" of an antigen is defined herein to mean epitope(s) that are recognized by one member of a pair of antigen-specific antibodies but not the other member. Pairs of antibodies, or antigen-binding regions targeting the same antigen on a multi-specific antibody, recognizing non-overlapping epitopes, do not compete for binding to that antigen and are able to bind that antigen simultaneously.

An antibody binds "essentially the same epitope" as a reference antibody, when the two antibodies recognize identical or sterically overlapping epitopes. The most widely used and rapid methods for determining whether two epitopes bind to identical or sterically overlapping epitopes are competition assays, which can be configured in all number of different formats, using either labeled antigen or labeled antibody. Usually, the antigen is immobilized on a 96-well plate, and the ability of unlabeled antibodies to block the binding of labeled antibodies is measured using radioactive or enzyme labels.

The term "valent" as used herein refers to a specified number of binding sites in an antibody molecule.

A "monovalent" antibody has one binding site. Thus, a monovalent antibody is also monospecific.

A "multi-valent" antibody has two or more binding sites. Thus, the terms "bivalent", "trivalent", and "tetravalent" refer to the presence of two binding sites, three binding sites, and four binding sites, respectively. Thus, a bispecific antibody according to the invention is at least bivalent and may be trivalent, tetravalent, or otherwise multi-valent. A bivalent antibody in accordance with embodiments of the invention may have two binding sites to the same epitope (i.e., bivalent, monoparatopic), or to two different epitopes (i.e., bivalent, biparatopic).

A large variety of methods and protein configurations are known and used for the preparation of bispecific monoclonal antibodies (BsMAB), ti-specific antibodies, and the like.

The term "three-chain antibody like molecule" or "TCA" is used herein to refer to antibody-like molecules comprising, consisting essentially of, or consisting of three polypeptide subunits, two of which comprise, consist essentially of, or consist of one heavy chain and one light chain of a monoclonal antibody, or functional antigen-binding fragments of such antibody chains, comprising an antigen-binding region and at least one CH domain. This heavy chain/light chain pair has binding specificity for a first antigen. The third polypeptide subunit comprises, consists essentially of, or consists of a heavy chain-only antibody comprising an Fc portion comprising CH2 and/or CH3 and/or CH4 domains, in the absence of a CH1 domain, and an antigen binding domain that binds an epitope of a second antigen or a different epitope of the first antigen, where such binding domain is derived from or has sequence identity with the variable region of an antibody heavy or light chain. Parts of such variable region may be encoded by $V_H$ and/or VL gene segments, D and JH gene segments, or $J_L$ gene segments. The variable region may be encoded by rearranged $V_H DJ_H$, $V_L DJ_H$, $V_H J_L$, or $V_L J_L$ gene segments. A TCA protein makes use of a heavy chain-only antibody as hereinabove defined.

The term "chimeric antigen receptor" or "CAR" is used herein in the broadest sense to refer to an engineered receptor, which grafts a desired binding specificity (e.g., the antigen-binding region of a monoclonal antibody or other ligand) to membrane-spanning and intracellular-signaling domains. Typically, the receptor is used to graft the specificity of a monoclonal antibody onto a T-cell to create a chimeric antigen receptors (CAR). (*J Natl Cancer Inst,* 2015; 108(7):dvj439; and Jackson et al., *Nature Reviews Clinical Oncology,* 2016; 13:370-383). CAR-T cells are T-cells that have been genetically engineered to produce an artificial T-cell receptor for use in immunotherapy. In one embodiment, "CAR-T cell" means a therapeutic T-cell expressing a transgene encoding one or more chimeric antigen receptors comprised minimally of an extracellular domain, a transmembrane domain, and at least one cytosolic domain.

The term "human antibody" is used herein to include antibodies having variable and constant regions derived from human germline immunoglobulin sequences. The human antibodies herein may include amino acid residues not encoded by human germline immunoglobulin sequences, e.g., mutations introduced by random or site-specific mutagenesis in vitro or by somatic mutation in vivo. The term "human antibody" specifically includes heavy chain-only antibodies having human heavy chain variable region sequences, produced by transgenic animals, such as transgenic rats or mice, in particular UniAbs™ produced by UniRats™, as defined above.

By a "chimeric antibody" or a "chimeric immunoglobulin" is meant an immunoglobulin molecule comprising amino acid sequences from at least two different Ig loci, e.g., a transgenic antibody comprising a portion encoded by a human Ig locus and a portion encoded by a rat Ig locus. Chimeric antibodies include transgenic antibodies with non-human Fc-regions or artificial Fc-regions, and human idiotypes. Such immunoglobulins can be isolated from animals of the invention that have been engineered to produce such chimeric antibodies.

As used herein, the term "effector cell" refers to an immune cell which is involved in the effector phase of an immune response, as opposed to the cognitive and activation phases of an immune response. Some effector cells express specific Fc receptors and carry out specific immune functions. In some embodiments, an effector cell such as a natural killer cell is capable of inducing antibody-dependent cellular cytotoxicity (ADCC). For example, monocytes and macrophages, which express FcR, are involved in specific killing of target cells and presenting antigens to other components of the immune system, or binding to cells that present antigens. In some embodiments, an effector cell may phagocytose a target antigen or target cell.

"Human effector cells" are leukocytes which express receptors such as T-cell receptors or FcRs and perform effector functions. Preferably, the cells express at least FcγRIII and perform ADCC effector function. Examples of human leukocytes which mediate ADCC include natural killer (NK) cells, monocytes, cytotoxic T-cells and neutrophils; with NK cells being preferred. The effector cells may be isolated from a native source thereof, e.g., from blood or PBMCs as described herein.

The term "immune cell" is used herein in the broadest sense, including, without limitation, cells of myeloid or lymphoid origin, for instance lymphocytes (such as B-cells and T-cells including cytolytic T-cells (CTLs)), killer cells, natural killer (NK) cells, macrophages, monocytes, cosinophils, polymorphonuclear cells, such as neutrophils, granulocytes, mast cells, and basophils.

Antibody "effector functions" refer to those biological activities attributable to the Fc region (a native sequence Fc region or amino acid sequence variant Fc region) of an antibody. Examples of antibody effector functions include C1q binding; complement dependent cytotoxicity (CDC); Fc receptor binding; antibody-dependent cell-mediated cytotoxicity (ADCC); phagocytosis; down regulation of cell surface receptors (e.g., B-cell receptor; BCR), etc.

"Antibody-dependent cell-mediated cytotoxicity" and "ADCC" refer to a cell-mediated reaction in which nonspecific cytotoxic cells that express Fc receptors (FcRs) (e.g., Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *PNAS* (USA) 95:652-656 (1998).

"Complement dependent cytotoxicity" or "CDC" refers to the ability of a molecule to lyse a target in the presence of complement. The complement activation pathway is initiated by the binding of the first component of the complement system (Clq) to a molecule (e.g. an antibody) complexed with a cognate antigen. To assess complement activation, a CDC assay, e.g., as described in Gazzano-Santoro et al., *J. Immunol. Methods* 202:163 (1996), may be performed.

"Binding affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art. Low-affinity antibodies generally bind antigen slowly and tend to dissociate readily, whereas high-affinity antibodies generally bind antigen faster and tend to remain bound.

As used herein, the "Kd" or "Kd value" refers to a dissociation constant determined by Biolayer Interferometry, using an Octet® QK384 instrument (Fortebio Inc., Menlo Park, CA) in kinetics mode. For example, anti-mouse Fc sensors are loaded with mouse-Fc fused antigen and then dipped into antibody-containing wells to measure concentration dependent association rates (kon). Antibody dissociation rates (koff) are measured in the final step, where the sensors are dipped into wells containing buffer only. The Kd is the ratio of koff/kon. (For further details see, Concepcion, J, et al., *Comb Chem High Throughput Screen,* 12(8), 791-800, 2009).

The terms "treatment", "treating" and the like are used herein to generally mean obtaining a desired pharmacologic and/or physiological effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy may be administered during the symptomatic stage of the disease, and in some cases after the symptomatic stage of the disease.

A "therapeutically effective amount" is intended for an amount of active agent which is necessary to impart therapeutic benefit to a subject. For example, a "therapeutically effective amount" is an amount which induces, ameliorates or otherwise causes an improvement in the pathological symptoms, disease progression or physiological conditions associated with a disease or which improves resistance to a disorder.

The term "prostate cancer," as used herein, refers to a malignant tumor of glandular origin in the prostate gland.

The term "characterized by expression of PSMA" broadly refers to any disease or disorder in which PSMA expression is associated with or involved with one or more pathological processes that are characteristic of the disease or disorder. Such disorders include, but are not limited to, prostate cancer.

The terms "subject," "individual," and "patient" are used interchangeably herein to refer to a mammal being assessed for treatment and/or being treated. In an embodiment, the mammal is a human. The terms "subject," "individual," and "patient" encompass, without limitation, individuals having cancer, individuals with autoimmune diseases, with pathogen infections, and the like. Subjects may be human, but also include other mammals, particularly those mammals useful as laboratory models for human disease, e.g., mouse, rat, etc.

The term "pharmaceutical formulation" refers to a preparation which is in such form as to permit the biological activity of the active ingredient to be effective, and which contains no additional components which are unacceptably toxic to a subject to which the formulation would be administered. Such formulations are sterile. "Pharmaceutically acceptable" excipients (vehicles, additives) are those which can reasonably be administered to a subject mammal to provide an effective dose of the active ingredient employed.

A "sterile" formulation is aseptic or free or essentially free from all living microorganisms and their spores. A "frozen" formulation is one at a temperature below 0° C.

A "stable" formulation is one in which the protein therein essentially retains its physical stability and/or chemical stability and/or biological activity upon storage. Preferably, the formulation essentially retains its physical and chemical stability, as well as its biological activity upon storage. The storage period is generally selected based on the intended shelf-life of the formulation. Various analytical techniques for measuring protein stability are available in the art and are reviewed in *Peptide and Protein Drug Delivery,* 247-301. Vincent Lee Ed., Marcel Dekker, Inc., New York, N.Y., Pubs. (1991) and Jones. A. *Adv. Drug Delivery Rev.* 10: 29-90) (1993), for example. Stability can be measured at a selected temperature for a selected time period. Stability can be evaluated qualitatively and/or quantitatively in a variety of different ways, including evaluation of aggregate formation (for example using size exclusion chromatography, by measuring turbidity, and/or by visual inspection); by assessing charge heterogeneity using cation exchange chromatography, image capillary isoelectric focusing (icIEF) or capillary zone electrophoresis; amino-terminal or carboxy-terminal sequence analysis; mass spectrometric analysis;

SDS-PAGE analysis to compare reduced and intact antibody; peptide map (for example tryptic or LYS-C) analysis; evaluating biological activity or antigen binding function of the antibody; etc. Instability may involve any one or more of aggregation, deamidation (e.g., Asn deamidation), oxidation (e.g., Met oxidation), isomerization (e.g., Asp isomerization), clipping/hydrolysis/fragmentation (e.g., hinge region fragmentation), succinimide formation, unpaired cysteine(s). N-terminal extension, C-terminal processing, glycosylation differences, etc.

II. Detailed Description

Anti-PSMA Antibodies

The present invention provides a family of closely related antibodies that bind to human PSMA. The antibodies of this family comprise a set of CDR sequences as defined herein and shown in Table 1, and are exemplified by the provided heavy chain variable region (VH) sequences of SEQ ID NOs: 24 to 54 set forth in Table 2. The family of antibodies provides a number of benefits that contribute to utility as clinically therapeutic agent(s). The antibodies include members with a range of binding affinities, allowing the selection of a specific sequence with a desired binding affinity.

TABLE 1

Anti-PSMA heavy chain antibody unique CDR amino acid sequences.

| SEQ_aa_CDR1 | SEQ_aa_CDR2 | SEQ_aa_CDR3 |
|---|---|---|
| GGSISSSSYY (SEQ ID NO: 1) | IDYSGYT (SEQ ID NO: 11) | ARHKAATADFDY (SEQ ID NO: 18) |

TABLE 1-continued

Anti-PSMA heavy chain antibody unique CDR amino acid sequences.

| SEQ_aa_CDR1 | SEQ_aa_CDR2 | SEQ_aa_CDR3 |
|---|---|---|
| GGSISSSNYF (SEQ ID NO: 2) | VDYSGYT (SEQ ID NO: 12) | AREPRIGYYYESSGYDSLDY (SEQ ID NO: 19) |
| GGSISSNSYY (SEQ ID NO: 3) | IYDSGST (SEQ ID NO: 13) | AREPRIGYYYESSGYYSLDY (SEQ ID NO: 20) |
| GFSFRSYG (SEQ ID NO: 4) | IWYDGSNK (SEQ ID NO: 14) | AREPRIGYYYDSSGYDSLDY (SEQ ID NO: 21) |
| GFSFSSYG (SEQ ID NO: 5) | IWYDGSNR (SEQ ID NO: 15) | AREPRIGYYYDSSGYYSLDY (SEQ ID NO: 22) |
| GFIFRSYG (SEQ ID NO: 6) | ISYDGSNK (SEQ ID NO: 16) | AREPRVGYYYETSGYYSLDY (SEQ ID NO: 23) |
| GFSFSRYG (SEQ ID NO: 7) | ISYDGSNR (SEQ ID NO: 17) | |
| GFSFTSYG (SEQ ID NO: 8) | | |
| GFTFISYG (SEQ ID NO: 9) | | |
| GFTFSSYG (SEQ ID NO: 10) | | |

TABLE 2

Anti-PSMA heavy chain antibody variable domain amino acid sequences.

| Clone ID # | SEQ_aa_FR1_FR4 | SEQ ID NO. |
|---|---|---|
| 325920 | QLQLQESGPGLVKPSETLSLTCTVSGGSISSSSYYWGWIRQPPGKGLEWIGSIDYSGYTYYNPSLQSRVTISVDTSKNQFSLKLSSVTAADTAVYNCARHKAATADFDYRGQGTLVTVSS | 24 |
| 346181 | QLQLQESGPGLVKPSETLSLTCTVSGGSISSSNYFWGWIRQSPGKGLEWIGSIDYSGYTYYNPSLKSRVTISVDTSKNQFSLKLSSVTAADTAVYNCARHKAATADFDYRGQGTLVTVSS | 25 |
| 346165 | QLQLQESGPGLVKPSETLSLTCTVSGGSISSSSYYWGWIRQPPGKGLEWIGSVDYSGYTYYNPSLQSRVTISVDTSKNQFSLKLSSVTAADTAVYNCARHKAATADFDYRGQGTLVTVSS | 26 |
| 346172 | QLQLQESGPGLVKPSETLSLTCTVSGGSISSSSYYWGWIRQPPGKGLEWIGSIDYSGYTYYNPSLKSRVTISVDTSKNQFSLKLSSVTAADTAVYNCARHKAATADFDYRGQGTLVTVSS | 27 |
| 326109 | QLQLQESGPGLVKPSETLSLTCTVSGGSISSNSYYWGWIRQSPGKGLEWLGSIYDSGSTHYNPSLKSRVIISGDTSKNQFSLKLSSVTAADTAVYYCARHKAATADFDYRGQGTLVTVSS | 28 |
| 325867 | QVQLVESGGGVVQPGRSLRLSCAASGFSFRSYGMHWVRQAPGKGLEWVAVIWYDGSNKYYADSVKGRFTISRDYSKNTLYLQMNSLRAEDTAVYYCAREPRIGYYYESSGYDSLDYRGQGTLVTVSS | 29 |
| 325742 | QVQLVESGGGVVQPGRSLRLSCAASGFSFSSYGMHWVRQAPGKGLEWVAVIWYDGSNKYYADSVKGRFTISRDYSKNTLYLQMNSLRAEDTAVYYCAREPRIGYYYESSGYDSLDYRGQGTLVTVSS | 30 |

TABLE 2-continued

Anti-PSMA heavy chain antibody variable domain amino acid sequences.

| Clone ID # | SEQ_aa_FR1_FR4 | SEQ ID NO. |
|---|---|---|
| 325748 | QVQLVESGGGVVQPGRSLRLSCAASGFSFSSYGMHWVRQAPGKGLEGVAVIWYDGSNRYYADSVKGRFTISRDNSKNTLYLQMNSLRAEDTAVYYCAREPRIGYYYESSGYYSLDYRGQGTLVTVSS | 31 |
| 325940 | QVQLVESGGGVVQPGRSLRLSCAASGFIFRSYGMHWVRQAPGKGPEWVAVIWYDGSNKYYADSVKGRFTISRDNSKNTLYLQMNSLRAEDTAVYYCAREPRIGYYYESSGYYSLDYRGQGTLVTVSS | 32 |
| 325836 | QVQLVESGGGVVQPGRSLRLSCAASGFSFRSYGMHWVRQAPGKGLEWVAVIWYDGSNKYYADSVKGRFTISRDYSKNTLYLQMNSLRAEDTAVYYCAREPRIGYYYDSSGYDSLDYRGQGTLVTVSS | 33 |
| 326027 | QVQLVESGGGVVQPGRSLRLSCAASGFSFRSYGMHWVRQAPGKGLEWVAVIWYDGSNKYYADSVKGRFTISRDNSKNTLYLQMNSLRAEDTAVYYCAREPRIGYYYDSSGYDSLDYRGQGTLVTVSS | 34 |
| 326087 | QVQLVESGGGVVQPGRSLRLSCAASGFIFRSYGMHWVRQAPGKGPEWVAVIWYDGSNKYYADSVKGRFTISRDNSKNTLYLQMNSLRAEDTAVYYCAREPRIGYYYDSSGYDSLDYRGQGTLVTVSS | 35 |
| 326084 | QVQLVESGGGVVQPGRSLRLSCAASGFSFSSYGMHWVRQAPGKGLEGVAVIWYDGSNRYYADSVKGRFTISRDNSKNTLYLQMNSLRAEDTAVYYCAREPRIGYYYDSSGYYSLDYRGQGTLVTVSS | 36 |
| 326028 | QVQLVESGGGVVQPGRSLRLSCAASGFSFRSYGMHWVRQAPGKGLEWVAVISYDGSNKYYADSVKGRFTISRDYSKNTLYLQMNSLRAEDTAVYYCAREPRIGYYYDSSGYDSLDYRGQGTLVTVSS | 37 |
| 345497 | QVQLVESGGGVVQPGRSLRLSCAASGFSFSRYGMHWVRQAPGKGLEGVAVIWYDGSNRYYADSVKGRFTISRDNSKNTLYLQMNSLRAEDTAVYYCAREPRIGYYYESSGYYSLDYRGQGTLVTVSS | 38 |
| 326029 | QVQLVESGGGVVQPGRSLRLSCAASGFSFSRYGMHWVRQAPGKGLEWVAVISYDGSNKYYADSVKGRFTISRDNSKNTLYLQMNSLRAEDTAVYYCAREPRVGYYYETSGYYSLDYRGQGTLVTVSS | 39 |
| 345461 | QVQLVESGGGVVQPGRSLRLSCAASGFSFTSYGMHWVRQAPGKGLEGVAVIWYDGSNRYYADSVKGRFTISRDNSKNTLYLQMNSLRAEDTAVYYCAREPRIGYYYESSGYYSLDYRGQGTLVTVSS | 40 |
| 345493 | QVQLVESGGGVVQPGRSLRLSCAASGFSFSRYGMHWVRQAPGKGLEWVAVIWYDGSNRYYADSVKGRFTISRDNSKNTLYLQMNSLRAEDTAVYYCAREPRIGYYYESSGYYSLDYRGQGTLVTVSS | 41 |
| 345436 | QVQLVESGGGVVQPGRSLRLSCAASGFSFSRYGMHWVRQAPGKGLEWVAVIWYDGSNKYYADSVKGRFTISRDNSKNTLYLQMNSLRAEDTAVYYCAREPRIGYYYESSGYYSLDYRGQGTLVTVSS | 42 |
| 345443 | QVQLVESGGGVVQPGRSLRLSCAASGFSFSSYGMHWVRQAPGKGLEGVAVIWYDGSNRYYADSVKGRFTISRDNSKNTLFLQMNSLRAEDTAVYYCAREPRIGYYYESSGYYSLDYRGQGTLVTVSS | 43 |
| 345490 | QVQLVESGGGLVKPGGSLRLSCAASGFSFSSYGMHWVRQAPGKGLEGVAVIWYDGSNRYYADSVKGRFTISRDNSKNTLYLQMNSLRAEDTAVYYCAREPRIGYYYESSGYYSLDYRGQGTLVTVSS | 44 |
| 345482 | QVQLVESGGGVVQPGRSLRLSCAASGFSFSSYGMHWVRQAPGKGLEGVAVIWYDGSNRYYADSVKGRFTISRDSSKNTLYLQMNSLRAEDTAVYYCAREPRIGYYYESSGYYSLDYRGQGTLVTVSS | 45 |
| 345485 | QVQLVESGGGVVQPGRSLRLSCAASGFSFRSYGMHWVRQAPGKGLEWVAVIWYDGSNKYYADSVKGRFTISRDNSKNTMYLQMNSLRAEDTAVYYCAREPRIGYYYESSGYYSLDYRGQGTLVTVSS | 46 |
| 345463 | QVQLVESGGGVVQPGRSLRLSCAASGFIFRSYGMHWVRQAPGKGPEWVAVIWYDGSNKYYADSVKGRFTISRDNSKNTLYLQMNSLRAEDTAVYYCAREPRIGYYYESSGYYSLDYRGQGTLVTVSS | 47 |
| 325932 | QVQLVESGGGVVQPGRSLRLSCAASGFSFSSYGMHWVRQAPGKGLEGVAVIWYDGSNRYYADSVKGRFTISRDNSKNTLYLQMNSLRAEDTAVYYCAREPRIGYYYESSGYYSLDYRGQGTLVTVSS | 48 |

TABLE 2-continued

Anti-PSMA heavy chain antibody variable domain amino acid sequences.

| Clone ID # | SEQ_aa_FR1_FR4 | SEQ ID NO. |
|---|---|---|
| 345505 | QVQLVESGGGVVQPGRSLRLSCAASGFTFISYGMHWVRQAPGKGLEGVAVIWYDGSNRYYADSVKGRFTISRDNSKNTLYLQMNSLRAEDTAVYYCAREPRIGYYYESSGYYSLDYRGQGTLVTVSS | 49 |
| 345508 | QVQLVESGGGVVQPGRSLRLSCAASGFSFSSYGMHWVRQAPGKGPEWVAVIWYDGSNRYYADSVKGRFTISRDNSKNTLYLQMNSLRAEDTAVYYCAREPRIGYYYESSGYYSLDYRGQGTLVTVSS | 50 |
| 345480 | QVQLVESGGGVVQPGRSLRLSCAASGFSFSSYGMHWVRQAPGKGLEWVAVIWYDGSNRYYADSVKGRFTISRDNSKNTLYLQMNSLRAEDTAVYYCAREPRIGYYYESSGYYSLDYRGQGTLVTVSS | 51 |
| 326116 | QVQLVESGGGVVQPGRSLRLSCAASGFSFSRYGMHWVRQAPGKGLEGVAVISYDGSNKYYADSVKGRFTISRDYSKNTLYLQMNSLRAEDTAVYYCAREPRIGYYYDSSGYDSLDYRGQGTLVTVSS | 52 |
| 345509 | QVQLVESGGGLVQPGGSLRLSCAASGFSFSSYGMHWVRQAPGKGLEGVAVIWYDGSNKYYADSVKGRFTISRDNSKNTMYLQMNSLRAEDTAVYYCAREPRIGYYYESSGYYSLDYRGQGTLVTVSS | 53 |
| 345444 | QVQLVESGGGVVQPGRSLRLSCAASGFTFSSYGMHWVRQAPGKGLEGVAVIWYDGSNRYYADSVKGRFTISRDNSKNTLYLQMNSLRAEDTAVYYCAREPRIGYYYESSGYYSLDYRGQGTLVTVSS | 54 |
| 345421 | QVQLVESVGGVVQPGRSLRLSCAASGFSFSSYGMHWVRQAPGKGLEGVAVIWYDGSNRYYADSVKGRFTISRDNSKNTLYLQMNSLRAEDTAVYYCAREPRIGYYYESSGYYSLDYRGQGTLVTVSS | 55 |
| 345447 | QVQLVESGGGVVQPGRSLRLSCAASGFSFSSYGMHWVRQAPGKGLEGVAVISYDGSNRYYADSVKGRFTISRDNSKNTLYLQMNSLRAEDTAVYYCAREPRIGYYYESSGYYSLDYRGQGTLVTVSS | 56 |
| 345510 | QVQLVESGGGVVQPGRSLRLSCAASGFSFSSYGMHWVRQAPGKGLEWVAVIWYDGSNKYYADSVKGRFTISRDNSKNTMYLQMNSLRAEDTAVYYCAREPRIGYYYESSGYYSLDYRGQGTLVTVSS | 57 |
| 345438 | QVQLVESGGGVVQPGRSLRLSCAASGFSFSSYGMHWVRQAPGKGPEWVAVIWYDGSNKYYADSVKGRFTISRDNSKNTLYLQMNSLRAEDTAVYYCAREPRIGYYYESSGYYSLDYRGQGTLVTVSS | 58 |

Figure 5C:
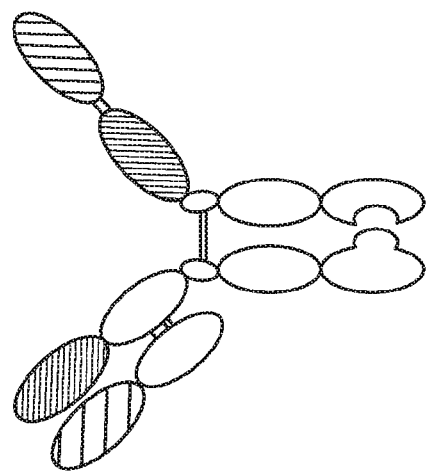
FIG. 5, panels A-C, provide schematic illustrations of an anti-CD3×monovalent, monospecific anti-PSMA antibody (panel A); an anti-CD3×bivalent, monospecific anti-PSMA antibody (panel B); and an anti-CD3×bivalent, biparatopic anti-PSMA antibody (panel C) in accordance with embodiments of the invention.
Figure 5B:
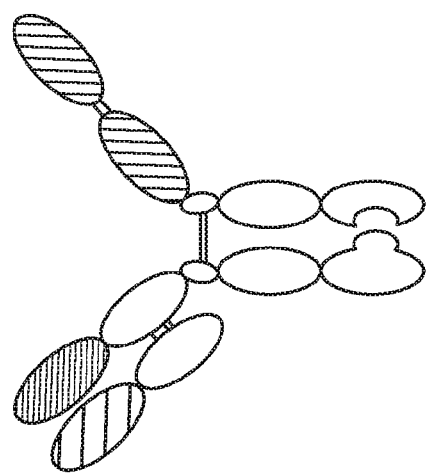
Figure 5A:
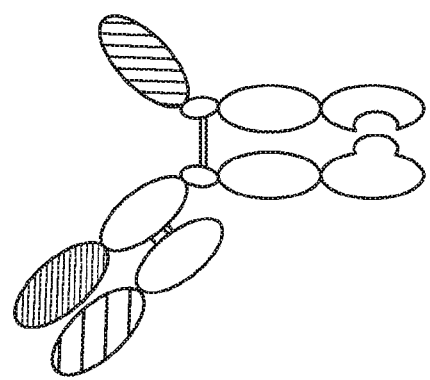

A suitable antibody may be selected from those provided herein for development and therapeutic or other use, including, without limitation, use as a bispecific antibody, e.g., as shown in FIG. 5, panels A-C, or a tri-specific antibody, or part of a CAR-T structure. FIG. 5, panels A-C provide illustrations of anti-CD3×anti-PSMA multi-specific antibodies, where the anti-PSMA domain is monovalent and monospecific, bivalent and monospecific, or bivalent and bispecific (biparatopic). The anti-CD3 domain contains a CH1 domain and pairs with a light chain, while the anti-PSMA domains are derived from heavy chain-only antibodies and do not contain a CH1 domain or interact with a light chain. In some embodiments, the two heavy chains are pared using, e.g., knobs-into-holes technology. Turning to the antibodies depicted in FIG. 5, panel A depicts an anti-CD3×anti-PSMA bispecific antibody wherein the anti-PSMA binding arm is monovalent and monospecific, and the antigen-binding domain of the anti-PSMA arm is in a monovalent configuration, meaning only one antigen-binding domain is present. Panel B depicts an anti-CD3×anti-PSMA bispecific antibody wherein the anti-PSMA binding arm is bivalent and monospecific, and the antigen-binding domain of the anti-PSMA arm is in a bivalent configuration, meaning there are two identical antigen binding domains placed in tandem. Panel C depicts an anti-CD3×anti-PSMA bispecific antibody wherein the anti-PSMA binding arm is bivalent and biparatopic, and the antigen-binding domains of the anti-PSMA arm are in a bivalent configuration.

Determination of affinity for a candidate protein can be performed using methods known in the art, such as Biacore™ measurements. Members of the antibody family may have an affinity for PSMA with a Kd of from about $10^{-6}$ to around about $10^{-11}$, including without limitation: from about $10^{-6}$ to around about $10^{-10}$; from about $10^{-6}$ to around about $10^{-9}$; from about $10^{-6}$ to around about $10^{-8}$; from about $10^{-8}$ to around about $10^{-11}$; from about $10^{-8}$ to around about $10^{-10}$; from about $10^{-8}$ to around about $10^{-9}$; from about $10^{-9}$ to around about $10^{-11}$; from about $10^{-9}$ to around about $10^{-10}$; or any value within these ranges. The affinity selection may be confirmed with a biological assessment for modulating, e.g., blocking, a PSMA biological activity, including in vitro assays, pre-clinical models, and clinical trials, as well as assessment of potential toxicity.

Members of the antibody family herein are not cross-reactive with the PSMA protein of *Cynomolgus* macaque, but can be engineered to provide cross-reactivity with the PSMA protein of *Cynomolgus* macaque, or with the PSMA of any other animal species, if desired.

The family of PSMA-specific antibodies herein comprises a VH domain, comprising CDR1, CDR2 and CDR3 sequences in a human VH framework. The CDR sequences may be situated, as an example, in the region of around amino acid residues 26-33; 51-58; and 97-116 for CDR1, CDR2 and CDR3, respectively, of the provided exemplary variable region sequences set forth in SEQ ID NOs: 24 to 58. It will be understood by one of ordinary skill in the art that the CDR sequences may be in different positions if a different framework sequence is selected, although generally the order of the sequences will remain the same.

The CDR1, CDR2, and CDR3 sequences of the anti-PSMA antibodies of the present invention may be encompassed by the following structural formulae, where an X indicates a variable amino acid, which may be the specific amino acids as indicated below.

CDR1 (SEQ ID NO: 67)
G G S I S S $X_1$ $X_2$ Y $X_3$ where $X_1$ is S or N;
$X_2$ is S or N; and
$X_3$ is Y or F; and

CDR2 (SEQ ID NO: 68)
$X_4$ $X_5$ $X_6$ S G $X_7$ T where $X_4$ is I or V;
$X_5$ is D or Y;
$X_6$ is Y or D; and
$X_7$ is Y or S; and

CDR3 (SEQ ID NO: 69)
A R H K A A T A D F D Y

The CDR1, CDR2, and CDR3 sequences of the anti-PSMA antibodies of the present invention may be encompassed by the following structural formulas, where an X indicates a variable amino acid, which may be the specific amino acids as indicated below.

CDR1 (SEQ ID NO: 70)
G F $X_1$ F $X_2$ $X_3$ Y G where $X_1$ is S or I or T;
$X_2$ is S or T or R or I; and
$X_3$ is R or S; and

CDR2 (SEQ ID NO: 71)
I $X_4$ Y D G S N $X_5$ where $X_4$ is W or S; and
$X_5$ is R or K; and

CDR3 (SEQ ID NO: 72)
A R E P R $X_6$ G Y Y Y $X_7$ $X_8$ S G Y $X_9$ S L D Y where $X_6$ is I or V;
$X_7$ is E or D;
$X_8$ is S or T; and
$X_9$ is Y or D.

Representative CDR1, CDR2 and CDR3 sequences are shown in Tables 1 and 3.

TABLE 3

Anti-PSMA heavy chain antibody CDR1, CDR2 and CDR3 amino acid sequences.

| Clone ID # | SEQ_aa_CDR1 | SEQ_aa_CDR2 | SEQ_aa_CDR3 |
| --- | --- | --- | --- |
| 325920 | GGSISSSSYY (SEQ ID NO: 1) | IDYSGYT (SEQ ID NO: 11) | ARHKAATADFDY (SEQ ID NO: 18) |
| 346181 | GGSISSSNYF (SEQ ID NO: 2) | IDYSGYT (SEQ ID NO: 11) | ARHKAATADFDY (SEQ ID NO: 18) |
| 346165 | GGSISSSSYY (SEQ ID NO: 1) | VDYSGYT (SEQ ID NO: 12) | ARHKAATADFDY (SEQ ID NO: 18) |
| 346172 | GGSISSSSYY (SEQ ID NO: 1) | IDYSGYT (SEQ ID NO: 11) | ARHKAATADFDY (SEQ ID NO: 18) |
| 326109 | GGSISSNSYY (SEQ ID NO: 3) | IYDSGST (SEQ ID NO: 13) | ARHKAATADFDY (SEQ ID NO: 18) |
| 325867 | GFSFRSYG (SEQ ID NO: 4) | IWYDGSNK (SEQ ID NO: 14) | AREPRIGYYYESSGYDSLDY (SEQ ID NO: 19) |
| 325742 | GFSFSSYG (SEQ ID NO: 5) | IWYDGSNK (SEQ ID NO: 14) | AREPRIGYYYESSGYDSLDY (SEQ ID NO: 19) |
| 325748 | GFSFSSYG (SEQ ID NO: 5) | IWYDGSNR (SEQ ID NO: 15) | AREPRIGYYYESSGYYSLDY (SEQ ID NO: 20) |
| 325940 | GFIFRSYG (SEQ ID NO: 6) | IWYDGSNK (SEQ ID NO: 14) | AREPRIGYYYESSGYYSLDY (SEQ ID NO: 20) |
| 325836 | GFSFRSYG (SEQ ID NO: 4) | IWYDGSNK (SEQ ID NO: 14) | AREPRIGYYYDSSGYDSLDY (SEQ ID NO: 21) |

TABLE 3-continued

Anti-PSMA heavy chain antibody CDR1, CDR2 and CDR3 amino acid sequences.

| Clone ID # | SEQ_aa_CDR1 | SEQ_aa_CDR2 | SEQ_aa_CDR3 |
|---|---|---|---|
| 326027 | GFSFRSYG (SEQ ID NO: 4) | IWYDGSNK (SEQ ID NO: 14) | AREPRIGYYYDSSGYDSLDY (SEQ ID NO: 21) |
| 326087 | GFIFRSYG (SEQ ID NO: 6) | IWYDGSNK (SEQ ID NO: 14) | AREPRIGYYYDSSGYDSLDY (SEQ ID NO: 21) |
| 326084 | GFSFSSYG (SEQ ID NO: 5) | IWYDGSNR (SEQ ID NO: 15) | AREPRIGYYYDSSGYYSLDY (SEQ ID NO: 22) |
| 326028 | GFSFRSYG (SEQ ID NO: 4) | ISYDGSNK (SEQ ID NO: 16) | AREPRIGYYYDSSGYDSLDY (SEQ ID NO: 21) |
| 345497 | GFSFSRYG (SEQ ID NO: 7) | IWYDGSNR (SEQ ID NO: 15) | AREPRIGYYYESSGYYSLDY (SEQ ID NO: 20) |
| 326029 | GFSFSRYG (SEQ ID NO: 7) | ISYDGSNK (SEQ ID NO: 16) | AREPRVGYYYETSGYYSLDY (SEQ ID NO: 23) |
| 345461 | GFSFTSYG (SEQ ID NO: 8) | IWYDGSNR (SEQ ID NO: 15) | AREPRIGYYYESSGYYSLDY (SEQ ID NO: 20) |
| 345493 | GFSFSRYG (SEQ ID NO: 7) | IWYDGSNR (SEQ ID NO: 15) | AREPRIGYYYESSGYYSLDY (SEQ ID NO: 20) |
| 345436 | GFSFSRYG (SEQ ID NO: 7) | IWYDGSNK (SEQ ID NO: 14) | AREPRIGYYYESSGYYSLDY (SEQ ID NO: 20) |
| 345443 | GFSFSSYG (SEQ ID NO: 5) | IWYDGSNR (SEQ ID NO: 15) | AREPRIGYYYESSGYYSLDY (SEQ ID NO: 20) |
| 345490 | GFSFSSYG (SEQ ID NO: 5) | IWYDGSNR (SEQ ID NO: 15) | AREPRIGYYYESSGYYSLDY (SEQ ID NO: 20) |
| 345482 | GFSFSSYG (SEQ ID NO: 5) | IWYDGSNR (SEQ ID NO: 15) | AREPRIGYYYESSGYYSLDY (SEQ ID NO: 20) |
| 345485 | GFSFRSYG (SEQ ID NO: 4) | IWYDGSNK (SEQ ID NO: 14) | AREPRIGYYYESSGYYSLDY (SEQ ID NO: 20) |
| 345463 | GFIFRSYG (SEQ ID NO: 6) | IWYDGSNK (SEQ ID NO: 14) | AREPRIGYYYESSGYYSLDY (SEQ ID NO: 20) |
| 325932 | GFSFSSYG (SEQ ID NO: 5) | IWYDGSNR (SEQ ID NO: 15) | AREPRIGYYYESSGYYSLDY (SEQ ID NO: 20) |
| 345505 | GFTFISYG (SEQ ID NO: 9) | IWYDGSNR (SEQ ID NO: 15) | AREPRIGYYYESSGYYSLDY (SEQ ID NO: 20) |
| 345508 | GFSFSSYG (SEQ ID NO: 5) | IWYDGSNR (SEQ ID NO: 15) | AREPRIGYYYESSGYYSLDY (SEQ ID NO: 20) |
| 345480 | GFSFSSYG (SEQ ID NO: 5) | IWYDGSNR (SEQ ID NO: 15) | AREPRIGYYYESSGYYSLDY (SEQ ID NO: 20) |
| 326116 | GFSFSRYG (SEQ ID NO: 7) | ISYDGSNK (SEQ ID NO: 16) | AREPRIGYYYDSSGYDSLDY (SEQ ID NO: 21) |
| 345509 | GFSFSSYG (SEQ ID NO: 5) | IWYDGSNK (SEQ ID NO: 14) | AREPRIGYYYESSGYYSLDY (SEQ ID NO: 20) |
| 345444 | GFTFSSYG (SEQ ID NO: 10) | IWYDGSNR (SEQ ID NO: 15) | AREPRIGYYYESSGYYSLDY (SEQ ID NO: 20) |
| 345421 | GFSFSSYG (SEQ ID NO: 5) | IWYDGSNR (SEQ ID NO: 15) | AREPRIGYYYESSGYYSLDY (SEQ ID NO: 20) |
| 345447 | GFSFSSYG (SEQ ID NO: 5) | ISYDGSNR (SEQ ID NO: 17) | AREPRIGYYYESSGYYSLDY (SEQ ID NO: 20) |
| 345510 | GFSFSSYG (SEQ ID NO: 5) | IWYDGSNK (SEQ ID NO: 14) | AREPRIGYYYESSGYYSLDY (SEQ ID NO: 20) |
| 345438 | GFSFSSYG (SEQ ID NO: 5) | IWYDGSNK (SEQ ID NO: 14) | AREPRIGYYYESSGYYSLDY (SEQ ID NO: 20) |

In some embodiments, an anti-PSMA antibody comprises a CDR1 sequence of any one of SEQ ID NOs: 1-10. In a particular embodiment, the CDR1 sequence is SEQ ID NO: 2 or 7.

In some embodiments, an anti-PSMA antibody comprises a CDR2 sequence of any one of SEQ ID NOs: 11-17. In a particular embodiment, the CDR2 sequence is SEQ ID NO: 11 or 15.

In some embodiments, an anti-PSMA antibody comprises a CDR3 sequence of any one of SEQ ID NOs: 18-23. In a particular embodiment, the CDR3 sequence is SEQ ID NO: 18 or 20.

In a further embodiment, an anti-PSMA heavy chain-only antibody comprises the CDR1 sequence of SEQ ID NO: 2; the CDR2 sequence of SEQ ID NO: 11; and the CDR3 sequence of SEQ ID NO: 18.

In a further embodiment, an anti-PSMA antibody comprises the CDR1 sequence of SEQ ID NO:7; the CDR2 sequence of SEQ ID NO: 15; and the CDR3 sequence of SEQ ID NO: 20.

In a further embodiment, an anti-PSMA antibody comprises any of the heavy chain variable region amino acid sequences of SEQ ID NOs: 24 to 58 (Table 2).

In a still further embodiment, an anti-PSMA antibody comprises the heavy chain variable region sequence of SEQ ID NO: 25.

In a still further embodiment, an anti-PSMA antibody comprises the heavy chain variable region sequence of SEQ ID NO: 38.

In some embodiments, a CDR sequence in an anti-PSMA antibody of the invention comprises one or two amino acid substitutions relative to a CDR1, CDR2 and/or CDR3 sequence or set of CDR1, CDR2 and CDR3 sequences in any one of SEQ ID NOs: 1 to 23 (Table 1).

In some embodiments, an anti-PSMA antibody preferably comprises a heavy chain variable domain (VH) in which the CDR3 sequence has greater than or equal to 80%, such as at least 85%, at least 90%, at least 95%, or at least 99% sequence identity at the amino acid level to a CDR3 sequence of any one of the antibodies whose CDR3 sequences are provided in Table 1, and binds to PSMA.

In some embodiments, an anti-PSMA antibody preferably comprises a heavy chain variable domain (VH) in which the full set of CDRs 1, 2, and 3 (combined) has greater than or equal to eighty-five percent (85%) sequence identity at the amino acid level to the CDRs 1, 2, and 3 (combined) of the antibodies whose CDR sequences are provided in Table 1, and binds to PSMA.

In some embodiments, an anti-PSMA antibody preferably comprises a heavy chain variable domain (VH) in which the full set of CDRs 1, 2, and 3 (combined) has greater than or equal to eighty-five percent (85%) sequence identity at the amino acid level to the CDRs 1, 2, and 3 (combined) of the antibodies whose CDR sequences are provided in Table 3, and binds to PSMA.

In some embodiments, an anti-PSMA antibody comprises a heavy chain variable region sequence with at least about 80% identity, at least 85% identity, at least 90% identity, at least 95% identity, at least 98% identify, or at least 99% identity to any of the heavy chain variable region sequences of SEQ ID NOs: 24 to 58 (shown in Table 2), and binds to PSMA.

In some embodiments, bispecific or multi-specific antibodies are provided, which may have any of the configurations discussed herein, including, without limitation, a bispecific three-chain antibody like molecule (TCA). In some embodiments, a multi-specific antibody can comprise at least one heavy chain variable region having binding specificity for PSMA, and at least one heavy chain variable region having binding specificity for a protein other than PSMA. In some embodiments, a multi-specific antibody can comprise a heavy chain variable region comprising at least two antigen-binding domains, wherein each of the antigen-binding domains has binding specificity for PSMA. In some embodiments, a multi-specific antibody can comprise a heavy chain/light chain pair that has binding specificity for a first antigen (e.g., CD3), and a heavy chain from a heavy chain-only antibody. In certain embodiments, the heavy chain from the heavy chain-only antibody comprises an Fc portion comprising CH2 and/or CH3 and/or CH4 domains, in the absence of a CH1 domain. In one particular embodiment, a bispecific antibody comprises a heavy chain/light chain pair that has binding specificity for an antigen on an effector cell (e.g., a CD3 protein on a T-cell), and a heavy chain from a heavy chain-only antibody comprising an antigen-binding domain that has binding specificity for PSMA.

In some embodiments, a multi-specific antibody comprises a CD3-binding VH domain that is paired with a light chain variable domain. In certain embodiments, the light chain is a fixed light chain. In some embodiments, the CD3-binding VH domain comprises a CDR1 sequence of SEQ TD NO: 59, a CDR2 sequence of SEQ ID NO: 60, and a CDR3 sequence of SEQ ID NO: 61, in a human VH framework. In some embodiments, the fixed light chain comprises a CDR1 sequence of SEQ ID NO: 62, a CDR2 sequence of SEQ ID NO: 63, and a CDR3 sequence of SEQ ID NO: 64, in a human VL framework. Together, the CD3-binding VH domain and the light chain variable domain have binding affinity for CD3. In some embodiments, a CD3-binding VH domain comprises a heavy chain variable region sequence of SEQ ID NO: 65. In some embodiments, a CD3-binding VH domain comprises a sequence having at least about 80%, at least about 85%, at least about 90%, at least about 95%, or at least about 99% percent identity to the heavy chain variable region sequence of SEQ ID NO: 65. In some embodiments, a fixed light chain comprises a light chain variable region sequence of SEQ ID NO: 66. In some embodiments, a fixed light chain comprises a sequence having at least about 80%, at least about 85%, at least about 90%, at least about 95%, or at least about 99% percent identity to the heavy chain variable region sequence of SEQ ID NO: 66.

Multi-specific antibodies comprising the above-described CD3-binding VH domain and light chain variable domain have advantageous properties, for example, as described in published PCT application publication number WO2018/052503, the disclosure of which is incorporated by reference herein in its entirety. Any of the multi-specific antibodies and antigen-binding domains described herein, having binding affinity to PSMA, can be combined with the CD3-binding domains and fixed light chain domains described herein (see, e.g., Table 4 and Table 5), as well as additional sequences, such as those provided in Table 6 and Table 7, to generate multi-specific antibodies having binding affinity to one or more PSMA epitopes, as well as CD3.

TABLE 4

Anti-CD3 Heavy and Light Chain CDR1, CDR2, CDR3 amino acid sequences.

| | SEQ_aa_CDR1 | SEQ_aa_CDR2 | SEQ_aa_CDR3 |
|---|---|---|---|
| Heavy Chain | GFTFDDYA (SEQ ID NO: 59) | ISWNSGSI (SEQ ID NO: 60) | AKDSRGYGDYRLGGAY (SEQ ID NO: 61) |
| Light Chain | QSVSSN (SEQ ID NO: 62) | GAS (SEQ ID NO: 63) | QQYNNWPWT (SEQ ID NO: 64) |

TABLE 5

Anti-CD3 heavy and light chain variable region amino acid sequences.

| | |
|---|---|
| VH | EVQLVESGGGLVQPGRSLRLSCAASGFTFDDYAMHWVRQAP GKGLEWVSGISWNSGSIGYADSVKGRFTISRDNAKNSLYLQ MNSLRAEDTALYYCAKDSRGYGDYRLGGAYWGQGTLVTSS (SEQ ID NO: 65) |
| VL | EIVMTQSPATLSVSPGERATLSCRASQSVSSNLAWYQQKPG QAPRLLIYGASTRATGIPARFSGSGSGTEFTLTISSLQSED FAVYYCQQYNNWPWTFGQGTKVEIK (SEQ ID NO: 66) |

TABLE 6

Human IgG1 and IgG4 Fc region sequences.

| | |
|---|---|
| Human IgG1 (UniProt No. P01857) | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPELLGG PSVFLFPPKPKDTLMISRTPEVTCVVVDVSHEDPEVKFNW YVDGVEVHNAKTKPREEQYNSTYRVVSVLTVLHQDWLNGK EYKCKVSNKALPAPIEKTISKAKGQPREPQVYTLPPSRDE LTKNQVSLTCLVKGFYPSDIAVEWESNGQPENNYKTTPPV LDSDGSFFLYSKLTVDKSRWQQGNVFSCSVMHEALHNHYT QKSLSLSPGK (SEQ ID NO: 75) |
| Human IgG4 (UniProt No. P01861) | ASTKGPSVFPLAPCSRSTSESTAALGCLVKDYFPEPVTVS WNSGALTSGVHTFPAVLQSSGLYSLSSVVTVPSSSLGTKT YTCNVDHKPSNTKVDKRVESKYGPPCPSCPAPEFLGGPSV FLFPPKPKDTLMISRTPEVTCVVVDVSQEDPEVQFNWYVD GVEVHNAKTKPREEQFNSTYRVVSVLTVLHQDWLNGKEYK CKVSNKGLPSSIEKTISKAKGQPREPQVYTLPPSQEEMTK NQVSLTCLVKGFYPSDIAVEWESNGQPENNYKTTPPVLDS DGSFFLYSRLTVDKSRWQEGNVFSCSVMHEALHNHYTQKS LSLSLGK (SEQ ID NO: 76) |
| Human IgG1 with silencing mutations (Fc region) | ASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDK KVEPKSCDKTHTCPPCPAPEAAGGPSVFLFPPKPKDTLMISRTPEVTCV VVDVSHEDPEVKFNWYVDGVEVHNAKTKPREEQYNSTYRVVSVLTV LHQDWLNGKEYKCKVSNKALPAPIEKTISKAKGQPREPQVYTLPPSRE EMTKNQVSLTCLVKGFYPSDIAVEWESNGQPENNYKTTPPVLDSDGS FFLYSKLTVDKSRWQQGNVFSCSVMHEALHNHYTQKSLSLSPGK (SEQ ID NO: 77) |
| Human IgG4 with silencing mutations (Fc region) | ASTKGPSVFPLAPCSRSTSESTAALGCLVKDYFPEPVTVSWNSGALTS GVHTFPAVLQSSGLYSLSSVVTVPSSSLGTKTYTCNVDHKPSNTKVDK RVESKYGPPCPPCPAPEAAGGPSVFLFPPKPKDTLMISRTPEVTCVVVD VSQEDPEVQFNWYVDGVEVHNAKTKPREEQFNSTYRVVSVLTVLHQ DWLNGKEYKCKVSNKGLPSSIEKTISKAKGQPREPQVYTLPPSQEEMT KNQVSLTCLVKGFYPSDIAVEWESNGQPENNYKTTPPVLDSDGSFFLY SRLTVDKSRWQEGNVFSCSVMHEALHNHYTQKSLSLSLGK (SEQ ID NO: 78) |

TABLE 7

| | additional sequences. |
|---|---|
| Anti-CD3 light chain constant region sequence (kappa light chain) | RTVAAPSVFIFPPSDEQLKSGTASVVCLLNNFYPREAKVQWKVDNAL<br>QSGNSQESVTEQDSKDSTYSLSSTLTLSKADYEKHKVYACEVTHQGL<br>SSPVTKSFNRGEC (SEQ ID NO: 79) |
| Anti-CD3 heavy chain sequence (VH + wt IgG1 Fc) | EVQLVESGGGLVQPGRSLRLSCAASGFTFDDYAMHWVRQAPGKGLE<br>WVSGISWNSGSIGYADSVKGRFTISRDNAKNSLYLQMNSLRAEDTAL<br>YYCAKDSRGYGDYRLGGAYWGQGTLVTVSSASTKGPSVFPLAPSSKS<br>TSGGTAALGCLVKDYFPEPVTVSWNSGALTSGVHTFPAVLQSSGLYS<br>LSSVVTVPSSSLGTQTYICNVNHKPSNTKVDKKVEPKSCDKTHTCPPC<br>PAPELLGGPSVFLFPPKPKDTLMISRTPEVTCVVVDVSHEDPEVKFNW<br>YVDGVEVHNAKTKPREEQYNSTYRVVSVLTVLHQDWLNGKEYKCK<br>VSNKALPAPIEKTISKAKGQPREPQVYTLPPSREEMTKNQVSLTCLVK<br>GFYPSDIAVEWESNGQPENNYKTTPPVLDSDGSFFLYSKLTVDKSRW<br>QQGNVFSCSVMHEALHNHYTQKSLSLSPGK (SEQ ID NO: 80) |
| Anti-CD3 heavy chain sequence (with silenced IgG1 Fc) | EVQLVESGGGLVQPGRSLRLSCAASGFTFDDYAMHWVRQAPGKGLE<br>WVSGISWNSGSIGYADSVKGRFTISRDNAKNSLYLQMNSLRAEDTAL<br>YYCAKDSRGYGDYRLGGAYWGQGTLVTVSSASTKGPSVFPLAPSSKS<br>TSGGTAALGCLVKDYFPEPVTVSWNSGALTSGVHTFPAVLQSSGLYS<br>LSSVVTVPSSSLGTQTYICNVNHKPSNTKVDKKVEPKSCDKTHTCPPC<br>PAPEAAGGPSVFLFPPKPKDTLMISRTPEVTCVVVDVSHEDPEVKFNW<br>YVDGVEVHNAKTKPREEQYNSTYRVVSVLTVLHQDWLNGKEYKCK<br>VSNKALPAPIEKTISKAKGQPREPQVYTLPPSREEMTKNQVSLTCLVK<br>GFYPSDIAVEWESNGQPENNYKTTPPVLDSDGSFFLYSKLTVDKSRW<br>QQGNVFSCSVMHEALHNHYTQKSLSLSPGK (SEQ ID NO: 81) |
| Anti-CD3 heavy chain constant region sequence (with wt IgG4 Fc) | EVQLVESGGGLVQPGRSLRLSCAASGFTFDDYAMHWVRQAPGKGLE<br>WVSGISWNSGSIGYADSVKGRFTISRDNAKNSLYLQMNSLRAEDTAL<br>YYCAKDSRGYGDYRLGGAYWGQGTLVTVSSASTKGPSVFPLAPCSRS<br>TSESTAALGCLVKDYFPEPVTVSWNSGALTSGVHTFPAVLQSSGLYSL<br>SSVVTVPSSSLGTKTYTCNVDHKPSNTKVDKRVESKYGPPCPSCPAPE<br>FLGGPSVFLFPPKPKDTLMISRTPEVTCVVVDVSQEDPEVQFNWYVDG<br>VEVHNAKTKPREEQFNSTYRVVSVLTVLHQDWLNGKEYKCKVSNKG<br>LPSSIEKTISKAKGQPREPQVYTLPPSQEEMTKNQVSLTCLVKGFYPSD<br>IAVEWESNGQPENNYKTTPPVLDSDGSFFLYSRLTVDKSRWQEGNVF<br>SCSVMHEALHNHYTQKSLSLSLGK (SEQ ID NO: 82) |
| Anti-CD3 heavy chain constant region sequence (with silenced IgG4 Fc) | EVQLVESGGGLVQPGRSLRLSCAASGFTFDDYAMHWVRQAPGKGLE<br>WVSGISWNSGSIGYADSVKGRFTISRDNAKNSLYLQMNSLRAEDTAL<br>YYCAKDSRGYGDYRLGGAYWGQGTLVTVSSASTKGPSVFPLAPCSRS<br>TSESTAALGCLVKDYFPEPVTVSWNSGALTSGVHTFPAVLQSSGLYSL<br>SSVVTVPSSSLGTKTYTCNVDHKPSNTKVDKRVESKYGPPCPPCPAPE<br>AAGGPSVFLFPPKPKDTLMISRTPEVTCVVVDVSQEDPEVQFNWYVD<br>GVEVHNAKTKPREEQFNSTYRVVSVLTVLHQDWLNGKEYKCKVSNK<br>GLPSSIEKTISKAKGQPREPQVYTLPPSQEEMTKNQVSLTCLVKGFYPS<br>DIAVEWESNGQPENNYKTTPPVLDSDGSFFLYSRLTVDKSRWQEGNV<br>FSCSVMHEALHNHYTQKSLSLSLGK (SEQ ID NO: 83) |
| Silenced IgG4 (hinge-CH2-CH3; hole (S228P, F234A, L235A; T366S, L368A, Y407V)) | ESKYGPPCPPCPAPEAAGGPSVFLFPPKPKDTLMISRTPEVTCVVVD<br>VSQEDPEVQFNWYVDGVEVHNAKTKPREEQFNSTYRVVSVLTVLHQ<br>DWLNGKEYKCKVSNKGLPSSIEKTISKAKGQPREPQVYTLPPSQEEMT<br>KNQVSLSCAVKGFYPSDIAVEWESNGQPENNYKTTPPVLDSDGSFFL<br>VSRLTVDKSRWQEGNVFSCSVMHEALHNHYTQKSLSLSLGK (SEQ ID NO: 84) |
| Silenced IgG4 (hinge-CH2-CH3; knob (S228P, F234A, L235A; T366W)) | ESKYGPPCPPCPAPEAAGGPSVFLFPPKPKDTLMISRTPEVTCVVVD<br>VSQEDPEVQFNWYVDGVEVHNAKTKPREEQFNSTYRVVSVLTVLHQ<br>DWLNGKEYKCKVSNKGLPSSIEKTISKAKGQPREPQVYTLPPSQEEMT<br>KNQVSLWCLVKGFYPSDIAVEWESNGQPENNYKTTPPVLDSDGSFF<br>LYSRLTVDKSRWQEGNVFSCSVMHEALHNHYTQKSLSLSLGK (SEQ ID NO: 85) |
| Anti-CD3 full length light chain (VL + kappa CL) | EIVMTQSPATLSVSPGERATLSCRASQSVSSNLAWYQQKPGQAPRLLI<br>YGASTRATGIPARFSGSGSGTEFTLTISSLQSEDFAVYYCQQYNNWPW<br>TFGQGTKVEIKRTVAAPSVFIFPPSDEQLKSGTASVVCLLNNFYPREAK<br>VQWKVDNALQSGNSQESVTEQDSKDSTYSLSSTLTLSKADYEKHKV<br>YACEVTHQGLSSPVTKSFNRGEC (SEQ ID NO: 86) |
| Anti-CD3 full length heavy chain (VH + silenced IgG4 Fc + knob (S228P, F234A, L235A; T366W)) | EVQLVESGGGLVQPGRSLRLSCAASGFTFDDYAMHWVRQAPGKGLE<br>WVSGISWNSGSIGYADSVKGRFTISRDNAKNSLYLQMNSLRAEDTAL<br>YYCAKDSRGYGDYRLGGAYWGQGTLVTVSSASTKGPSVFPLAPCSRS<br>TSESTAALGCLVKDYFPEPVTVSWNSGALTSGVHTFPAVLQSSGLYSL<br>SSVVTVPSSSLGTKTYTCNVDHKPSNTKVDKRVESKYGPPCPPCPAPE<br>AAGGPSVFLFPPKPKDTLMISRTPEVTCVVVDVSQEDPEVQFNWYV<br>DGVEVHNAKTKPREEQFNSTYRVVSVLTVLHQDWLNGKEYKCKVSN |

TABLE 7-continued additional sequences.

| | |
|---|---|
| | KGLPSSIEKTISKAKGQPREPQVYTLPPSQEEMTKNQVSLWCLVKGF<br>YPSDIAVEWESNGQPENNYKTTPPVLDSDGSFFLYSRLTVDKSRWQE<br>GNVFSCSVMHEALHNHYTQKSLSLSLGK (SEQ ID NO: 87) |
| PSMA monovalent<br>heavy chain (clone<br>ID 346181) +<br>silenced IgG4 Fc,<br>hole (S228P, F234A,<br>L235A, T366S,<br>L368A, Y407V | QLQLQESGPGLVKPSETLSLTCTVSGGSISSSNYFWGWIRQSPGKGLE<br>WIGSIDYSGYTYYNPSLKSRVTISVDTSKNQFSLKLSSVTAADTAVYN<br>CARHKAATADFDYRGQGTLVTVSSESKYGPPCPPCPAPEAAGGPSV<br>FLFPPKPKDTLMISRTPEVTCVVVDVSQEDPEVQFNWYVDGVEVHNA<br>KTKPREEQFNSTYRVVSVLTVLHQDWLNGKEYKCKVSNKGLPSSIEK<br>TISKAKGQPREPQVYTLPPSQEEMTKNQVSLSCAVKGFYPSDIAVEW<br>ESNGQPENNYKTTPPVLDSDGSFFLVSRLTVDKSRWQEGNVFSCSVM<br>HEALHNHYTQKSLSLSLGK (SEQ ID NO: 88) |
| PSMA bivalent<br>heavy chain (clone<br>ID 346181) +<br>silenced IgG4 Fc,<br>hole (S228P, F234A,<br>L235A, T366S,<br>L368A, Y407V | QLQLQESGPGLVKPSETLSLTCTVSGGSISSSNYFWGWIRQSPGKGLE<br>WIGSIDYSGYTYYNPSLKSRVTISVDTSKNQFSLKLSSVTAADTAVYN<br>CARHKAATADFDYRGQGTLVTVSSGGGGSGGGGSQLQLQESGPGLV<br>KPSETLSLTCTVSGGSISSSNYFWGWIRQSPGKGLEWIGSIDYSGYTYY<br>NPSLKSRVTISVDTSKNQFSLKLSSVTAADTAVYNCARHKAATADFD<br>YRGQGTLVTVSSESKYGPPCPPCPAPEAAGGPSVFLFPPKPKDTLMI<br>SRTPEVTCVVVDVSQEDPEVQFNWYVDGVEVHNAKTKPREEQFNST<br>YRVVSVLTVLHQDWLNGKEYKCKVSNKGLPSSIEKTISKAKGQPREP<br>QVYTLPPSQEEMTKNQVSLSCAVKGFYPSDIAVEWESNGQPENNYK<br>TTPPVLDSDGSFFLVSRLTVDKSRWQEGNVFSCSVMHEALHNHYTQ<br>KSLSLSLGK (SEQ ID NO: 89) |
| PSMA monovalent<br>heavy chain (clone<br>ID 345497) +<br>silenced IgG4 Fc,<br>hole (S228P, F234A,<br>L235A, T366S,<br>L368A, Y407V | QVQLVESGGGVVQPGRSLRLSCAASGFSFSRYGMHWVRQAPGKGLE<br>GVAVIWYDGSNRYYADSVKGRFTISRDNSKNTLYLQMNSLRAEDTA<br>VYYCAREPRIGYYYESSGYYSLDYRGQGTLVTVSSESKYGPPCPPCP<br>APEAAGGPSVFLFPPKPKDTLMISRTPEVTCVVVDVSQEDPEVQFNW<br>YVDGVEVHNAKTKPREEQFNSTYRVVSVLTVLHQDWLNGKEYKCK<br>VSNKGLPSSIEKTISKAKGQPREPQVYTLPPSQEEMTKNQVSLSCAVK<br>GFYPSDIAVEWESNGQPENNYKTTPPVLDSDGSFFLVSRLTVDKSRW<br>QEGNVFSCSVMHEALHNHYTQKSLSLSLGK (SEQ ID NO: 90) |
| PSMA bivalent havy<br>chain (clone ID<br>345497) + silenced<br>IgG4 Fc, hole<br>(S228P, F234A,<br>L235A, T366S,<br>L368A, Y407V | QVQLVESGGGVVQPGRSLRLSCAASGFSFSRYGMHWVRQAPGKGLE<br>GVAVIWYDGSNRYYADSVKGRFTISRDNSKNTLYLQMNSLRAEDTA<br>VYYCAREPRIGYYYESSGYYSLDYRGQGTLVTVSSGGGGSGGGGSQV<br>QLVESGGGVVQPGRSLRLSCAASGFSFSRYGMHWVRQAPGKGLEGV<br>AVIWYDGSNRYYADSVKGRFTISRDNSKNTLYLQMNSLRAEDTAVY<br>YCAREPRIGYYYESSGYYSLDYRGQGTLVTVSSESKYGPPCPPCPAPE<br>AAGGPSVFLFPPKPKDTLMISRTPEVTCVVVDVSQEDPEVQFNWYV<br>DGVEVHNAKTKPREEQFNSTYRVVSVLTVLHQDWLNGKEYKCKVSN<br>KGLPSSIEKTISKAKGQPREPQVYTLPPSQEEMTKNQVSLSCAVKGFY<br>PSDIAVEWESNGQPENNYKTTPPVLDSDGSFFLVSRLTVDKSRWQEG<br>NVFSCSVMHEALHNHYTQKSLSLSLGK (SEQ ID NO: 91) |
| PSMA bivalent havy<br>chain (clone ID<br>346181 x clone ID<br>345497) + silenced<br>IgG4 Fc, hole<br>(S228P, F234A,<br>L235A, T366S,<br>L368A, Y407V | QLQLQESGPGLVKPSETLSLTCTVSGGSISSSNYFWGWIRQSPGKGLE<br>WIGSIDYSGYTYYNPSLKSRVTISVDTSKNQFSLKLSSVTAADTAVYN<br>CARHKAATADFDYRGQGTLVTVSSGGGGSGGGGSQVQLVESGGGVV<br>QPGRSLRLSCAASGFSFSRYGMHWVRQAPGKGLEGVAVIWYDGSNR<br>YYADSVKGRFTISRDNSKNTLYLQMNSLRAEDTAVYYCAREPRIGYY<br>YESSGYYSLDYRGQGTLVTVSSESKYGPPCPPCPAPEAAGGPSVFLF<br>PPKPKDTLMISRTPEVTCVVVDVSQEDPEVQFNWYVDGVEVHNAKT<br>KPREEQFNSTYRVVSVLTVLHQDWLNGKEYKCKVSNKGLPSSIEKTIS<br>KAKGQPREPQVYTLPPSQEEMTKNQVSLSCAVKGFYPSDIAVEWES<br>NGQPENNYKTTPPVLDSDGSFFLVSRLTVDKSRWQEGNVFSCSVMH<br>EALHNHYTQKSLSLSLGK (SEQ ID NO: 92) |
| PSMA bivalent<br>heavy chain (clone<br>ID 345497 x clone<br>ID 346181) +<br>silenced IgG4 Fc,<br>hole (S228P, F234A,<br>L235A, T366S,<br>L368A, Y407V | QVQLVESGGGVVQPGRSLRLSCAASGFSFSRYGMHWVRQAPGKGLE<br>GVAVIWYDGSNRYYADSVKGRFTISRDNSKNTLYLQMNSLRAEDTA<br>VYYCAREPRIGYYYESSGYYSLDYRGQGTLVTVSSGGGGSGGGGSQL<br>QLQESGPGLVKPSETLSLTCTVSGGSISSSNYFWGWIRQSPGKGLEWIG<br>SIDYSGYTYYNPSLKSRVTISVDTSKNQFSLKLSSVTAADTAVYNCAR<br>HKAATADFDYRGQGTLVTVSSESKYGPPCPPCPAPEAAGGPSVFLF<br>PPKPKDTLMISRTPEVTCVVVDVSQEDPEVQFNWYVDGVEVHNAKT<br>KPREEQFNSTYRVVSVLTVLHQDWLNGKEYKCKVSNKGLPSSIEKTIS<br>KAKGQPREPQVYTLPPSQEEMTKNQVSLSCAVKGFYPSDIAVEWES<br>NGQPENNYKTTPPVLDSDGSFFLVSRLTVDKSRWQEGNVFSCSVMH<br>EALHNHYTQKSLSLSLGK (SEQ ID NO: 93) |

In some embodiments, bispecific or multi-specific antibodies are provided, which may have any of the configurations discussed herein, including, without limitation, a bispecific three-chain antibody like molecule (TCA). In some embodiments, a bispecific antibody can comprise at least one heavy chain variable region having binding specificity for PSMA, and at least one heavy chain variable region having binding specificity for a protein other than PSMA. In some embodiments, a bispecific antibody can comprise a heavy chain/light chain pair that has binding specificity for a first antigen, and a heavy chain from a heavy chain-only antibody, comprising an Fc portion comprising CH2 and/or CH3 and/or CH4 domains, in the absence of a CH1 domain, and an antigen binding domain that binds an epitope of a second antigen or a different epitope of the first antigen. In one particular embodiment, a bispecific antibody comprises a heavy chain/light chain pair that has binding specificity for an antigen on an effector cell (e.g., a CD3 protein on a T-cell), and a heavy chain from a heavy chain-only antibody comprising an antigen-binding domain that has binding specificity for PSMA.

In some embodiments, where an antibody of the invention is a bispecific antibody, one arm of the antibody (one binding moiety, or one binding unit) is specific for human PSMA, while the other arm may be specific for target cells, tumor-associated antigens, targeting antigens, e.g., integrins, etc., pathogen antigens, checkpoint proteins, and the like. Target cells specifically include cancer cells, including, without limitation, cells from solid tumors, e.g., prostate tumors, as discussed below. In some embodiments, one arm of the antibody (one binding moiety, or one binding unit) is specific for human PSMA, while the other arm is specific for CD3.

In some embodiments, an antibody comprises an anti-CD3 light chain polypeptide comprising the sequence of SEQ ID NO: 66 linked to the sequence of SEQ ID NO: 79, an anti-CD3 heavy chain polypeptide comprising the sequence of any one of SEQ ID NOs: 80, 81, 82, 83, 84 or 85, and an anti-PSMA heavy chain polypeptide comprising the sequence of any one of SEQ ID NOs: 24-58, in a monovalent or bivalent configuration, linked to the sequence of any one of SEQ ID NOs: 75, 76, 77, 78, 84 or 85. These sequences can be combined in various ways to produce a bispecific antibody of a desired IgG subclass, e.g., IgG1, IgG4, silenced IgG1, silenced IgG4. In one preferred embodiment, an antibody is a TCA comprising a first polypeptide comprising SEQ ID NO: 86, a second polypeptide comprising SEQ ID NO: 87, and a third polypeptide comprising SEQ ID NO: 88, 89, 90, 91, 92 or 93. In one preferred embodiment, an antibody is a TCA consisting of a first polypeptide consisting of SEQ ID NO: 86, a second polypeptide consisting of SEQ ID NO: 87, and a third polypeptide consisting of SEQ ID NO: 88, 89, 90, 91, 92 or 93.

Various formats of multi-specific antibodies are within the ambit of the invention, including, without limitation, single chain polypeptides, two chain polypeptides, three chain polypeptides, four chain polypeptides, and multiples thereof. The multi-specific antibodies herein specifically include T-cell multi-specific (e.g., bispecific) antibodies binding to PSMA and CD3 (anti-PSMAxanti-CD3 antibodies). Such antibodies induce potent T-cell mediated killing of cells expressing PSMA.

Preparation of Anti-PSMA Antibodies

The antibodies of the present invention can be prepared by methods known in the art. In a preferred embodiment, the antibodies herein are produced by transgenic animals, including transgenic mice and rats, preferably rats, in which the endogenous immunoglobulin genes are knocked out or disabled. In a preferred embodiment, the heavy chain antibodies herein are produced in UniRat™. UniRat™ have their endogenous immunoglobulin genes silenced and use a human immunoglobulin heavy-chain translocus to express a diverse, naturally optimized repertoire of fully human HCAbs. While endogenous immunoglobulin loci in rats can be knocked out or silenced using a variety of technologies, in UniRat™ the zinc-finger (endo)nuclease (ZNF) technology was used to inactivate the endogenous rat heavy chain J-locus, light chain Cκ locus and light chain Cλ locus. ZNF constructs for microinjection into oocytes can produce IgH and IgL knock out (KO) lines. For details see, e.g., Geurts et al., 2009, *Science* 325:433. Characterization of Ig heavy chain knockout rats has been reported by Menoret et al., 2010, *Eur. J. Immunol.* 40:2932-2941. Advantages of the ZNF technology are that non-homologous end joining to silence a gene or locus via deletions up to several kb can also provide a target site for homologous integration (Cui et al., 2011, *Nat Biotechnol* 29:64-67). Human heavy chain antibodies produced in UniRat™ are called UniAbs™ and can bind epitopes that cannot be attacked with conventional antibodies. Their high specificity, affinity, and small size make them ideal for mono- and poly-specific applications.

In addition to UniAbs™, specifically included herein are heavy chain-only antibodies lacking the camelid VHH framework and mutations, and their functional VH regions. Such heavy chain-only antibodies can, for example, be produced in transgenic rats or mice which comprise fully human heavy chain-only gene loci as described, e.g., in WO2006/008548, but other transgenic mammals, such as rabbit, guinea pig, rat can also be used, rats and mice being preferred. Heavy chain-only antibodies, including their VHH or VH functional fragments, can also be produced by recombinant DNA technology, by expression of the encoding nucleic acid in a suitable eukaryotic or prokaryotic host, including, for example, mammalian cells (e.g., CHO cells), *E. coli* or yeast.

Domains of heavy chain-only antibodies combine advantages of antibodies and small molecule drugs: can be mono- or multi-valent; have low toxicity; and are cost-effective to manufacture. Due to their small size, these domains are easy to administer, including oral or topical administration, are characterized by high stability, including gastrointestinal stability; and their half-life can be tailored to the desired use or indication. In addition, VH and VHH domains of HCAbs can be manufactured in a cost-effective manner.

In a particular embodiment, the heavy chain antibodies of the present invention, including UniAbs™, have the native amino acid residue at the first position of the FR4 region (amino acid position 101 according to the Kabat numbering system), substituted by another amino acid residue, which is capable of disrupting a surface-exposed hydrophobic patch comprising or associated with the native amino acid residue at that position. Such hydrophobic patches are normally buried in the interface with the antibody light chain constant region but become surface exposed in HCAbs and are, at least partially, for the unwanted aggregation and light chain association of HCAbs. The substituted amino acid residue preferably is charged, and more preferably is positively charged, such as lysine (Lys, K), arginine (Arg, R) or histidine (His, H), preferably arginine (R). In a preferred embodiment the heavy chain-only antibodies derived from the transgenic animals contain a Trp to Arg mutation at position 101. The resultant HCAbs preferably have high antigen-binding affinity and solubility under physiological conditions in the absence of aggregation.

As part of the present invention, human IgG anti-PSMA heavy chain antibodies with unique sequences from UniRat™ animals (UniAb™) were identified that bind to human PSMA in ELISA protein and cell-binding assays. The identified heavy chain variable region (VH) sequences are positive for human PSMA protein binding and/or for binding to PSMA+cells, and are all negative for binding to cells that do not express PSMA. See, e.g., Table 8.

Heavy chain antibodies binding to non-overlapping epitopes on a PSMA protein, e.g., UniAbs™ can be identified by competition binding assays, such as enzyme-linked immunoassays (ELISA assays) or flow cytometric competitive binding assays. For example, one can use competition between known antibodies binding to the target antigen and the antibody of interest. By using this approach, one can divide a set of antibodies into those that compete with the reference antibody and those that do not. The non-competing antibodies are identified as binding to a distinct epitope that does not overlap with the epitope bound by the reference antibody. Often, one antibody is immobilized, the antigen is bound, and a second, labeled (e.g., biotinylated) antibody is tested in an ELISA assay for ability to bind the captured antigen. This can be performed also by using surface plasmon resonance (SPR) platforms, including ProteOn™ XPR36 (BioRad, Inc), Biacore™ 2000 and Biacore™ T200 (GE Healthcare Life Sciences), and MX96 SPR imager (Ibis technologies B.V.), as well as on biolayer interferometry platforms, such as Octet® RED384 and Octet® HTX (ForteBio, Pall Inc). For further details see the examples herein.

Typically, an antibody "competes" with a reference antibody if it causes about 15-100% reduction in the binding of the reference antibody to the target antigen, as determined by standard techniques, such as by the competition binding assays described above. In various embodiments, the relative inhibition is at least about 15%, at least about 20%, at least about 25%, at least about 30%, at least about 35%, at least about 40%, at least about 45%, at least about 50% at least about 55%, at least about 60%, at least about 65%, at least about 70%, at least about 75%, at least about 80%, at least about 85%, at least about 90%, at least about 95% or higher.

Pharmaceutical Compositions, Uses and Methods of Treatment

It is another aspect of the present invention to provide pharmaceutical compositions comprising one or more antibodies of the present invention in admixture with a suitable pharmaceutically acceptable carrier. Pharmaceutically acceptable carriers as used herein are exemplified, but not limited to, adjuvants, solid carriers, water, buffers, or other carriers used in the art to hold therapeutic components, or combinations thereof.

In one embodiment, a pharmaceutical composition comprises a heavy chain antibody (e.g., UniAb™) that binds to PSMA. In another embodiment, a pharmaceutical composition comprises a multi-specific (including bispecific) heavy chain antibody (e.g., UniAb™) with binding specificity for two or more non-overlapping epitopes on a PSMA protein. In a preferred embodiment, a pharmaceutical composition comprises a multi-specific (including bispecific and TCA) heavy chain antibody (e.g., UniAb™) with binding specificity to PSMA and with binding specificity to a binding target on an effector cell (e.g., a binding target on a T-cell, such as, e.g., a CD3 protein on a T-cell).

Pharmaceutical compositions of the antibodies used in accordance with the present invention are prepared for storage by mixing proteins having the desired degree of purity with optional pharmaceutically acceptable carriers, excipients or stabilizers (see, e.g. *Remington's Pharmaceutical Sciences* 16th edition, Osol, A. Ed. (1980)), such as in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Pharmaceutical compositions for parenteral administration are preferably sterile and substantially isotonic and manufactured under Good Manufacturing Practice (GMP) conditions. Pharmaceutical compositions can be provided in unit dosage form (i.e., the dosage for a single administration). The formulation depends on the route of administration chosen. The antibodies herein can be administered by intravenous injection or infusion or subcutaneously. For injection administration, the antibodies herein can be formulated in aqueous solutions, preferably in physiologically-compatible buffers to reduce discomfort at the site of injection. The solution can contain carriers, excipients, or stabilizers as discussed above. Alternatively, antibodies can be in lyophilized form for constitution with a suitable vehicle, e.g., sterile pyrogen-free water, before use.

Antibody formulations are disclosed, for example, in U.S. Pat. No. 9,034,324. Similar formulations can be used for the heavy chain antibodies, including UniAbs™, of the present invention. Subcutaneous antibody formulations are described, for example, in US20160355591 and US20160166689.

Methods of Use

The anti-PSMA antibodies and pharmaceutical compositions described herein can be used for the treatment of diseases and conditions characterized by the expression of PSMA, including, without limitation, the conditions and diseases described further herein.

PSMA is a type II transmembrane protein that is expressed on prostate epithelium tissue and is upregulated in prostate cancer and the neovasculature of solid tumors. It is also expressed at low levels in healthy tissues such as the brain, kidney, and salivary glands but its overexpression in malignant prostate tissue makes it an attractive target for the therapeutic treatment of prostate cancer. It may also be relevant for therapy or imaging of solid tumors, given its high expression in malignant neovasculature. Monoclonal antibodies, antibody drug conjugates and chimeric antigen receptor T-cells targeting PSMA have been described for treatment of metastatic prostate cancer (Hemandez-Hoyos et al., 2016, PMID: 27406985, DiPippo et al., 2014, PMID: 25327986, Serganova et al., 2016, PMID: 28345023). In addition, radionuclide conjugates specific to PSMA are being investigated for imaging and treatment of prostate cancer (e.g., Hofman et al., 2018 PMID: 29752180).

In one aspect, the anti-PSMA antibodies (e.g., UniAbs™) and pharmaceutical compositions herein can be used to treat disorders characterized by the expression of PSMA, including, without limitation, prostate cancer and solid tumors.

Effective doses of the compositions of the present invention for the treatment of disease vary depending upon many different factors, including means of administration, target site, physiological state of the patient, whether the patient is human or an animal, other medications administered, and whether treatment is prophylactic or therapeutic. Usually, the patient is a human, but nonhuman mammals may also be treated, e.g., companion animals such as dogs, cats, horses, etc., laboratory mammals such as rabbits, mice, rats, etc., and the like. Treatment dosages can be titrated to optimize safety and efficacy.

Dosage levels can be readily determined by the ordinarily skilled clinician, and can be modified as required, e.g., as required to modify a subject's response to therapy. The amount of active ingredient that can be combined with the carrier materials to produce a single dosage form varies depending upon the host treated and the particular mode of administration. Dosage unit forms generally contain between from about 1 mg to about 500 mg of an active ingredient.

In some embodiments, the therapeutic dosage the agent may range from about 0.0001 to 100 mg/kg, and more usually 0.01 to 5 mg/kg, of the host body weight. For example, dosages can be 1 mg/kg body weight or 10 mg/kg body weight or within the range of 1-10 mg/kg. An exemplary treatment regime entails administration once every two weeks or once a month or once every 3 to 6 months. Therapeutic entities of the present invention are usually administered on multiple occasions. Intervals between single dosages can be weekly, monthly or yearly. Intervals can also be irregular as indicated by measuring blood levels of the therapeutic entity in the patient. Alternatively, therapeutic entities of the present invention can be administered as a sustained release formulation, in which case less frequent administration is required. Dosage and frequency vary depending on the half-life of the polypeptide in the patient.

Typically, compositions are prepared as injectables, either as liquid solutions or suspensions; solid forms suitable for solution in, or suspension in, liquid vehicles prior to injection can also be prepared. The pharmaceutical compositions herein are suitable for intravenous or subcutaneous administration, directly or after reconstitution of solid (e.g., lyophilized) compositions. The preparation also can be emulsified or encapsulated in liposomes or micro particles such as polylactide, polyglycolide, or copolymer for enhanced adjuvant effect, as discussed above. Langer, *Science* 249: 1527, 1990 and Hanes, *Advanced Drug Delivery Reviews* 28: 97-119, 1997. The agents of this invention can be administered in the form of a depot injection or implant preparation which can be formulated in such a manner as to permit a sustained or pulsatile release of the active ingredient. The pharmaceutical compositions are generally formulated as sterile, substantially isotonic and in full compliance with all Good Manufacturing Practice (GMP) regulations of the U.S. Food and Drug Administration.

Toxicity of the antibodies and antibody structures described herein can be determined by standard pharmaceutical procedures in cell cultures or experimental animals. e.g., by determining the LD50 (the dose lethal to 50% of the population) or the LD100 (the dose lethal to 100% of the population). The dose ratio between toxic and therapeutic effect is the therapeutic index. The data obtained from these cell culture assays and animal studies can be used in formulating a dosage range that is not toxic for use in humans. The dosage of the antibodies described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the patient's condition.

The compositions for administration will commonly comprise an antibody or other ablative agent dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, e.g., sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs (e.g., *Remington's Pharmaceutical Science* (15th ed., 1980) and Goodman & Gillman, *The Pharmacological Basis of Therapeutics* (Hardman et al., eds., 1996)).

Also within the scope of the invention are kits comprising the active agents and formulations thereof, of the invention and instructions for use. The kit can further contain a least one additional reagent, e.g. a chemotherapeutic drug, etc. Kits typically include a label indicating the intended use of the contents of the kit. The term "label" as used herein includes any writing, or recorded material supplied on or with a kit, or which otherwise accompanies a kit.

The invention now being fully described, it will be apparent to one of ordinary skill in the art that various changes and modifications can be made without departing from the spirit or scope of the invention.

EXAMPLES

Materials and Methods

Example 1: UniRat™ Immunization with Recombinant Human PSMA

Twelve UniRat™ animals were immunized with recombinant human PSMA protein fused to a his tag (R&D Systems Cat No.: 4234-ZN). The animals were immunized twice per week for eight weeks. After a 35-day immunization time course, serum was collected from the rats to determine serum titers.

Serum Titer Results

Figure 1B:
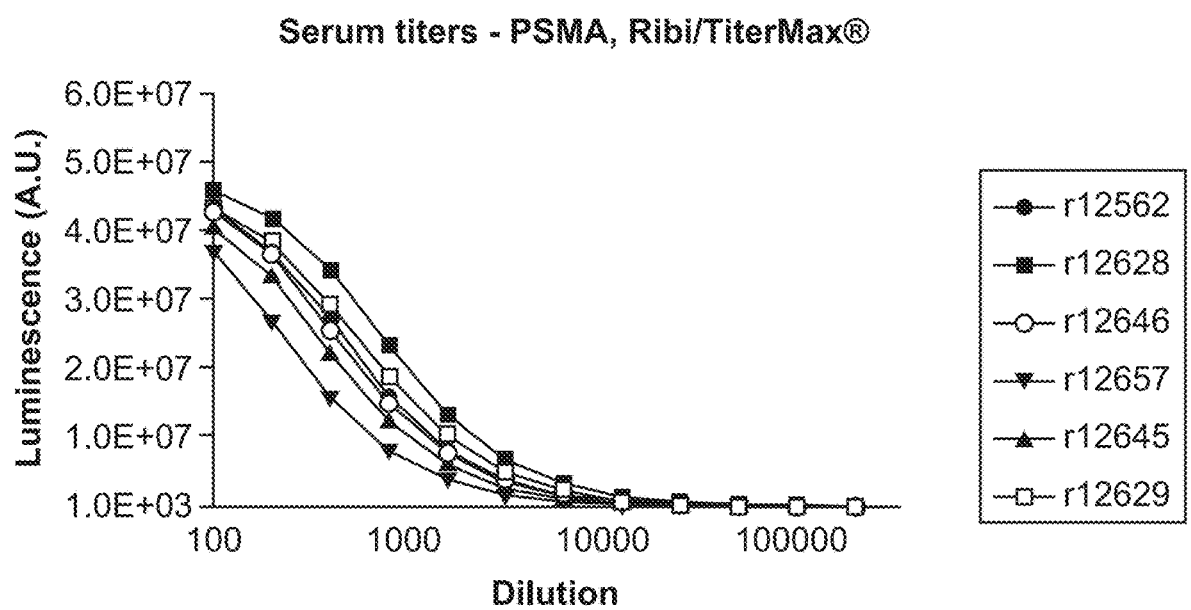

Serum titer summary information is shown in FIG. 1, panels A-B. In the graphs depicted in FIG. 1, panels A-B, each line represents an individual animal. The legends of the graphs show the ID number of each individual animal. Binding activity for a 12-point dilution series of serum was tested by ELISA against a huPSMA+His tag protein and a His tag off-target protein. Among this group of animals, a range of serum reactivity levels to human PSMA protein was observed. No serum response to the His tag off-target protein was observed.

Example 2: Flow Cytometry Analysis of Binding to PSMA Positive and Negative Cells by Anti-PSMA UniAbs™

Binding to PSMA-positive cells was assessed by flow cytometry (Guava® easy Cyte™ 8HT, EMD Millipore) using the LNCaP cell line (ATCC®: CRL-1740), 22Rv1 cell line (ATCC® CRL-2505), a PC3 cell line (ATCC® CRL-1435) stably transfected to express human PSMA, or the DU-145 cell line (ATCC® HTB-81). Briefly, 50,000 target cells were stained with a dilution series of purified Uni-Abs™ for 30 minutes at 4° C. Following incubation, the cells were washed twice with flow cytometry buffer (IX PBS, 1% BSA, 0.1% $NaN_3$) and stained with goat $F(ab')_2$ anti-human IgG conjugated to R-phycoerythrin (PE) (Southern Biotech, cat. #2042-09) to detect cell-bound antibodies. After a 20-minute incubation at 4° C., the cells were washed twice with flow cytometry buffer and the mean fluorescence intensity (MFI) was measured by flow cytometry. The MFI of cells stained with secondary antibody alone were used for determination of background signal and binding of each antibody was converted to fold over background. Binding to cynomolgus PSMA positive cells was determined using the same protocol with the following modifications: the target cells were from Freestyle™ 293-F cells (ThermoFisher R79007) transiently transfected to express the extracellular domain of cynomolgus PSMA. In some experiments EC50 values were calculated using GraphPad Prism 7.

Table 8 summarizes target binding activity of several of the anti-PSMA heavy-chain antibodies (HCAb) described herein. Column 1 indicates the clone ID of the HCAb. Column 2 indicates binding to LNCaP cells measured as fold over the background MFI signal.

TABLE 8

Binding to PSMA-expressing cell line

| Column 1: CLONE_ID | Column 2: LNCaP |
|---|---|
| 325920 | 282 |
| 346181 | 264 |
| 346165 | 243 |
| 346172 | 216 |
| 326109 | 25 |
| 325867 | 210 |
| 325742 | 200 |
| 325748 | 193 |
| 325940 | 169 |
| 325836 | 163 |
| 326027 | 138 |
| 326087 | 129 |
| 326084 | 125 |
| 326028 | 117 |
| 345497 | 112 |
| 326029 | 109 |
| 345461 | 102 |
| 345493 | 101 |
| 345436 | 87 |
| 345443 | 84 |
| 345490 | 80 |
| 345482 | 80 |
| 345485 | 71 |
| 345463 | 68 |
| 325932 | 64 |
| 345505 | 59 |
| 345508 | 55 |
| 345480 | 47 |
| 326116 | 38 |
| 345509 | 37 |
| 345444 | 23 |

TABLE 8-continued

Binding to PSMA-expressing cell line

| Column 1: CLONE_ID | Column 2: LNCaP |
|---|---|
| 345421 | 22 |
| 345447 | 14 |
| 345510 | 13 |
| 345438 | 13 |

Figure 2A:
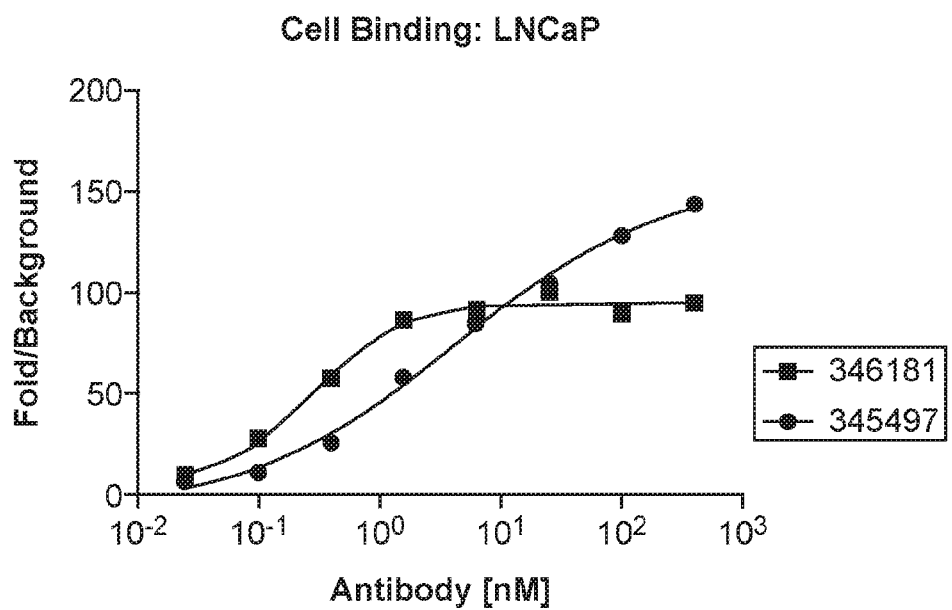
FIG. 2, panel A is a graph showing cell binding to human PSMA.
Figure 2B:
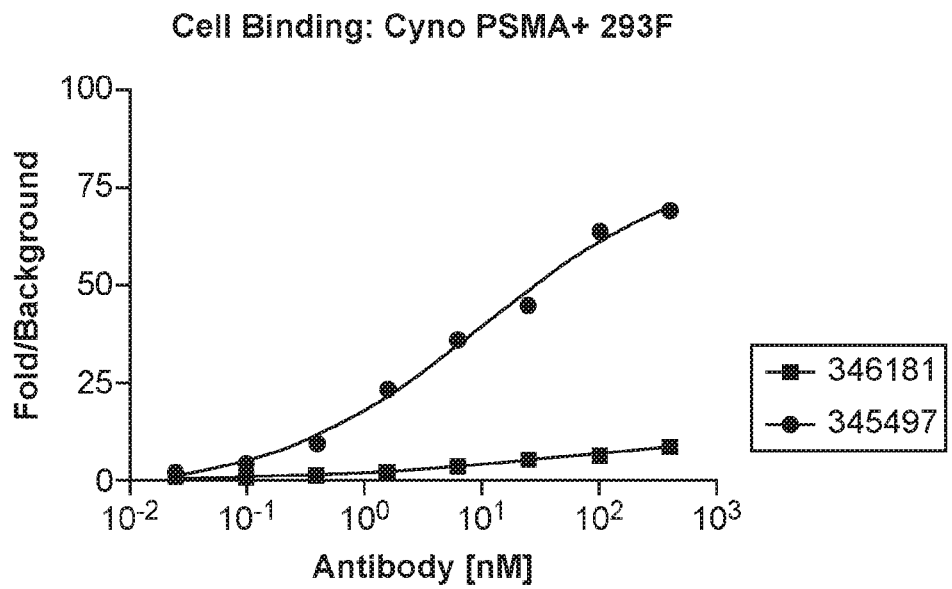

The differences in binding to cynomolgus PSMA, as shown in FIG. 2, panels A and B, supports the difference in human PSMA epitope recognized by HCAbs 346181 and 345497.

Example 3: Recombinant Protein Binding by Biolayer Interferometry (BLI)

Figure 3:
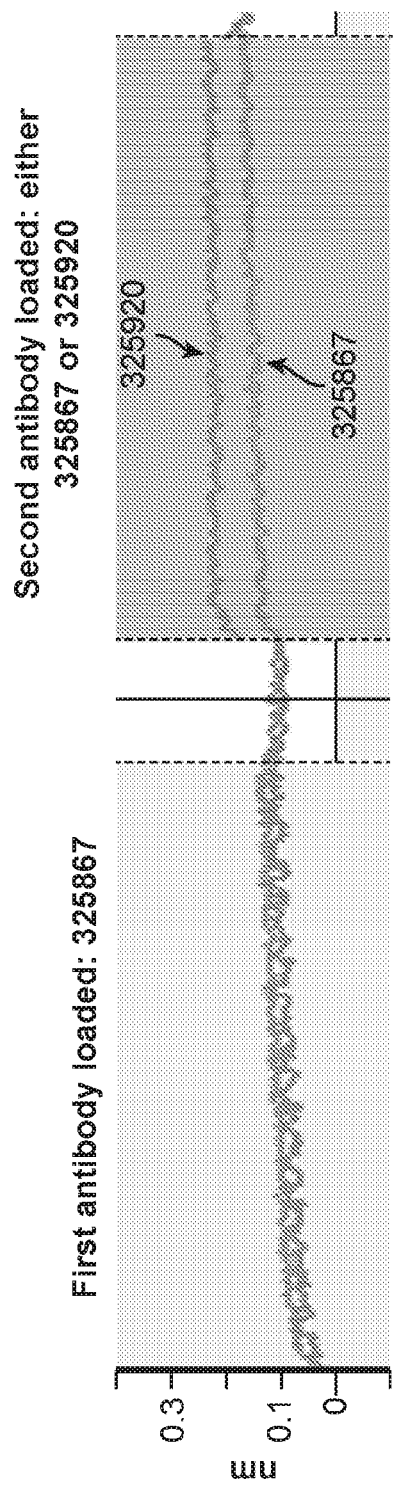
FIG. 3 is a graph showing binding competition between two antibody families in accordance with an embodiment of the invention.

Using Biolayer interferometry, binding competition was assessed between the two antibody families of which clone ID 345497 and clone ID 346181 are members. Antigen-antibody epitope binning analysis was performed on the Octet® QK-384 (ForteBio). Briefly, anti-Penta HIS Capture (HIS 1K) sensors were used to immobilize the antigen—recombinant human PSMA (R&D Systems Cat No.: 4234-ZN) for 120 seconds. After baseline readings, sensors were dipped into solutions containing Antibody 1 (325867) for 300 seconds and another baseline was set for 60 secs. Then sensors were dipped into wells containing either Antibody 1 as a positive control for blocking or Antibody 2 (325920). Association and dissociation rates were measured for 300 and 600 seconds, respectively. Data analysis was performed with Octet® Data Analysis I-IT vii 0.0 (ForteBio). As shown in FIG. 3, 325920 bound the PSMA protein pre-bound with the 325867 antibody, informing that these two antibodies recognize non-overlapping epitopes on PSMA. The shift in binding signal is reported in nanometers.

Example 4: Composition of Biparatopic and Bivalent Anti-PSMA Antibodies

As shown in Table 9, clone ID 350123 is composed of clone ID 346181 sequence linked to clone ID 345497 sequence with the bridging sequence GGGGSGGGGS (SEQ ID NO: 74). Clone ID 350122 is composed of two repeats of clone ID 346181 joined by the same linker sequence. Clone ID 350123 is biparatopic as it is composed of two anti-PSMA domains recognizing different epitopes on PSMA. Clone ID 350122 is bivalent but not biparatopic, as it is composed of the same anti-PSMA domain in tandem. Schematic illustrations of various anti-PSMA×anti-CD3 antibodies are depicted in FIG. 5, panels A-C.

TABLE 9

Description of amino acid sequence of biparatopic and bivalent anti-PSMA antibodies

| Clone ID | Sequence 1 | Linker sequence | Sequence 2 |
|---|---|---|---|
| 350123 | 346181 | GGGGSGGGGS (SEQ ID NO: 74) | 345497 |
| 350122 | 346181 | GGGGSGGGGS (SEQ ID NO: 74) | 346181 |

Example 5: Determination of Affinity to Cell Surface Expressed Human PSMA

PSMA cell surface affinity was determined by Scatchard analysis using the human prostate carcinoma cell line 22Rv1. First, PSMAxCD3 multi-specific antibodies were labeled with Alexa Fluor™ 488 using the Alexa Fluor™ 488 5-SDP Ester kit (ThermoFisher A30052). Binding to 22Rv1s was then assessed by flow cytometry (Guava® easyCyte™ 8HT, EMD Millipore). Briefly, 100,000 target cells were stained with a dilution series of Alexa Fluor™ 488 labeled multi-specific antibodies for 1 hour at 4° C. Following incubation, the cells were washed twice with flow cytometry buffer and the mean fluorescence intensity was measured by flow cytometry.

To establish a standard curve for the calculation of molecules of equivalent soluble fluorophores (MESF), Bangs Lab Quantum Alexa Fluor™ 488 MESF bead populations 1 through 4 were combined into a single tube and run on the Guava® easyCyte™ 8HT. Blank beads were analyzed in a separate tube. The MFI of each bead population was measured for the FITC-channel. A linear regression of Log10(MFI) against Log10(MESF) was plotted using GraphPad Prism 7.

Figure 4A:
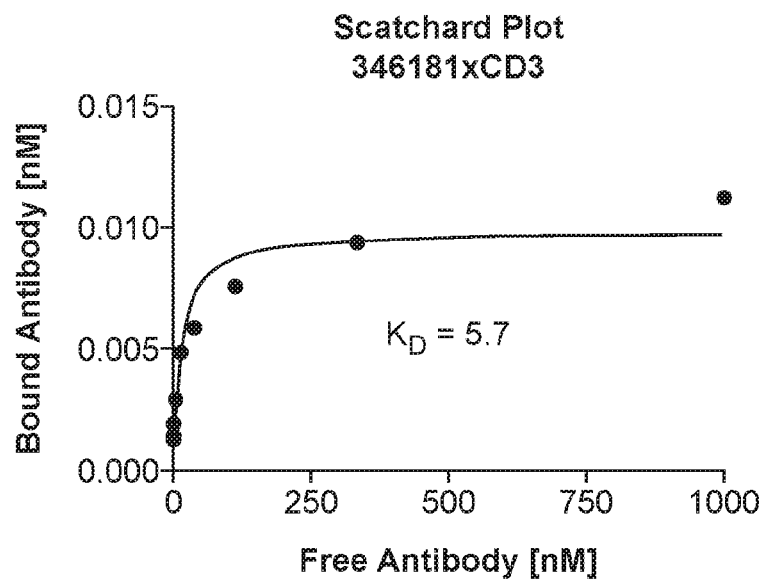
FIG. 4, panel A is a Scatchard plot showing binding affinity to cell surface expressed PSMA of a bispecific antibody having binding affinity to CD3 and PSMA, wherein the PSMA arm is monoparatopic and monovalent according to an embodiment of the invention.
Figure 4B:
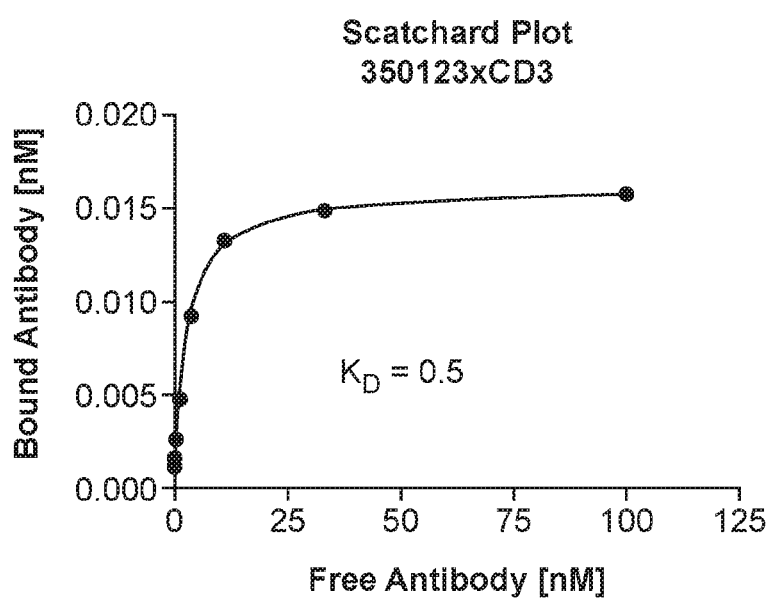

The MFI of each experimental sample was interpolated on the calibration curve and MESF was determined for each sample. Subsequently, the average number of antibodies bound per cell (ABC) was calculated by dividing the average MESF by the degree of labeling (DOL) of the antibody. The number of ABC was multiplied by the cell concentration to determine total concentration of bound antibody. The free antibody concentration was calculated by subtracting the bound antibody concentration from the staining concentration (starting dose). Free antibody concentration was plotted against bound antibody concentration in GraphPad Prism 7. The resulting plot was fitted to a non-linear regression, one-site specific binding function to determine affinity, as shown in FIG. 4, panels A and B.

Example 6: Multi-Specific Antibody Mediated Killing of PSMA Positive Prostate Tumor Cells Through T-Cell Redirection

Assays Using Resting T-Cells

Target cells were seeded at 15.000 cells per well in a 96-well plate and grown overnight at 37° C. Following incubation, increasing amounts of multi-specific antibody were added together with resting human T-cells at a 10:1 effector to target cell ratio and incubated for an additional 48 or 72 hours at 37° C. (48 hours for assays with LNCaP, MDA-PCa-2b and PC3-PSMA cells and 72 hours for assays with 22Rv1 cells). Cell death was measured using either the cell proliferation reagent WST-1 (Sigma Cat No.: 11644807001) or flow cytometry. In some experiments, a small sample of each supernatant was collected after incubation but prior to analysis of target cell viability and saved for analysis of cytokine production. When cell viability was analyzed with WST-1 reagent, the reagent stock was added to each well at a 1:10 dilution and incubated for 90 minutes at 37° C. The absorbance was then measured at 450 nm (reference 690 nm), and the percent specific lysis was calculated.

If target cell viability was analyzed by flow cytometry, then the target cells were labeled before initiating the assay with the membrane dye DiR (ThermoFisher D12731). After incubation with T-cells and antibody, the supernatants were either saved for cytokine analysis or disposed of. Wells were then washed once to collect dead tumor cells and T-cells, which were transferred to a flow cytometry plate. The remaining attached tumor cells were trypsinized and then added to the corresponding wells in the flow cytometry plate. Annexin-V reagent was used to stain dead cells and flow cytometry was conducted (BD FACSCelesta™) to quantitate the percent of dead tumor cells in each sample, gated by DiR staining. Wells containing untreated target cells were used to normalize for spontaneous cell death. In some experiments, a negative control antibody was used, consisting of the same CD3-targeting arm as in the PSMAxCD3 multi-specific molecules, but replacing the tumor-targeting arm with a VH specific to the HIV protein gp120.

Figure 7:
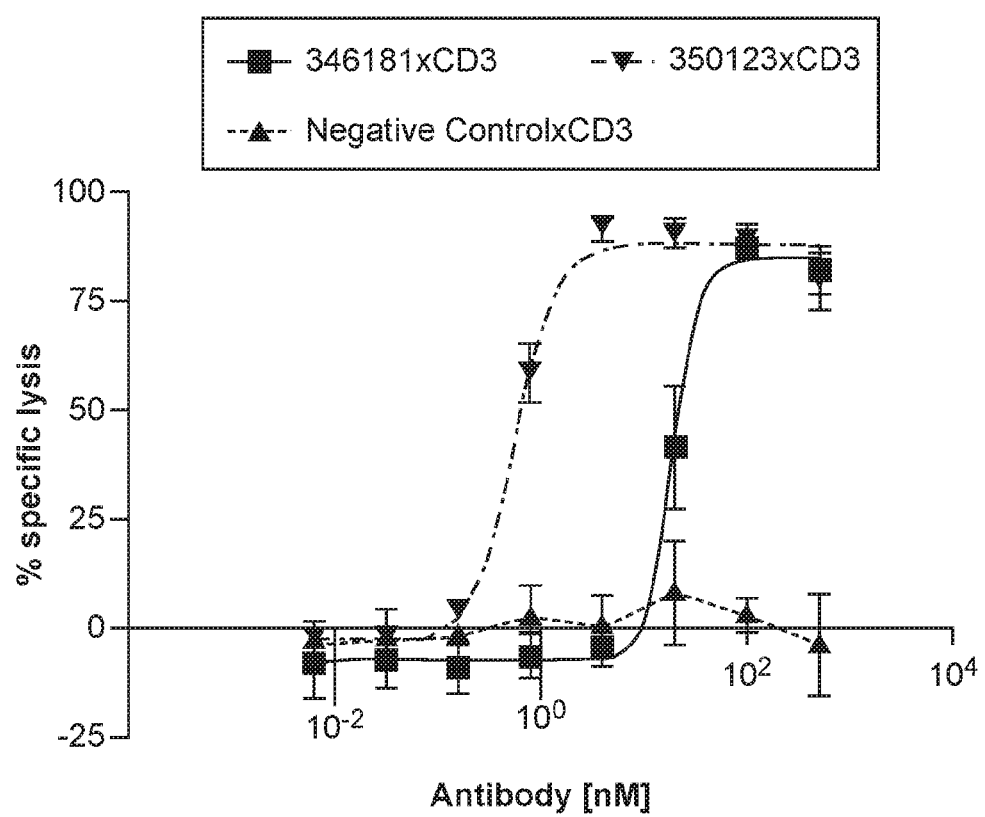
FIG. 7 is a graph depicting T-cell mediated lysis of PSMA positive cells using unstimulated T-cells.

FIG. 7 shows T-cell mediated lysis of PSMA positive cells using unstimulated T-cells. Unstimulated human T-cells were incubated with PSMA-expressing cells (LNCaP) and different concentrations of multi-specific antibodies. The biparatopic anti-PSMAxCD3 antibody (350123xCD3) outperformed the monoparatopic PSMAxCD3 antibody (346181xCD3).

Assays Using Pre-Activated T-Cells

Human pan T-cells were pre-activated with plate-bound OKT3 and IL-2 for three days, followed by an additional day of incubation in fresh IL-2. Target cells were trypsinized, loaded with Calcein-AM (ThermoFisher C3100MP), mixed with activated T-cells to an E:T ratio of 20:1, and added to the wells of a 96-well plate. Dilution series of different multi-specific antibodies were added, followed by incubation for 4 hours at 37° C. Supernatants were then transferred to black 96-well plates and absorbance was measured at 480 nm/520 nm ex/em to quantify release of calcein. Target cells incubated without T-cells were used to normalize for spontaneous calcein release of intact tumor cells. Addition of 2% Triton™-X to control wells containing target cells allowed for calculation of the calcein signal corresponding to maximum cell lysis. Using this value, each experimental well was reported as percent of maximum cell lysis. Data analysis was conducted using GraphPad prism 7.

Figure 6:
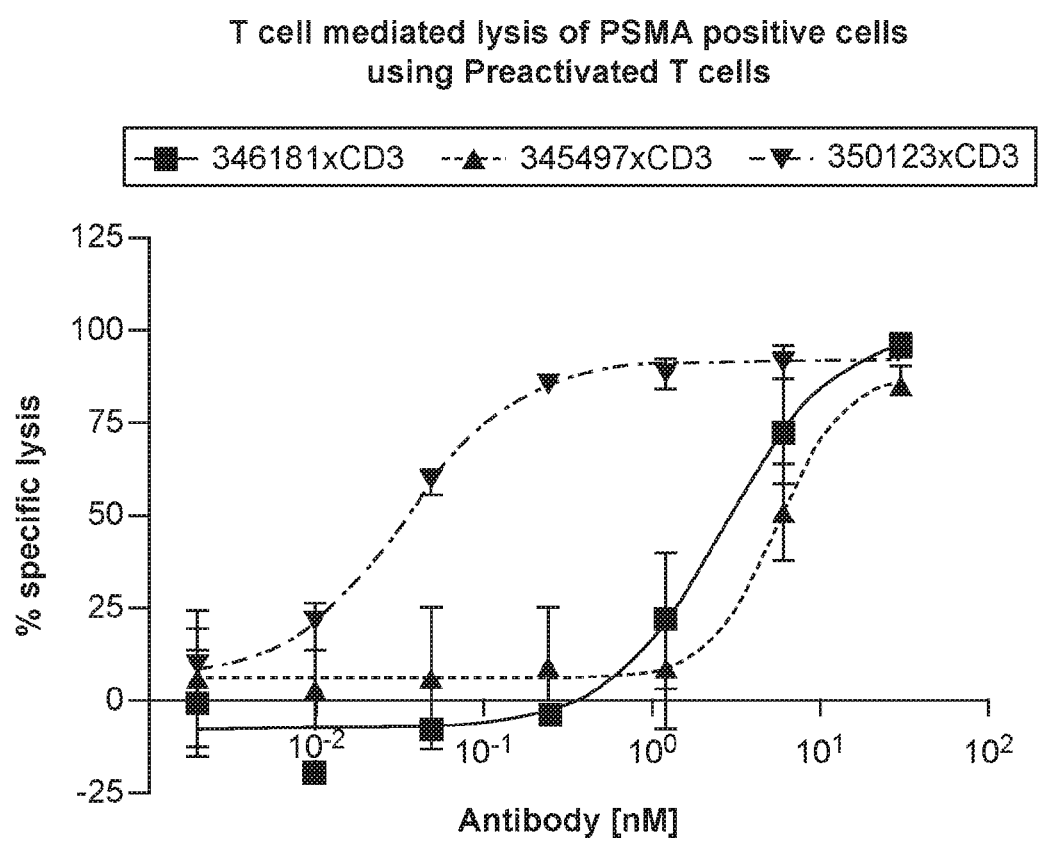
FIG. 6 is a graph depicting T-cell mediated lysis of PSMA positive cells using pre-activated T-cells.

FIG. 6 shows T-cell mediated lysis of PSMA positive cells using pre-activated T-cells. Pre-activated human T-cells were incubated with human PSMA-expressing cells (LNCaP) and different concentrations of multi-specific antibodies. Tumor cell death was measured by calcein release and normalized to spontaneous release of tumor cells in the absence of T-cells. The biparatopic anti-PSMAxCD3 antibody (350123xCD3) outperformed both monoparatopic PSMAxCD3 antibodies.

Figure 8:
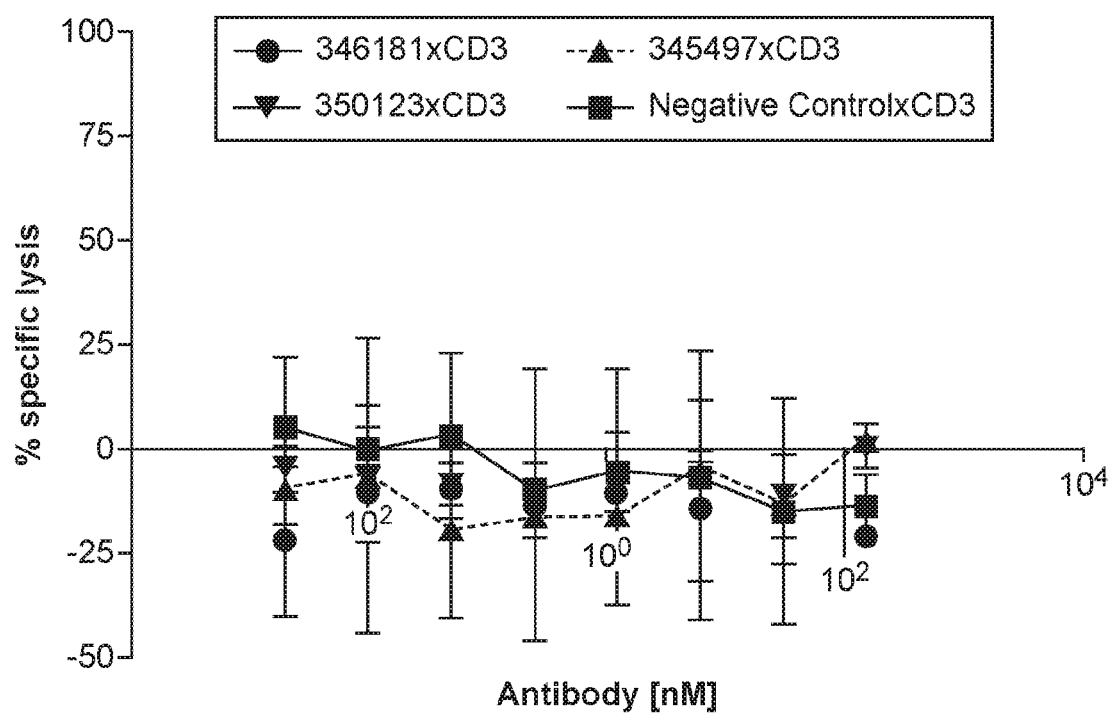
FIG. 8 is a graph depicting percent specific lysis of PSMA negative DU145 cells as a function of multi-specific antibody concentration in the presence of pre-activated T-cells.

FIG. 8 shows that multi-specific antibodies do not lyse PSMA-negative cells. Pre-activated human T-cells were incubated with PSMA-negative prostate cancer cells (DU145) and different concentrations of multi-specific antibodies. No lysis of these cells occurred by any of the antibodies tested.

Figure 9:
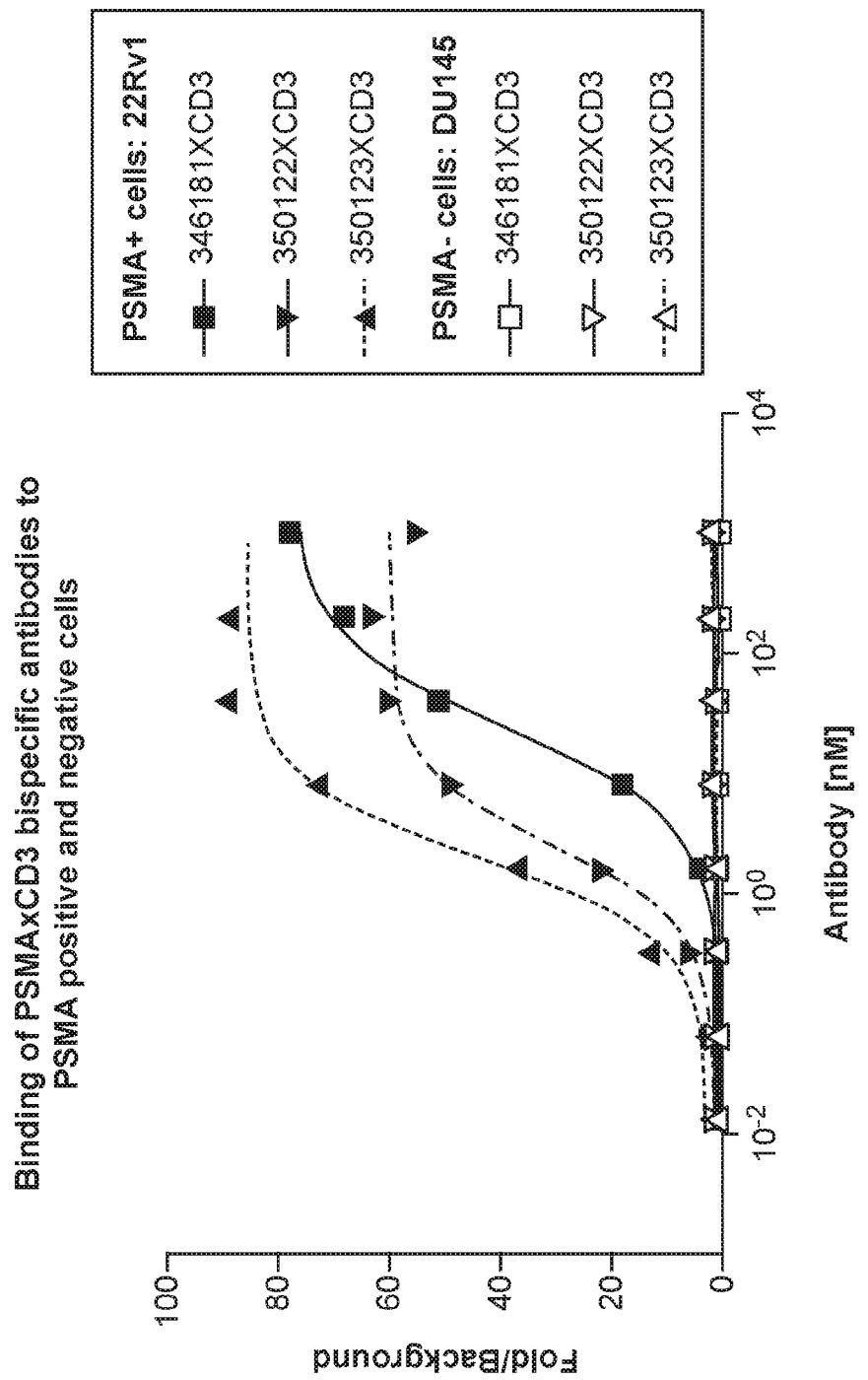
FIG. 9 is a graph showing binding of PSMAxCD3 bispecific antibodies to PSMA positive and negative cells.

FIG. 9 shows binding of PSMAxCD3 multi-specific antibodies to PSMA positive and negative cells. Multi-specific anti-PSMAxanti-CD3 antibodies show binding to PSMA positive prostate tumor cells (22Rv1), but no binding to PSMA negative prostate tumor cells (DU145). The biparatopic molecule (350123) showed the strongest on-target cell binding.

Figure 10:
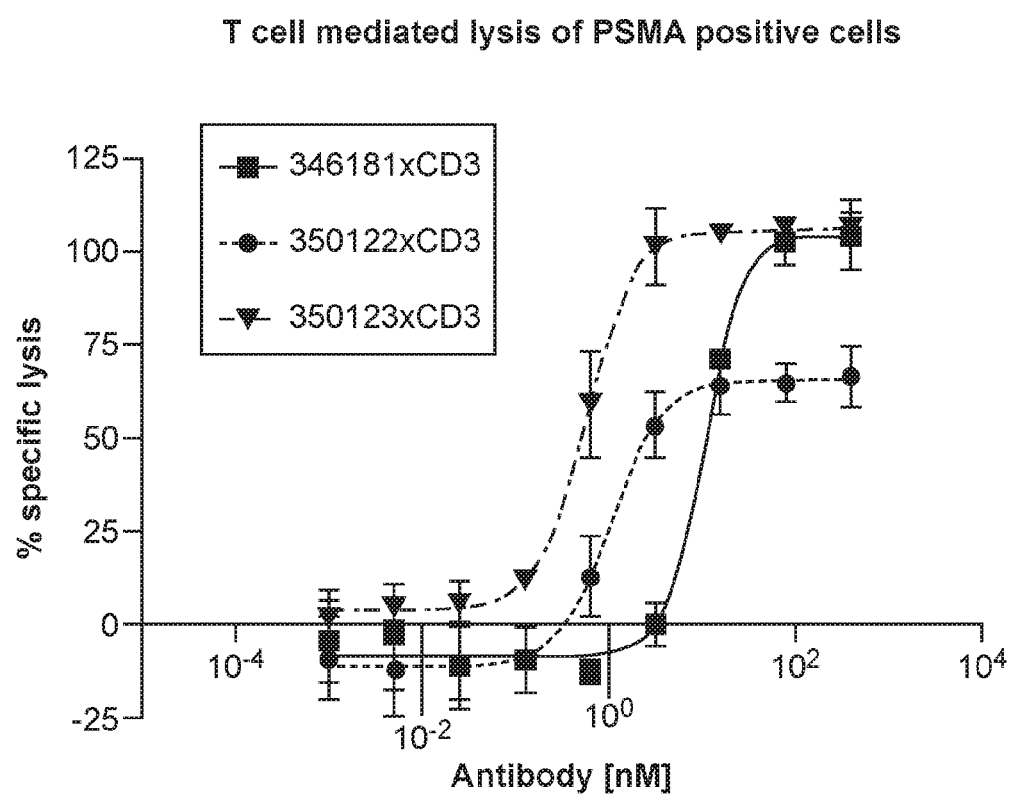
FIG. 10 is a graph showing T-cell mediated lysis of PSMA positive cells.
Figure 11A:
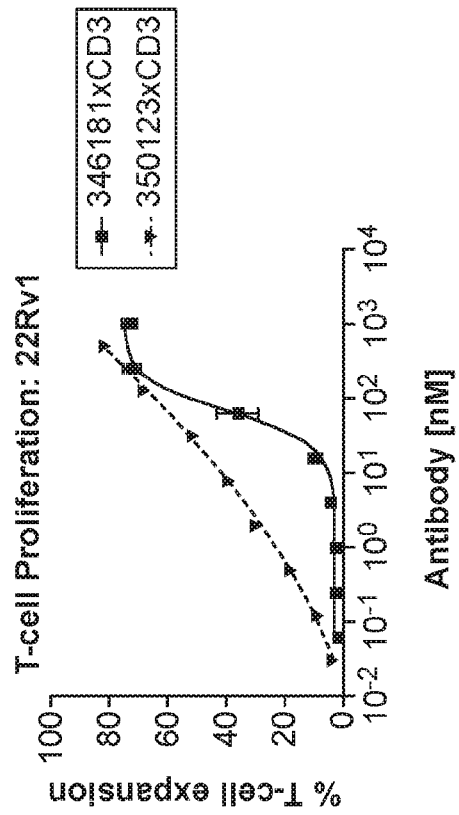
FIG. 11, panel A, is a graph depicting T-cell proliferation as a function of antibody concentration.
Figure 11B:
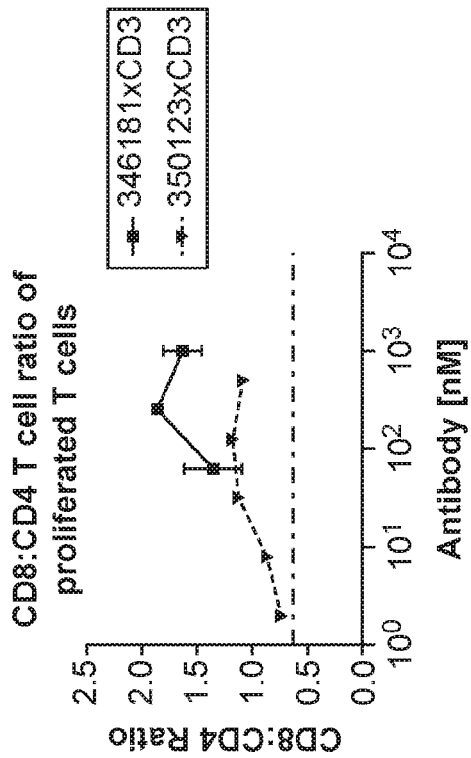
Figure 11C:
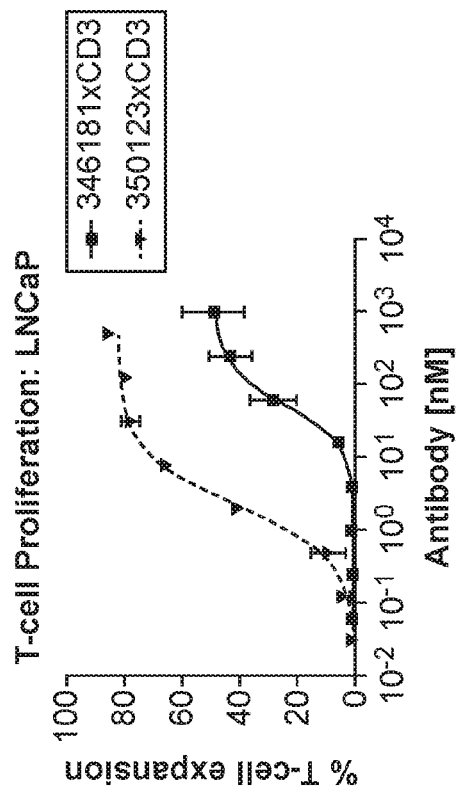
Figure 11D:
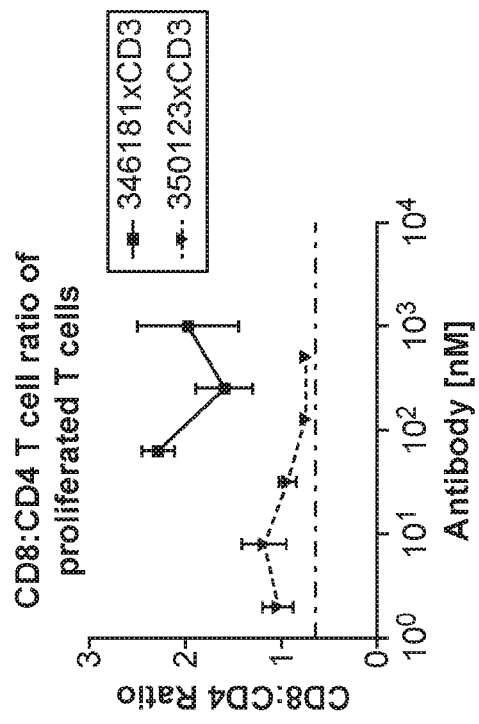

FIG. 10 depicts T-cell mediated lysis of PSMA positive cells. The data in FIG. 10 demonstrates that binding to PSMA via two different epitopes results in increased cell killing as compared to a bivalent but monospecific version of the antibody.

Example 7: A Monoparatopic PSMAxCD3 Bispecific Antibody Induces Less Cytokine Production than a Biparatopic PSMAxCD3 Multi-Specific Antibody Cytokine production was analyzed in tumor cytotoxicity assays with resting T-cells. The design of these assays is detailed elsewhere. Supernatants were collected upon completion of the assays (after 72 hours of incubation for assays using 22Rv1 cells, 48 hours for all other cell lines). ELISA kits were used for detection of IL-2 (Biolegend 431804) and IFNγ (Biolegend 430104) according to the manufacturer's protocol. Experimental supernatants were diluted before analysis in the ELISAs such that the levels of cytokines would fall within the linear portion of the standard curve supplied with each kit. In some cases, no cytokines could be detected in the experiment wells, and values were reported as less than or equal to the lower limit of quantification for the assay.

Figure 12B:
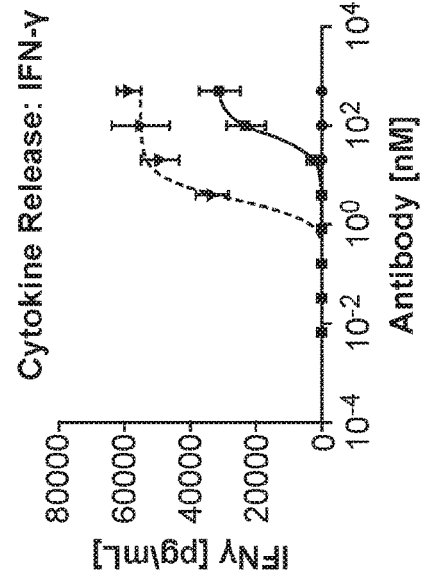
FIG. 12, panel A, is a graph depicting T-cell mediated lysis of PSMA positive cells as a function of antibody concentration.
Figure 12A:
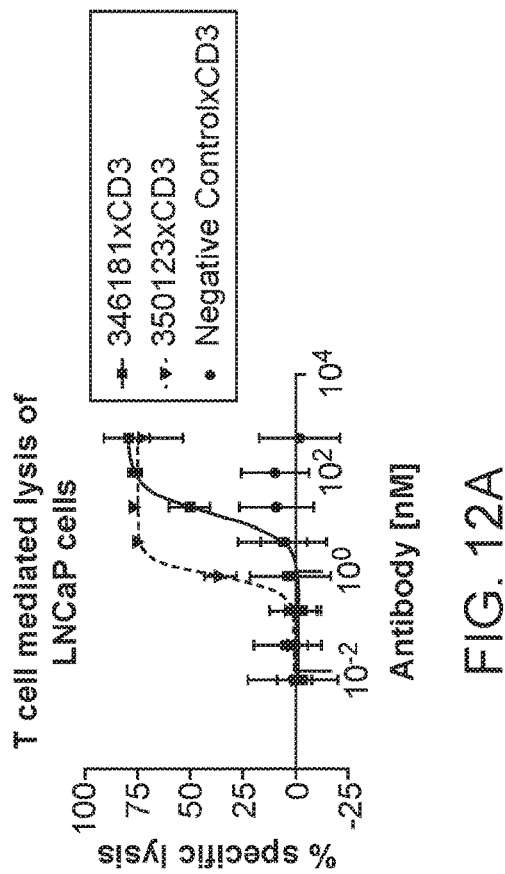
Figure 12C:
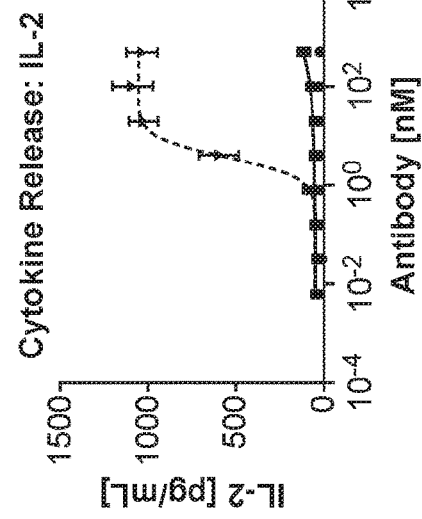

FIG. 12, panels A-C, show T-cell mediated lysis of PSMA positive cells and comparison with cytokine production. Multispecific PSMAxCD3 antibodies induce T-cell mediated lysis of the PSMA positive prostate cancer cell line LNCaP. The biparatopic molecule (350123) stimulated more potent tumor cell killing as compared to the monoparatopic molecule (346181), but also caused production of higher levels of the cytokines interferon gamma (IFNγ) and interleukin 2 (IL-2), as exemplified by FIG. 12, panel B and panel C.

Table 10 shows T-cell mediated lysis and cytokine production against four PSMA positive prostate tumor cell lines. The PSMAxCD3 multi-specific antibodies were tested in in vitro tumor cell cytotoxicity assays using unstimulated T-cells and a dose series of antibody against a panel of four PSMA positive tumor cell lines. After 72 hours (22Rv1) or 48 hours (MDA-PCa-2b, LNCAP, PC3-PSMA) the percent of tumor cell death was calculated and reported by EC50 as well as the highest percent killing achieved. Supernatants from these experiment wells were collected and analyzed by ELISA for the cytokines interferon-gamma (IFNγ) or interleukin-2 (IL-2). The monoparatopic molecule (3461881) induced approximately equivalent levels of tumor cytotoxicity against all four cell lines tested as compared to the biparatopic molecule, but had higher EC50s for cytokine production and in most cases stimulated lower levels of maximum cytokine production.

Example 8: PSMAxCD3 Multi-Specific Antibodies Induce T-Cell Proliferation

PSMA positive tumor cells were seeded at 25,000 cells per well in a 96-well plate and grown overnight at 37° C. Human pan T-cells isolated from resting PBMCs (Miltenyi 130-096-535) were labeled with the lineage tracing dye CFSE according to manufacturer's instructions (ThermoFisher C34554). 100,000 labeled pan T-cells were then added to the wells containing the tumor cells, followed by a dilution series of antibodies, and incubated at 37° C., 8% $CO_2$. After 5 days of incubation, the cells were mixed gently and transferred to a flow cytometry plate. The cells were pelleted, and the supernatant removed, followed by staining with anti-CD8 conjugated to APC (Biolegend 301049) and anti-CD4 conjugated to PE (Biolegend 317410) for 20 minutes on ice. The cells were then washed and resuspending in flow cytometry buffer for analysis (BD FACSCelesta™) Cells were gated on forward and side scatter, and CD4 or CD8 expression. The percent of T-cells that had proliferated, as indicated by CD4 or CD8 positive staining and low or negative CFSE signal, was calculated for the entire T-cell population, as well as the CD4 and CD8 subsets. Flow cytometry data was analyzed using FlowJo™ and plotted in GraphPad Prism 7.

FIG. 11, panels A-D, show that PSMAxCD3 multi-specific antibodies stimulated T-cell proliferation in the presence of PSMA positive tumor cells, and that monoparatopic PSMA bispecific antibodies preferentially activate CD3 T-cells. Multi-specific antibodies were incubated together with PSMA expressing tumor cells and T-cells labeled with the lineage tracing dye CFSE. After 5 days of incubation, T-cell proliferation and the composition of proliferated T-cells (CD8+ versus CD4+) were analyzed by flow cytometry. Panels A and B show total T-cell proliferation, while panels C and D indicate the ratio of CD8+ to CD4+ T-cells in the proliferated wells. A dashed horizontal line indicates that CD8:CD4 ratio of the unstimulated T-cells and is approximately 1:2 (actual value=0.64). The monoparatopic PSMAxCD3 bispecific antibody (346181) preferentially activates CD8 T-cells (CD8:CD4 ratio after expansion of approximately 2:1) whereas the biparatopic PSMAxCD3 multi-specific antibody (350123) less preferentially activates CD8+ T-cells (CD8:CD4 ratio of about 1:1).

Example 9: A Multi-Specific Antibody Causes Suppression of Prostate Tumor Growth in a Xenograft Model 5-6 week old male immune-deficient CIEA-NOG Mice® (Taconic) were implanted with 10 million 22Rv1 cells

TABLE 10

T-cell mediated lysis and cytokine production against four PSMA positive prostate tumor cell lines.

| Cell line | Antibody | Cell binding EC50 (nM) | Max Cytotoxicity (% lysis) | Kill EC50 (nM) | Max IFNγ (pg/mL) | IFNγ EC50 (nM) | Max IL-2 (pg/ml) | IL-2 EC50 (nM) |
|---|---|---|---|---|---|---|---|---|
| 22Rv1 | 346181xCD3 | 58 | 45 | 52.8 | 21,150 | 173.8 | ≤LLOQ | NA |
|  | 350123xCD3 | 3 | 53 | 0.42 | 73,031 | 380.2 | ≤LLOQ | NA |
| MDA-PCa-2b | 346181xCD3 | 28 | 26 | 23.6 | 14,309 | 116.5 | 524 | 38.5 |
|  | 350123xCD3 | 2 | 29 | 0.41 | 12,026 | 0.90 | 1111 | 1.11 |
| LNCAP | 346181xCD3 | 17 | 79 | 14.6 | 32,237 | 63.0 | 183 | 575 |
|  | 350123xCD3 | 2 | 75 | 0.84 | 60,397 | 3.29 | 1057 | 3.73 |
| PC3-PSMA | 346181xCD3 | 30 | 42 | 3.7 | 7,340 | 10.1 | 1569 | 4.1 |
|  | 350123xCD3 | 6 | 51 | 0.40 | 10,136 | 1.01 | 3480 | 1.1 | subcutaneously into their lower right flanks, followed by addition of 10 million human PBMCs via tail vein injection one day following tumor implantation. The animals received treatment with 100 µg of multi-specific antibody or vehicle by tail vein injection starting one day after tumor implantation on days 1, 5, 9 and 13. Tumor volume was quantified using calipers and was recorded for 25 days.

Figure 13:
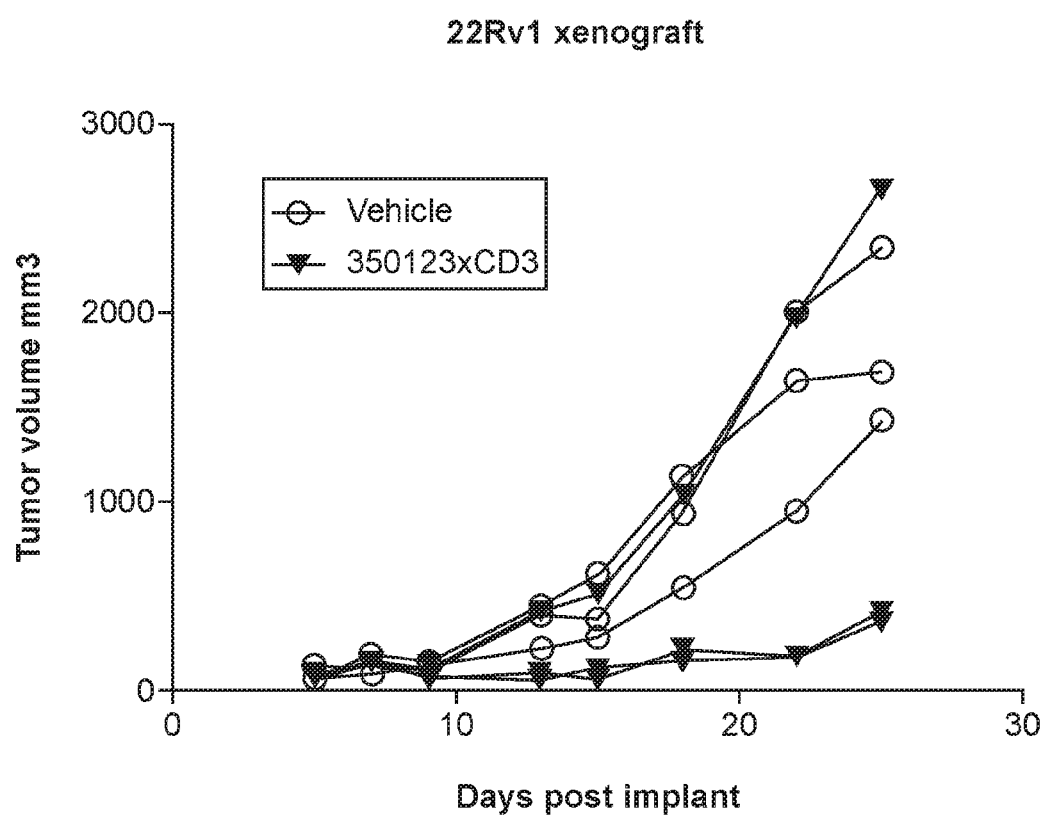
FIG. 13 is a graph depicting inhibition of 22Rv1 tumor growth in a tumor xenograft model.

FIG. 13 shows the results of the 22Rv1 tumor xenograft model. The biparatopic PSMAxCD3 molecule (350123) showed inhibition of 22Rv1 tumor growth in a tumor xenograft model. Three mice were tested for each treatment group, and the change in tumor volume for each animal was plotted in millimeters cubed. Animals received PBMCs on day 1 post tumor implantation and were treated with antibody on days 1, 5, 9, and 13. Two out of the three animals treated with multispecific antibody showed delay in tumor progression.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. An antigen-binding region of an anti-PSMA heavy chain antibody, comprising a CDR1 sequence of SEQ ID NO: 2, a CDR2 sequence of SEQ ID NO: 11, and a CDR3 sequence of SEQ ID NO: 18.

2. The antigen-binding region according to claim 1, comprising a CDR1 sequence of SEQ ID NO: 2, a CDR2 sequence of SEQ ID NO: 11, and a CDR3 sequence of SEQ ID NO: 18 in a human VH framework.

3. The antigen-binding region according to claim 1, comprising a CDR1 sequence of SEQ ID NO: 2, a CDR2 sequence of SEQ ID NO: 11, and a CDR3 sequence of SEQ ID NO: 18 in a monovalent configuration.

4. The antigen-binding region according to claim 1, comprising a heavy chain variable region sequence of SEQ ID NO: 25.

5. An antibody comprising an antigen-binding region of an anti-PSMA heavy chain antibody, wherein the antigen-binding region comprises a CDR1 sequence of SEQ ID NO: 2, a CDR2 sequence of SEQ ID NO: 11, and a CDR3 sequence of SEQ ID NO: 18.

6. The antibody according to claim 5, wherein the antigen-binding region comprises a CDR1 sequence of SEQ ID NO: 2, a CDR2 sequence of SEQ ID NO: 11, and a CDR3 sequence of SEQ ID NO: 18 in a human VH framework.

7. The antibody according to claim 5, wherein the antigen-binding region comprises a CDR1 sequence of SEQ ID NO: 2, a CDR2 sequence of SEQ ID NO: 11, and a CDR3 sequence of SEQ ID NO: 18 in a monovalent configuration.

8. The antibody according to claim 5, wherein the antigen-binding region comprises a heavy chain variable region sequence of SEQ ID NO: 25.

9. The antibody according to claim 5, wherein the antibody is a bispecific antibody.

10. The antibody according to claim 9, wherein the antibody further binds to a CD3 protein.

11. The antibody according to claim 9, further comprising a CD3-binding heavy chain variable region that is paired with a light chain variable region.

12. The antibody according to claim 11, wherein the CD3-binding heavy chain variable region comprises a CDR1 sequence of SEQ ID NO: 59, a CDR2 sequence of SEQ ID NO: 60, and a CDR3 sequence of SEQ ID NO: 61.

13. The antibody according to claim 11, wherein the CD3-binding heavy chain variable region comprises heavy chain variable region sequence of SEQ ID NO: 65.

14. The antibody according to claim 11, wherein the light chain variable region comprises a CDR1 sequence of SEQ ID NO: 62, a CDR2 sequence of SEQ ID NO: 63, and a CDR3 sequence of SEQ ID NO: 64.

15. The antibody according to claim 11, wherein the light chain variable region comprises a light chain variable region sequence of SEQ ID NO: 66.

16. The antibody according to claim 10, wherein the antibody is a three-chain antibody-like molecule.

17. A three-chain antibody-like molecule that binds to a CD3 protein and a PSMA protein, comprising:
    a first polypeptide comprising the sequence of SEQ ID NO: 86;
    a second polypeptide comprising the sequence of SEQ ID NO: 87; and
    a third polypeptide comprising the sequence of SEQ ID NO: 88, 89, 90, 91, 92, or 93.

18. The three-chain antibody-like molecule according to claim 17, wherein the third polypeptide comprises SEQ ID NO: 88.

19. A pharmaceutical composition comprising:
    the antibody according to claim 10; and
    a pharmaceutically acceptable carrier.

20. A three-chain antibody-like molecule comprising:
    (a) a PSMA-binding heavy chain variable region comprising:
        a CDR1 sequence of the formula G G S I S S $X_1$ $X_2$ Y $X_3$ (SEQ ID NO: 67), wherein $X_1$ is S or N; $X_2$ is S or N; and $X_3$ is Y or F; and
        a CDR2 sequence of the formula $X_4$ $X_5$ $X_6$ S G $X_7$ T (SEQ ID NO: 68), wherein $X_4$ is I or V; $X_5$ is D or Y; $X_6$ is Y or D; and $X_7$ is Y or S; and
        a CDR3 sequence of SEQ ID NO: 18; and
    (b) a CD3-binding heavy chain variable region that is paired with a light chain variable region, wherein:
        the CD3-binding heavy chain variable region comprises a CDR1 sequence of SEQ ID NO: 59, a CDR2 sequence of SEQ ID NO: 60, and a CDR3 sequence of SEQ ID NO: 61; and
        the light chain variable region comprises a CDR1 sequence of SEQ ID NO: 62, a CDR2 sequence of GAS, and a CDR3 sequence of SEQ ID NO: 64.

21. The three-chain antibody-like molecule of claim 20, wherein the PSMA-binding heavy chain variable region comprises a CDR1 sequence of any one of SEQ ID NOs: 1-3, a CDR2 sequence of any one of SEQ ID NOs: 11-13, and a CDR3 sequence of SEQ ID NO: 18.

22. The three-chain antibody-like molecule of claim 20, wherein the PSMA-binding heavy chain variable region comprises:
    a CDR1 sequence of SEQ ID NO: 1, a CDR2 sequence of SEQ ID NO: 11, and a CDR3 sequence of SEQ ID NO: 18; or
    a CDR1 sequence of SEQ ID NO: 1, a CDR2 sequence of SEQ ID NO: 12, and a CDR3 sequence of SEQ ID NO: 18; or
    a CDR1 sequence of SEQ ID NO: 2, a CDR2 sequence of SEQ ID NO: 11, and a CDR3 sequence of SEQ ID NO: 18; or
    a CDR1 sequence of SEQ ID NO: 3, a CDR2 sequence of SEQ ID NO: 13, and a CDR3 sequence of SEQ ID NO: 18.

23. The three-chain antibody-like molecule of claim 20, wherein the PSMA-binding heavy chain variable region comprises a CDR1 sequence of SEQ ID NO: 2, a CDR2 sequence of SEQ ID NO: 11, and a CDR3 sequence of SEQ ID NO: 18.

24. The three-chain antibody-like molecule of claim 20, wherein the PSMA-binding heavy chain variable region comprises a heavy chain variable region sequence of any one of SEQ ID NOs: 24-28.

25. The three-chain antibody-like molecule of claim 20, wherein the PSMA-binding heavy chain variable region comprises a heavy chain variable region sequence of SEQ ID NO: 25.

26. The three-chain antibody-like molecule of claim 20, wherein the CD3-binding heavy chain variable region comprises a heavy chain variable region sequence of SEQ ID NO: 65, and the light chain variable region comprises a light chain variable region sequence of SEQ ID NO: 66.

27. The three-chain antibody-like molecule of claim 20, wherein:
    the CD3-binding heavy chain variable region comprises a heavy chain variable region sequence of SEQ ID NO: 65;
    the light chain variable region comprises a light chain variable region sequence of SEQ ID NO: 66; and
    the PSMA-binding heavy chain variable region comprises a heavy chain variable region sequence of any one of SEQ ID NOs: 24-28.

28. The three-chain antibody-like molecule of claim 20, wherein:
    the CD3-binding heavy chain variable region comprises a heavy chain variable region sequence of SEQ ID NO: 65;
    the light chain variable region comprises a light chain variable region sequence of SEQ ID NO: 66; and
    the PSMA-binding heavy chain variable region comprises a heavy chain variable region sequence of SEQ ID NO: 25.

* * * * *

UNITED STATES PATENT AND TRADEMARK OFFICE
CERTIFICATE OF CORRECTION

| | | |
|---|---|---|
| PATENT NO. | : 12,180,298 B2 | Page 1 of 1 |
| APPLICATION NO. | : 17/601417 | |
| DATED | : December 31, 2024 | |
| INVENTOR(S) | : Wim van Schooten et al. | |

It is certified that error appears in the above-identified patent and that said Letters Patent is hereby corrected as shown below:

In the Claims

In Claim 13 at Column 145, Line 23, replace "comprises heavy chain" with --comprises a heavy chain--.

Signed and Sealed this
Twenty-second Day of April, 2025

Coke Morgan Stewart
*Acting Director of the United States Patent and Trademark Office*

```
                        SEQUENCE LISTING

<160> NUMBER OF SEQ ID NOS: 95

<210> SEQ ID NO 1
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Gly Gly Ser Ile Ser Ser Ser Ser Tyr Tyr
1               5                   10

<210> SEQ ID NO 2
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Gly Gly Ser Ile Ser Ser Ser Asn Tyr Phe
1               5                   10

<210> SEQ ID NO 3
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Gly Gly Ser Ile Ser Ser Asn Ser Tyr Tyr
1               5                   10

<210> SEQ ID NO 4
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Gly Phe Ser Phe Arg Ser Tyr Gly
```

```
<210> SEQ ID NO 5
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Gly Phe Ser Phe Ser Ser Tyr Gly
1               5

<210> SEQ ID NO 6
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Gly Phe Ile Phe Arg Ser Tyr Gly
1               5

<210> SEQ ID NO 7
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Gly Phe Ser Phe Ser Arg Tyr Gly
1               5

<210> SEQ ID NO 8
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Gly Phe Ser Phe Thr Ser Tyr Gly
1               5

<210> SEQ ID NO 9
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Gly Phe Thr Phe Ile Ser Tyr Gly
1               5

<210> SEQ ID NO 10
```

```
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Gly Phe Thr Phe Ser Ser Tyr Gly
1               5

<210> SEQ ID NO 11
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Ile Asp Tyr Ser Gly Tyr Thr
1               5

<210> SEQ ID NO 12
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Val Asp Tyr Ser Gly Tyr Thr
1               5

<210> SEQ ID NO 13
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Ile Tyr Asp Ser Gly Ser Thr
1               5

<210> SEQ ID NO 14
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Ile Trp Tyr Asp Gly Ser Asn Lys
1               5

<210> SEQ ID NO 15
<211> LENGTH: 8
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 15

Ile Trp Tyr Asp Gly Ser Asn Arg
1               5

<210> SEQ ID NO 16
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Ile Ser Tyr Asp Gly Ser Asn Lys
1               5

<210> SEQ ID NO 17
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Ile Ser Tyr Asp Gly Ser Asn Arg
1               5

<210> SEQ ID NO 18
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Ala Arg His Lys Ala Ala Thr Ala Asp Phe Asp Tyr
1               5                   10

<210> SEQ ID NO 19
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Ala Arg Glu Pro Arg Ile Gly Tyr Tyr Tyr Glu Ser Ser Gly Tyr Asp
1               5                   10                  15

Ser Leu Asp Tyr
            20

<210> SEQ ID NO 20
<211> LENGTH: 20
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic peptide"

<400> SEQUENCE: 20

Ala Arg Glu Pro Arg Ile Gly Tyr Tyr Tyr Glu Ser Ser Gly Tyr Tyr
1               5                   10                  15

Ser Leu Asp Tyr
            20

<210> SEQ ID NO 21
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Ala Arg Glu Pro Arg Ile Gly Tyr Tyr Tyr Asp Ser Ser Gly Tyr Asp
1               5                   10                  15

Ser Leu Asp Tyr
            20

<210> SEQ ID NO 22
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Ala Arg Glu Pro Arg Ile Gly Tyr Tyr Tyr Asp Ser Ser Gly Tyr Tyr
1               5                   10                  15

Ser Leu Asp Tyr
            20

<210> SEQ ID NO 23
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Ala Arg Glu Pro Arg Val Gly Tyr Tyr Tyr Glu Thr Ser Gly Tyr Tyr
1               5                   10                  15

Ser Leu Asp Tyr
            20

<210> SEQ ID NO 24
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Gln Leu Gln Leu Gln Glu Ser Gly Pro Gly Leu Val Lys Pro Ser Glu
1               5                   10                  15

```
Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
            35                  40                  45

Trp Ile Gly Ser Ile Asp Tyr Ser Gly Tyr Thr Tyr Tyr Asn Pro Ser
 50                  55                  60

Leu Gln Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Asn
            85                  90                  95

Cys Ala Arg His Lys Ala Ala Thr Ala Asp Phe Asp Tyr Arg Gly Gln
            100                 105                 110

Gly Thr Leu Val Thr Val Ser Ser
            115                 120

<210> SEQ ID NO 25
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Gln Leu Gln Leu Gln Glu Ser Gly Pro Gly Leu Val Lys Pro Ser Glu
 1               5                   10                  15

Thr Leu Ser Leu Thr Cys Thr Val Ser Gly Gly Ser Ile Ser Ser Ser
            20                  25                  30

Asn Tyr Phe Trp Gly Trp Ile Arg Gln Ser Pro Gly Lys Gly Leu Glu
            35                  40                  45

Trp Ile Gly Ser Ile Asp Tyr Ser Gly Tyr Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Asn
            85                  90                  95

Cys Ala Arg His Lys Ala Ala Thr Ala Asp Phe Asp Tyr Arg Gly Gln
            100                 105                 110

Gly Thr Leu Val Thr Val Ser Ser
            115                 120

<210> SEQ ID NO 26
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Gln Leu Gln Leu Gln Glu Ser Gly Pro Gly Leu Val Lys Pro Ser Glu
 1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
            35                  40                  45
```

```
Trp Ile Gly Ser Val Asp Tyr Ser Gly Tyr Thr Tyr Tyr Asn Pro Ser
    50                  55                  60

Leu Gln Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Asn
                85                  90                  95

Cys Ala Arg His Lys Ala Ala Thr Ala Asp Phe Asp Tyr Arg Gly Gln
            100                 105                 110

Gly Thr Leu Val Thr Val Ser Ser
            115                 120
```

<210> SEQ ID NO 27
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 27

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
                20                  25                  30

Ser Tyr Tyr Trp Gly Trp Ile Arg Gln Pro Pro Gly Lys Gly Leu Glu
            35                  40                  45

Trp Ile Gly Ser Ile Asp Tyr Ser Gly Tyr Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Asn
                85                  90                  95

Cys Ala Arg His Lys Ala Ala Thr Ala Asp Phe Asp Tyr Arg Gly Gln
            100                 105                 110

Gly Thr Leu Val Thr Val Ser Ser
            115                 120
```

<210> SEQ ID NO 28
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 28

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Asn
                20                  25                  30

Ser Tyr Tyr Trp Gly Trp Ile Arg Gln Ser Pro Gly Lys Gly Leu Glu
            35                  40                  45

Trp Leu Gly Ser Ile Tyr Asp Ser Gly Ser Thr His Tyr Asn Pro Ser
    50                  55                  60

Leu Lys Ser Arg Val Ile Ile Ser Gly Asp Thr Ser Lys Asn Gln Phe
65                  70                  75                  80

Ser Leu Lys Leu Ser Ser Val Thr Ala Ala Asp Thr Ala Val Tyr Tyr
```

```
                85                  90                  95
Cys Ala Arg His Lys Ala Ala Thr Ala Asp Phe Asp Tyr Arg Gly Gln
            100                 105                 110
Gly Thr Leu Val Thr Val Ser Ser
        115                 120

<210> SEQ ID NO 29
<211> LENGTH: 127
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Arg Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Tyr Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Pro Arg Ile Gly Tyr Tyr Tyr Glu Ser Ser Gly Tyr Asp
            100                 105                 110

Ser Leu Asp Tyr Arg Gly Gln Gly Thr Leu Val Thr Val Ser Ser
        115                 120                 125

<210> SEQ ID NO 30
<211> LENGTH: 127
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Tyr Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Pro Arg Ile Gly Tyr Tyr Tyr Glu Ser Ser Gly Tyr Asp
            100                 105                 110

Ser Leu Asp Tyr Arg Gly Gln Gly Thr Leu Val Thr Val Ser Ser
        115                 120                 125
```

<210> SEQ ID NO 31
<211> LENGTH: 127
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Ser Tyr
            20                  25                  30

Gly Met His Trp Val Arg Gln Ala Pro Gly Lys Gly Leu Glu Gly Val
        35                  40                  45

Ala Val Ile Trp Tyr Asp Gly Ser Asn Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Pro Arg Ile Gly Tyr Tyr Tyr Glu Ser Ser Gly Tyr Tyr
            100                 105                 110

Ser Leu Asp Tyr Arg Gly Gln Gly Thr Leu Val Thr Val Ser Ser
        115                 120                 125

<210> SEQ ID NO 32
<211> LENGTH: 127
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 32

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Arg Ser Tyr
            20                  25                  30

Gly Met His Trp Val Arg Gln Ala Pro Gly Lys Gly Pro Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Pro Arg Ile Gly Tyr Tyr Tyr Glu Ser Ser Gly Tyr Tyr
            100                 105                 110

Ser Leu Asp Tyr Arg Gly Gln Gly Thr Leu Val Thr Val Ser Ser
        115                 120                 125

<210> SEQ ID NO 33
<211> LENGTH: 127
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic polypeptide"

<400> SEQUENCE: 33

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Arg Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
        50                  55                  60

Lys Gly Arg Phe Thr Ile Ser Arg Asp Tyr Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Pro Arg Ile Gly Tyr Tyr Tyr Asp Ser Ser Gly Tyr Asp
            100                 105                 110

Ser Leu Asp Tyr Arg Gly Gln Gly Thr Leu Val Thr Val Ser Ser
        115                 120                 125

<210> SEQ ID NO 34
<211> LENGTH: 127
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 34

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Arg Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Pro Arg Ile Gly Tyr Tyr Tyr Asp Ser Ser Gly Tyr Asp
            100                 105                 110

Ser Leu Asp Tyr Arg Gly Gln Gly Thr Leu Val Thr Val Ser Ser
        115                 120                 125

<210> SEQ ID NO 35
<211> LENGTH: 127
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

Gln Val Gln Leu Val Glu Ser Gly Gly Gly Val Val Gln Pro Gly Arg
```

```
                1               5                   10                  15
Ser Leu Arg Leu Ser Cys Ala Ala Ser Gly Phe Ile Phe Arg Ser Tyr
                    20                  25                  30

Gly Met His Trp Val Arg Gln Ala Pro Gly Lys Gly Pro Glu Trp Val
            35                  40                  45

Ala Val Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                    85                  90                  95

Ala Arg Glu Pro Arg Ile Gly Tyr Tyr Tyr Asp Ser Ser Gly Tyr Asp
                100                 105                 110

Ser Leu Asp Tyr Arg Gly Gln Gly Thr Leu Val Thr Val Ser Ser
            115                 120                 125

<210> SEQ ID NO 36
<211> LENGTH: 127
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Ser Tyr
                    20                  25                  30

Gly Met His Trp Val Arg Gln Ala Pro Gly Lys Gly Leu Glu Gly Val
            35                  40                  45

Ala Val Ile Trp Tyr Asp Gly Ser Asn Arg Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                    85                  90                  95

Ala Arg Glu Pro Arg Ile Gly Tyr Tyr Tyr Asp Ser Ser Gly Tyr Tyr
                100                 105                 110

Ser Leu Asp Tyr Arg Gly Gln Gly Thr Leu Val Thr Val Ser Ser
            115                 120                 125

<210> SEQ ID NO 37
<211> LENGTH: 127
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Arg Ser Tyr
                    20                  25                  30

Gly Met His Trp Val Arg Gln Ala Pro Gly Lys Gly Leu Glu Trp Val
            35                  40                  45
```

```
Ala Val Ile Ser Tyr Asp Gly Ser Asn Lys Tyr Tyr Ala Asp Ser Val
         50                  55                  60

Lys Gly Arg Phe Thr Ile Ser Arg Asp Tyr Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Pro Arg Ile Gly Tyr Tyr Tyr Asp Ser Ser Gly Tyr Asp
                100                 105                 110

Ser Leu Asp Tyr Arg Gly Gln Gly Thr Leu Val Thr Val Ser Ser
            115                 120                 125

<210> SEQ ID NO 38
<211> LENGTH: 127
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

Gln Val Gln Leu Val Glu Ser Gly Gly Gly Val Val Gln Pro Gly Arg
 1                5                  10                  15

Ser Leu Arg Leu Ser Cys Ala Ala Ser Gly Phe Ser Phe Ser Arg Tyr
                 20                  25                  30

Gly Met His Trp Val Arg Gln Ala Pro Gly Lys Gly Leu Glu Gly Val
             35                  40                  45

Ala Val Ile Trp Tyr Asp Gly Ser Asn Arg Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Pro Arg Ile Gly Tyr Tyr Tyr Glu Ser Ser Gly Tyr Tyr
                100                 105                 110

Ser Leu Asp Tyr Arg Gly Gln Gly Thr Leu Val Thr Val Ser Ser
            115                 120                 125

<210> SEQ ID NO 39
<211> LENGTH: 127
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

Gln Val Gln Leu Val Glu Ser Gly Gly Gly Val Val Gln Pro Gly Arg
 1                5                  10                  15

Ser Leu Arg Leu Ser Cys Ala Ala Ser Gly Phe Ser Phe Ser Arg Tyr
                 20                  25                  30

Gly Met His Trp Val Arg Gln Ala Pro Gly Lys Gly Leu Glu Trp Val
             35                  40                  45

Ala Val Ile Ser Tyr Asp Gly Ser Asn Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80
```

```
Leu Gln Met Asn Ser Leu Arg Ala Glu Asp Thr Ala Val Tyr Tyr Cys
                85                  90                  95

Ala Arg Glu Pro Arg Val Gly Tyr Tyr Tyr Glu Thr Ser Gly Tyr Tyr
            100                 105                 110

Ser Leu Asp Tyr Arg Gly Gln Gly Thr Leu Val Thr Val Ser Ser
        115                 120                 125

<210> SEQ ID NO 40
<211> LENGTH: 127
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Thr Ser Tyr
            20                  25                  30

Gly Met His Trp Val Arg Gln Ala Pro Gly Lys Gly Leu Glu Gly Val
        35                  40                  45

Ala Val Ile Trp Tyr Asp Gly Ser Asn Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Pro Arg Ile Gly Tyr Tyr Tyr Glu Ser Ser Gly Tyr Tyr
            100                 105                 110

Ser Leu Asp Tyr Arg Gly Gln Gly Thr Leu Val Thr Val Ser Ser
        115                 120                 125

<210> SEQ ID NO 41
<211> LENGTH: 127
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Arg Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Pro Arg Ile Gly Tyr Tyr Tyr Glu Ser Ser Gly Tyr Tyr
            100                 105                 110

Ser Leu Asp Tyr Arg Gly Gln Gly Thr Leu Val Thr Val Ser Ser
```

<210> SEQ ID NO 42
<211> LENGTH: 127
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 42

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Arg Tyr
            20                  25                  30

Gly Met His Trp Val Arg Gln Ala Pro Gly Lys Gly Leu Glu Gly Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Pro Arg Ile Gly Tyr Tyr Tyr Glu Ser Ser Gly Tyr Tyr
            100                 105                 110

Ser Leu Asp Tyr Arg Gly Gln Gly Thr Leu Val Thr Val Ser Ser
        115                 120                 125

<210> SEQ ID NO 43
<211> LENGTH: 127
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 43

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Ser Tyr
            20                  25                  30

Gly Met His Trp Val Arg Gln Ala Pro Gly Lys Gly Leu Glu Gly Val
        35                  40                  45

Ala Val Ile Trp Tyr Asp Gly Ser Asn Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Arg Glu Pro Arg Ile Gly Tyr Tyr Tyr Glu Ser Ser Gly Tyr Tyr
            100                 105                 110

Ser Leu Asp Tyr Arg Gly Gln Gly Thr Leu Val Thr Val Ser Ser
        115                 120                 125

<210> SEQ ID NO 44
<211> LENGTH: 127
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic polypeptide"

<400> SEQUENCE: 44
```

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Ser Phe Ser Ser Tyr
            20                  25                  30

Gly Met His Trp Val Arg Gln Ala Pro Gly Lys Gly Leu Glu Gly Val
        35                  40                  45

Ala Val Ile Trp Tyr Asp Gly Ser Asn Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Pro Arg Ile Gly Tyr Tyr Tyr Glu Ser Ser Gly Tyr Tyr
            100                 105                 110

Ser Leu Asp Tyr Arg Gly Gln Gly Thr Leu Val Thr Val Ser Ser
        115                 120                 125

```
<210> SEQ ID NO 45
<211> LENGTH: 127
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 45
```

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Ser Tyr
            20                  25                  30

Gly Met His Trp Val Arg Gln Ala Pro Gly Lys Gly Leu Glu Gly Val
        35                  40                  45

Ala Val Ile Trp Tyr Asp Gly Ser Asn Arg Tyr Tyr Ala Asp Ser Val
    50                  55                  60

Lys Gly Arg Phe Thr Ile Ser Arg Asp Ser Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Pro Arg Ile Gly Tyr Tyr Tyr Glu Ser Ser Gly Tyr Tyr
            100                 105                 110

Ser Leu Asp Tyr Arg Gly Gln Gly Thr Leu Val Thr Val Ser Ser
        115                 120                 125

```
<210> SEQ ID NO 46
<211> LENGTH: 127
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46
```

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Arg Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Met Tyr
65                  70                  75                  80

Leu Gln Met Asn Ser Leu Arg Ala Glu Asp Thr Ala Val Tyr Tyr Cys
                85                  90                  95

Ala Arg Glu Pro Arg Ile Gly Tyr Tyr Tyr Glu Ser Ser Gly Tyr Tyr
            100                 105                 110

Ser Leu Asp Tyr Arg Gly Gln Gly Thr Leu Val Thr Val Ser Ser
            115                 120                 125
```

<210> SEQ ID NO 47
<211> LENGTH: 127
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 47

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Arg Ser Tyr
            20                  25                  30

Gly Met His Trp Val Arg Gln Ala Pro Gly Lys Gly Pro Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Pro Arg Ile Gly Tyr Tyr Tyr Glu Ser Ser Gly Tyr Tyr
            100                 105                 110

Ser Leu Asp Tyr Arg Gly Gln Gly Thr Leu Val Thr Val Ser Ser
            115                 120                 125
```

<210> SEQ ID NO 48
<211> LENGTH: 127
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 48

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Ser Tyr
            20                  25                  30

Gly Met His Trp Val Arg Gln Ala Pro Gly Lys Gly Leu Glu Gly Val
```

```
                    35                  40                  45
Ala Val Ile Trp Tyr Asp Gly Ser Asn Arg Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Glu Pro Arg Ile Gly Tyr Tyr Tyr Glu Ser Ser Gly Tyr Tyr
                100                 105                 110
Ser Leu Asp Tyr Arg Gly Gln Gly Thr Leu Val Thr Val Ser Ser
            115                 120                 125

<210> SEQ ID NO 49
<211> LENGTH: 127
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 49

Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Ile Ser Tyr
            20                  25                  30
Gly Met His Trp Val Arg Gln Ala Pro Gly Lys Gly Leu Glu Gly Val
            35                  40                  45
Ala Val Ile Trp Tyr Asp Gly Ser Asn Arg Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Glu Pro Arg Ile Gly Tyr Tyr Tyr Glu Ser Ser Gly Tyr Tyr
                100                 105                 110
Ser Leu Asp Tyr Arg Gly Gln Gly Thr Leu Val Thr Val Ser Ser
            115                 120                 125

<210> SEQ ID NO 50
<211> LENGTH: 127
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

Gln Val Gln Leu Val Glu Ser Gly Gly Gly Val Val Gln Pro Gly Arg
1               5                   10                  15
Ser Leu Arg Leu Ser Cys Ala Ala Ser Gly Phe Ser Phe Ser Ser Tyr
            20                  25                  30
Gly Met His Trp Val Arg Gln Ala Pro Gly Lys Gly Pro Glu Trp Val
            35                  40                  45
Ala Val Ile Trp Tyr Asp Gly Ser Asn Arg Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Arg Glu Pro Arg Ile Gly Tyr Tyr Tyr Glu Ser Gly Tyr Tyr
            100                 105                 110

Ser Leu Asp Tyr Arg Gly Gln Gly Thr Leu Val Thr Val Ser Ser
        115                 120                 125
```

<210> SEQ ID NO 51
<211> LENGTH: 127
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 51

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Pro Arg Ile Gly Tyr Tyr Tyr Glu Ser Gly Tyr Tyr
            100                 105                 110

Ser Leu Asp Tyr Arg Gly Gln Gly Thr Leu Val Thr Val Ser Ser
        115                 120                 125
```

<210> SEQ ID NO 52
<211> LENGTH: 127
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 52

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Arg Tyr
            20                  25                  30

Gly Met His Trp Val Arg Gln Ala Pro Gly Lys Gly Leu Glu Gly Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Tyr Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Pro Arg Ile Gly Tyr Tyr Tyr Asp Ser Ser Gly Tyr Asp
            100                 105                 110
```

-continued

Ser Leu Asp Tyr Arg Gly Gln Gly Thr Leu Val Thr Val Ser Ser
        115                 120                 125

<210> SEQ ID NO 53
<211> LENGTH: 127
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 53

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Gly Met His Trp Val Arg Gln Ala Pro Gly Lys Gly Leu Glu Gly Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Met Tyr
65                  70                  75                  80

Leu Gln Met Asn Ser Leu Arg Ala Glu Asp Thr Ala Val Tyr Tyr Cys
                85                  90                  95

Ala Arg Glu Pro Arg Ile Gly Tyr Tyr Tyr Glu Ser Ser Gly Tyr Tyr
            100                 105                 110

Ser Leu Asp Tyr Arg Gly Gln Gly Thr Leu Val Thr Val Ser Ser
        115                 120                 125

<210> SEQ ID NO 54
<211> LENGTH: 127
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 54

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Gly Val
        35                  40                  45

Ala Val Ile Trp Tyr Asp Gly Ser Asn Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Pro Arg Ile Gly Tyr Tyr Tyr Glu Ser Ser Gly Tyr Tyr
            100                 105                 110

Ser Leu Asp Tyr Arg Gly Gln Gly Thr Leu Val Thr Val Ser Ser
        115                 120                 125

<210> SEQ ID NO 55
<211> LENGTH: 127
<212> TYPE: PRT

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 55

```
Gln Val Gln Leu Val Glu Ser Val Gly Gly Val Val Gln Pro Gly Arg
1               5                   10                  15

Ser Leu Arg Leu Ser Cys Ala Ala Ser Gly Phe Ser Phe Ser Ser Tyr
            20                  25                  30

Gly Met His Trp Val Arg Gln Ala Pro Gly Lys Gly Leu Glu Gly Val
        35                  40                  45

Ala Val Ile Trp Tyr Asp Gly Ser Asn Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Pro Arg Ile Gly Tyr Tyr Tyr Glu Ser Ser Gly Tyr Tyr
            100                 105                 110

Ser Leu Asp Tyr Arg Gly Gln Gly Thr Leu Val Thr Val Ser Ser
        115                 120                 125
```

<210> SEQ ID NO 56
<211> LENGTH: 127
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 56

```
Gln Val Gln Leu Val Glu Ser Gly Gly Val Val Gln Pro Gly Arg
1               5                   10                  15

Ser Leu Arg Leu Ser Cys Ala Ala Ser Gly Phe Ser Phe Ser Ser Tyr
            20                  25                  30

Gly Met His Trp Val Arg Gln Ala Pro Gly Lys Gly Leu Glu Gly Val
        35                  40                  45

Ala Val Ile Ser Tyr Asp Gly Ser Asn Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Pro Arg Ile Gly Tyr Tyr Tyr Glu Ser Ser Gly Tyr Tyr
            100                 105                 110

Ser Leu Asp Tyr Arg Gly Gln Gly Thr Leu Val Thr Val Ser Ser
        115                 120                 125
```

<210> SEQ ID NO 57
<211> LENGTH: 127
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 57

Gln Val Gln Leu Val Glu Ser Gly Gly Val Val Gln Pro Gly Arg
1               5                   10                  15

Ser Leu Arg Leu Ser Cys Ala Ala Ser Gly Phe Ser Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Met Tyr
65                  70                  75                  80

Leu Gln Met Asn Ser Leu Arg Ala Glu Asp Thr Ala Val Tyr Tyr Cys
                85                  90                  95

Ala Arg Glu Pro Arg Ile Gly Tyr Tyr Tyr Glu Ser Ser Gly Tyr Tyr
                100                 105                 110

Ser Leu Asp Tyr Arg Gly Gln Gly Thr Leu Val Thr Val Ser Ser
            115                 120                 125

<210> SEQ ID NO 58
<211> LENGTH: 127
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 58

Gln Val Gln Leu Val Glu Ser Gly Gly Val Val Gln Pro Gly Arg
1               5                   10                  15

Ser Leu Arg Leu Ser Cys Ala Ala Ser Gly Phe Ser Phe Ser Ser Tyr
            20                  25                  30

Gly Met His Trp Val Arg Gln Ala Pro Gly Lys Gly Pro Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Pro Arg Ile Gly Tyr Tyr Tyr Glu Ser Ser Gly Tyr Tyr
                100                 105                 110

Ser Leu Asp Tyr Arg Gly Gln Gly Thr Leu Val Thr Val Ser Ser
            115                 120                 125

<210> SEQ ID NO 59
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Gly Phe Thr Phe Asp Asp Tyr Ala
1               5

<210> SEQ ID NO 60
<211> LENGTH: 8

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 60

Ile Ser Trp Asn Ser Gly Ser Ile
1               5

<210> SEQ ID NO 61
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Ala Lys Asp Ser Arg Gly Tyr Gly Asp Tyr Arg Leu Gly Gly Ala Tyr
1               5                   10                  15

<210> SEQ ID NO 62
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

Gln Ser Val Ser Ser Asn
1               5

<210> SEQ ID NO 63
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Gly Ala Ser
1

<210> SEQ ID NO 64
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 64

Gln Gln Tyr Asn Asn Trp Pro Trp Thr
1               5

<210> SEQ ID NO 65
<211> LENGTH: 123
<212> TYPE: PRT
<213> ORGANISM: Artificial Sequence
<220> FEATURE:
<221> NAME/KEY: source
```

<223> OTHER INFORMATION: /note="Description of Artificial Sequence:
    Synthetic polypeptide"

<400> SEQUENCE: 65

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ser Arg Gly Tyr Gly Asp Tyr Arg Leu Gly Gly Ala Tyr
            100                 105                 110

Trp Gly Gln Gly Thr Leu Val Thr Val Ser Ser
        115                 120

<210> SEQ ID NO 66
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 66

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Trp
                85                  90                  95

Thr Phe Gly Gln Gly Thr Lys Val Glu Ile Lys
            100                 105

<210> SEQ ID NO 67
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"
<220> FEATURE:
<221> NAME/KEY: VARIANT
<222> LOCATION: (7)..(7)
<223> OTHER INFORMATION: /replace="Asn"
<220> FEATURE:
<221> NAME/KEY: VARIANT
<222> LOCATION: (8)..(8)
<223> OTHER INFORMATION: /replace="Asn"

```
<220> FEATURE:
<221> NAME/KEY: VARIANT
<222> LOCATION: (10)..(10)
<223> OTHER INFORMATION: /replace="Phe"
<220> FEATURE:
<221> NAME/KEY: SITE
<222> LOCATION: (1)..(10)
<223> OTHER INFORMATION: /note="Variant residues given in the sequence
      have no preference with respect to those in the annotations
      for variant positions"

<400> SEQUENCE: 67

Gly Gly Ser Ile Ser Ser Ser Ser Tyr Tyr
1               5                   10

<210> SEQ ID NO 68
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Val"
<220> FEATURE:
<221> NAME/KEY: VARIANT
<222> LOCATION: (2)..(2)
<223> OTHER INFORMATION: /replace="Tyr"
<220> FEATURE:
<221> NAME/KEY: VARIANT
<222> LOCATION: (3)..(3)
<223> OTHER INFORMATION: /replace="Asp"
<220> FEATURE:
<221> NAME/KEY: VARIANT
<222> LOCATION: (6)..(6)
<223> OTHER INFORMATION: /replace="Ser"
<220> FEATURE:
<221> NAME/KEY: SITE
<222> LOCATION: (1)..(7)
<223> OTHER INFORMATION: /note="Variant residues given in the sequence
      have no preference with respect to those in the annotations
      for variant positions"

<400> SEQUENCE: 68

Ile Asp Tyr Ser Gly Tyr Thr
1               5

<210> SEQ ID NO 69
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 69

Ala Arg His Lys Ala Ala Thr Ala Asp Phe Asp Tyr
1               5                   10

<210> SEQ ID NO 70
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
```

```
<222> LOCATION: (3)..(3)
<223> OTHER INFORMATION: /replace="Ile" or "Thr"
<220> FEATURE:
<221> NAME/KEY: VARIANT
<222> LOCATION: (5)..(5)
<223> OTHER INFORMATION: /replace="Thr" or "Arg" or "Ile"
<220> FEATURE:
<221> NAME/KEY: VARIANT
<222> LOCATION: (6)..(6)
<223> OTHER INFORMATION: /replace="Ser"
<220> FEATURE:
<221> NAME/KEY: SITE
<222> LOCATION: (1)..(8)
<223> OTHER INFORMATION: /note="Variant residues given in the sequence
      have no preference with respect to those in the annotations
      for variant positions"

<400> SEQUENCE: 70

Gly Phe Ser Phe Ser Arg Tyr Gly
1               5

<210> SEQ ID NO 71
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (2)..(2)
<223> OTHER INFORMATION: /replace="Ser"
<220> FEATURE:
<221> NAME/KEY: VARIANT
<222> LOCATION: (8)..(8)
<223> OTHER INFORMATION: /replace="Lys"
<220> FEATURE:
<221> NAME/KEY: SITE
<222> LOCATION: (1)..(8)
<223> OTHER INFORMATION: /note="Variant residues given in the sequence
      have no preference with respect to those in the annotations
      for variant positions"

<400> SEQUENCE: 71

Ile Trp Tyr Asp Gly Ser Asn Arg
1               5

<210> SEQ ID NO 72
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (6)..(6)
<223> OTHER INFORMATION: /replace="Val"
<220> FEATURE:
<221> NAME/KEY: VARIANT
<222> LOCATION: (11)..(11)
<223> OTHER INFORMATION: /replace="Asp"
<220> FEATURE:
<221> NAME/KEY: VARIANT
<222> LOCATION: (12)..(12)
<223> OTHER INFORMATION: /replace="Thr"
<220> FEATURE:
<221> NAME/KEY: VARIANT
<222> LOCATION: (16)..(16)
<223> OTHER INFORMATION: /replace="Asp"
<220> FEATURE:
<221> NAME/KEY: SITE
<222> LOCATION: (1)..(20)
```

<223> OTHER INFORMATION: /note="Variant residues given in the sequence
      have no preference with respect to those in the annotations
      for variant positions"

<400> SEQUENCE: 72

Ala Arg Glu Pro Arg Ile Gly Tyr Tyr Glu Ser Ser Gly Tyr Tyr
1               5                   10                  15

Ser Leu Asp Tyr
            20

<210> SEQ ID NO 73
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 73

Gly Gly Gly Gly Ser
1               5

<210> SEQ ID NO 74
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 74

Gly Gly Gly Gly Ser Gly Gly Gly Gly Ser
1               5                   10

<210> SEQ ID NO 75
<211> LENGTH: 330
<212> TYPE: PRT
<213> ORGANISM: Homo sapiens

<400> SEQUENCE: 75

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

```
Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 76
<211> LENGTH: 327
<212> TYPE: PRT
<213> ORGANISM: Homo sapiens

<400> SEQUENCE: 76

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
```

```
                195                 200                 205
Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 77
<211> LENGTH: 330
<212> TYPE: PRT
<213> ORGANISM: Homo sapiens

<400> SEQUENCE: 77

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240
```

-continued

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 78
<211> LENGTH: 327
<212> TYPE: PRT
<213> ORGANISM: Homo sapiens

<400> SEQUENCE: 78

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Ala Ala Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

```
Arg Leu Thr Val Asp Lys Ser Arg Trp Gln Glu Gly Asn Val Phe Ser
            290                 295                 300
Cys Ser Val Met His Glu Ala Leu His Asn His Tyr Thr Gln Lys Ser
305                 310                 315                 320
Leu Ser Leu Ser Leu Gly Lys
                325
```

<210> SEQ ID NO 79
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 79

```
Arg Thr Val Ala Ala Pro Ser Val Phe Ile Phe Pro Pro Ser Asp Glu
1               5                   10                  15
Gln Leu Lys Ser Gly Thr Ala Ser Val Val Cys Leu Leu Asn Asn Phe
            20                  25                  30
Tyr Pro Arg Glu Ala Lys Val Gln Trp Lys Val Asp Asn Ala Leu Gln
        35                  40                  45
Ser Gly Asn Ser Gln Glu Ser Val Thr Glu Gln Asp Ser Lys Asp Ser
    50                  55                  60
Thr Tyr Ser Leu Ser Ser Thr Leu Thr Leu Ser Lys Ala Asp Tyr Glu
65                  70                  75                  80
Lys His Lys Val Tyr Ala Cys Glu Val Thr His Gln Gly Leu Ser Ser
                85                  90                  95
Pro Val Thr Lys Ser Phe Asn Arg Gly Glu Cys
            100                 105
```

<210> SEQ ID NO 80
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 80

```
Glu Val Gln Leu Val Glu Ser Gly Gly Gly Leu Val Gln Pro Gly Arg
1               5                   10                  15
Ser Leu Arg Leu Ser Cys Ala Ala Ser Gly Phe Thr Phe Asp Asp Tyr
            20                  25                  30
Ala Met His Trp Val Arg Gln Ala Pro Gly Lys Gly Leu Glu Trp Val
        35                  40                  45
Ser Gly Ile Ser Trp Asn Ser Gly Ser Ile Gly Tyr Ala Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Leu Tyr Tyr Cys
                85                  90                  95
Ala Lys Asp Ser Arg Gly Tyr Gly Asp Tyr Arg Leu Gly Gly Ala Tyr
            100                 105                 110
Trp Gly Gln Gly Thr Leu Val Thr Val Ser Ser Ala Ser Thr Lys Gly
        115                 120                 125
```

```
Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 81
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 81

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
```

```
                  20                  25                  30
Ala Met His Trp Val Arg Gln Ala Pro Gly Lys Gly Leu Glu Trp Val
            35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ser Arg Gly Tyr Gly Asp Tyr Arg Leu Gly Gly Ala Tyr
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
            210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
            290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
            370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445
```

Leu Ser Pro Gly Lys
    450

<210> SEQ ID NO 82
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 82

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ser Arg Gly Tyr Gly Asp Tyr Arg Leu Gly Gly Ala Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Ser Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335
```

-continued

```
Lys Thr Ile Ser Lys Ala Lys Gly Gln Pro Arg Glu Pro Gln Val Tyr
                340                 345                 350

Thr Leu Pro Pro Ser Gln Glu Glu Met Thr Lys Asn Gln Val Ser Leu
            355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
    435                 440                 445

Gly Lys
    450

<210> SEQ ID NO 83
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 83

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ser Arg Gly Tyr Gly Asp Tyr Arg Leu Gly Gly Ala Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Ala Ala Gly Gly
```

```
                225                 230                 235                 240
Pro Ser Val Phe Leu Phe Pro Lys Pro Lys Asp Thr Leu Met Ile
                245                 250                 255

Ser Arg Thr Pro Glu Val Thr Cys Val Val Asp Val Ser Gln Glu
            260                 265                 270

Asp Pro Glu Val Gln Phe Asn Trp Tyr Val Asp Gly Val Glu Val His
            275                 280                 285

Asn Ala Lys Thr Lys Pro Arg Glu Glu Gln Phe Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Gln Glu Glu Met Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
                420                 425                 430

Glu Ala Leu His Asn His Tyr Thr Gln Lys Ser Leu Ser Leu Ser Leu
            435                 440                 445

Gly Lys
    450

<210> SEQ ID NO 84
<211> LENGTH: 229
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 84

Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125
```

```
Gln Val Tyr Thr Leu Pro Pro Ser Gln Glu Glu Met Thr Lys Asn Gln
        130                 135                 140

Val Ser Leu Ser Cys Ala Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Val Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 85
<211> LENGTH: 229
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 85

Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225
```

```
<210> SEQ ID NO 86
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 86

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 87
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 87

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
```

```
            65                  70                  75                  80
Leu Gln Met Asn Ser Leu Arg Ala Glu Asp Thr Ala Leu Tyr Tyr Cys
                    85                  90                  95

Ala Lys Asp Ser Arg Gly Tyr Gly Asp Tyr Arg Leu Gly Gly Ala Tyr
                100                 105                 110

Trp Gly Gln Gly Thr Leu Val Thr Val Ser Ser Ala Ser Thr Lys Gly
                115                 120                 125

Pro Ser Val Phe Pro Leu Ala Pro Cys Ser Arg Ser Thr Ser Glu Ser
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Lys Thr Tyr Thr Cys Asn Val
            195                 200                 205

Asp His Lys Pro Ser Asn Thr Lys Val Asp Lys Arg Val Glu Ser Lys
            210                 215                 220

Tyr Gly Pro Pro Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
                260                 265                 270

Asp Pro Glu Val Gln Phe Asn Trp Tyr Val Asp Gly Val Glu Val His
            275                 280                 285

Asn Ala Lys Thr Lys Pro Arg Glu Glu Gln Phe Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Gln Glu Glu Met Thr Lys Asn Gln Val Ser Leu
            355                 360                 365

Trp Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
                420                 425                 430

Glu Ala Leu His Asn His Tyr Thr Gln Lys Ser Leu Ser Leu Ser Leu
            435                 440                 445

Gly Lys
    450

<210> SEQ ID NO 88
<211> LENGTH: 349
<212> TYPE: PRT
<213> ORGANISM: Artificial Sequence
```

<220> FEATURE:
<221> NAME/KEY: source
<223> OTHER INFORMATION: /note="Description of Artificial Sequence: Synthetic polypeptide"

<400> SEQUENCE: 88

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Asn Tyr Phe Trp Gly Trp Ile Arg Gln Ser Pro Gly Lys Gly Leu Glu
        35                  40                  45

Trp Ile Gly Ser Ile Asp Tyr Ser Gly Tyr Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Asn
                85                  90                  95

Cys Ala Arg His Lys Ala Ala Thr Ala Asp Phe Asp Tyr Arg Gly Gln
            100                 105                 110

Gly Thr Leu Val Thr Val Ser Ser Glu Ser Lys Tyr Gly Pro Pro Cys
        115                 120                 125

Pro Pro Cys Pro Ala Pro Glu Ala Ala Gly Gly Pro Ser Val Phe Leu
    130                 135                 140

Phe Pro Pro Lys Pro Lys Asp Thr Leu Met Ile Ser Arg Thr Pro Glu
145                 150                 155                 160

Val Thr Cys Val Val Val Asp Val Ser Gln Glu Asp Pro Glu Val Gln
                165                 170                 175

Phe Asn Trp Tyr Val Asp Gly Val Glu Val His Asn Ala Lys Thr Lys
            180                 185                 190

Pro Arg Glu Glu Gln Phe Asn Ser Thr Tyr Arg Val Val Ser Val Leu
        195                 200                 205

Thr Val Leu His Gln Asp Trp Leu Asn Gly Lys Glu Tyr Lys Cys Lys
    210                 215                 220

Val Ser Asn Lys Gly Leu Pro Ser Ser Ile Glu Lys Thr Ile Ser Lys
225                 230                 235                 240

Ala Lys Gly Gln Pro Arg Glu Pro Gln Val Tyr Thr Leu Pro Pro Ser
                245                 250                 255

Gln Glu Glu Met Thr Lys Asn Gln Val Ser Leu Ser Cys Ala Val Lys
            260                 265                 270

Gly Phe Tyr Pro Ser Asp Ile Ala Val Glu Trp Glu Ser Asn Gly Gln
        275                 280                 285

Pro Glu Asn Asn Tyr Lys Thr Thr Pro Pro Val Leu Asp Ser Asp Gly
    290                 295                 300

Ser Phe Phe Leu Val Ser Arg Leu Thr Val Asp Lys Ser Arg Trp Gln
305                 310                 315                 320

Glu Gly Asn Val Phe Ser Cys Ser Val Met His Glu Ala Leu His Asn
                325                 330                 335

His Tyr Thr Gln Lys Ser Leu Ser Leu Ser Leu Gly Lys
            340                 345
```

<210> SEQ ID NO 89
<211> LENGTH: 479
<212> TYPE: PRT
<213> ORGANISM: Artificial Sequence
<220> FEATURE:

<221> NAME/KEY: source
<223> OTHER INFORMATION: /note="Description of Artificial Sequence: Synthetic polypeptide"

<400> SEQUENCE: 89

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Asn Tyr Phe Trp Gly Trp Ile Arg Gln Ser Pro Gly Lys Gly Leu Glu
        35                  40                  45

Trp Ile Gly Ser Ile Asp Tyr Ser Gly Tyr Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Asn
                85                  90                  95

Cys Ala Arg His Lys Ala Ala Thr Ala Asp Phe Asp Tyr Arg Gly Gln
            100                 105                 110

Gly Thr Leu Val Thr Val Ser Ser Gly Gly Gly Gly Ser Gly Gly Gly
        115                 120                 125

Gly Ser Gln Leu Gln Leu Gln Glu Ser Gly Pro Gly Leu Val Lys Pro
    130                 135                 140

Ser Glu Thr Leu Ser Leu Thr Cys Thr Val Ser Gly Gly Ser Ile Ser
145                 150                 155                 160

Ser Ser Asn Tyr Phe Trp Gly Trp Ile Arg Gln Ser Pro Gly Lys Gly
                165                 170                 175

Leu Glu Trp Ile Gly Ser Ile Asp Tyr Ser Gly Tyr Thr Tyr Tyr Asn
            180                 185                 190

Pro Ser Leu Lys Ser Arg Val Thr Ile Ser Val Asp Thr Ser Lys Asn
        195                 200                 205

Gln Phe Ser Leu Lys Leu Ser Ser Val Thr Ala Ala Asp Thr Ala Val
    210                 215                 220

Tyr Asn Cys Ala Arg His Lys Ala Ala Thr Ala Asp Phe Asp Tyr Arg
225                 230                 235                 240

Gly Gln Gly Thr Leu Val Thr Val Ser Ser Glu Ser Lys Tyr Gly Pro
                245                 250                 255

Pro Cys Pro Pro Cys Pro Ala Pro Glu Ala Ala Gly Gly Pro Ser Val
            260                 265                 270

Phe Leu Phe Pro Pro Lys Pro Lys Asp Thr Leu Met Ile Ser Arg Thr
        275                 280                 285

Pro Glu Val Thr Cys Val Val Val Asp Val Ser Gln Glu Asp Pro Glu
    290                 295                 300

Val Gln Phe Asn Trp Tyr Val Asp Gly Val Glu Val His Asn Ala Lys
305                 310                 315                 320

Thr Lys Pro Arg Glu Glu Gln Phe Asn Ser Thr Tyr Arg Val Val Ser
                325                 330                 335

Val Leu Thr Val Leu His Gln Asp Trp Leu Asn Gly Lys Glu Tyr Lys
            340                 345                 350

Cys Lys Val Ser Asn Lys Gly Leu Pro Ser Ser Ile Glu Lys Thr Ile
        355                 360                 365

Ser Lys Ala Lys Gly Gln Pro Arg Glu Pro Gln Val Tyr Thr Leu Pro
    370                 375                 380

Pro Ser Gln Glu Glu Met Thr Lys Asn Gln Val Ser Leu Ser Cys Ala
```

```
                385                 390                 395                 400
Val Lys Gly Phe Tyr Pro Ser Asp Ile Ala Val Glu Trp Glu Ser Asn
                    405                 410                 415

Gly Gln Pro Glu Asn Asn Tyr Lys Thr Thr Pro Pro Val Leu Asp Ser
                420                 425                 430

Asp Gly Ser Phe Phe Leu Val Ser Arg Leu Thr Val Asp Lys Ser Arg
                435                 440                 445

Trp Gln Glu Gly Asn Val Phe Ser Cys Ser Val Met His Glu Ala Leu
            450                 455                 460

His Asn His Tyr Thr Gln Lys Ser Leu Ser Leu Ser Leu Gly Lys
465                 470                 475

<210> SEQ ID NO 90
<211> LENGTH: 356
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 90

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Arg Tyr
            20                  25                  30

Gly Met His Trp Val Arg Gln Ala Pro Gly Lys Gly Leu Glu Gly Val
            35                  40                  45

Ala Val Ile Trp Tyr Asp Gly Ser Asn Arg Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Pro Arg Ile Gly Tyr Tyr Tyr Glu Ser Ser Gly Tyr Tyr
            100                 105                 110

Ser Leu Asp Tyr Arg Gly Gln Gly Thr Leu Val Thr Val Ser Ser Glu
        115                 120                 125

Ser Lys Tyr Gly Pro Pro Cys Pro Pro Cys Pro Ala Pro Glu Ala Ala
    130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

Gln Glu Asp Pro Glu Val Gln Phe Asn Trp Tyr Val Asp Gly Val Glu
            180                 185                 190

Val His Asn Ala Lys Thr Lys Pro Arg Glu Glu Gln Phe Asn Ser Thr
        195                 200                 205

Tyr Arg Val Val Ser Val Leu Thr Val Leu His Gln Asp Trp Leu Asn
    210                 215                 220

Gly Lys Glu Tyr Lys Cys Lys Val Ser Asn Lys Gly Leu Pro Ser Ser
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Gln Glu Glu Met Thr Lys Asn Gln Val
            260                 265                 270
```

```
Ser Leu Ser Cys Ala Val Lys Gly Phe Tyr Pro Ser Asp Ile Ala Val
            275                 280                 285

Glu Trp Glu Ser Asn Gly Gln Pro Glu Asn Asn Tyr Lys Thr Thr Pro
        290                 295                 300

Pro Val Leu Asp Ser Asp Gly Ser Phe Phe Leu Val Ser Arg Leu Thr
305                 310                 315                 320

Val Asp Lys Ser Arg Trp Gln Glu Gly Asn Val Phe Ser Cys Ser Val
                325                 330                 335

Met His Glu Ala Leu His Asn His Tyr Thr Gln Lys Ser Leu Ser Leu
            340                 345                 350

Ser Leu Gly Lys
        355

<210> SEQ ID NO 91
<211> LENGTH: 493
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 91

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Arg Tyr
            20                  25                  30

Gly Met His Trp Val Arg Gln Ala Pro Gly Lys Gly Leu Glu Gly Val
        35                  40                  45

Ala Val Ile Trp Tyr Asp Gly Ser Asn Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Pro Arg Ile Gly Tyr Tyr Tyr Glu Ser Ser Gly Tyr Tyr
            100                 105                 110

Ser Leu Asp Tyr Arg Gly Gln Gly Thr Leu Val Thr Val Ser Ser Gly
        115                 120                 125

Gly Gly Gly Ser Gly Gly Gly Ser Gln Val Gln Leu Val Glu Ser
    130                 135                 140

Gly Gly Gly Val Val Gln Pro Gly Arg Ser Leu Arg Leu Ser Cys Ala
145                 150                 155                 160

Ala Ser Gly Phe Ser Phe Ser Arg Tyr Gly Met His Trp Val Arg Gln
                165                 170                 175

Ala Pro Gly Lys Gly Leu Glu Gly Val Ala Val Ile Trp Tyr Asp Gly
            180                 185                 190

Ser Asn Arg Tyr Tyr Ala Asp Ser Val Lys Gly Arg Phe Thr Ile Ser
        195                 200                 205

Arg Asp Asn Ser Lys Asn Thr Leu Tyr Leu Gln Met Asn Ser Leu Arg
    210                 215                 220

Ala Glu Asp Thr Ala Val Tyr Tyr Cys Ala Arg Glu Pro Arg Ile Gly
225                 230                 235                 240

Tyr Tyr Tyr Glu Ser Ser Gly Tyr Tyr Ser Leu Asp Tyr Arg Gly Gln
                245                 250                 255
```

```
Gly Thr Leu Val Thr Val Ser Ser Glu Ser Lys Tyr Gly Pro Pro Cys
                260                 265                 270

Pro Pro Cys Pro Ala Pro Glu Ala Ala Gly Gly Pro Ser Val Phe Leu
            275                 280                 285

Phe Pro Pro Lys Pro Lys Asp Thr Leu Met Ile Ser Arg Thr Pro Glu
        290                 295                 300

Val Thr Cys Val Val Val Asp Val Ser Gln Glu Asp Pro Glu Val Gln
305                 310                 315                 320

Phe Asn Trp Tyr Val Asp Gly Val Glu Val His Asn Ala Lys Thr Lys
                325                 330                 335

Pro Arg Glu Glu Gln Phe Asn Ser Thr Tyr Arg Val Val Ser Val Leu
            340                 345                 350

Thr Val Leu His Gln Asp Trp Leu Asn Gly Lys Glu Tyr Lys Cys Lys
        355                 360                 365

Val Ser Asn Lys Gly Leu Pro Ser Ser Ile Glu Lys Thr Ile Ser Lys
370                 375                 380

Ala Lys Gly Gln Pro Arg Glu Pro Gln Val Tyr Thr Leu Pro Pro Ser
385                 390                 395                 400

Gln Glu Glu Met Thr Lys Asn Gln Val Ser Leu Ser Cys Ala Val Lys
                405                 410                 415

Gly Phe Tyr Pro Ser Asp Ile Ala Val Glu Trp Glu Ser Asn Gly Gln
            420                 425                 430

Pro Glu Asn Asn Tyr Lys Thr Thr Pro Pro Val Leu Asp Ser Asp Gly
        435                 440                 445

Ser Phe Phe Leu Val Ser Arg Leu Thr Val Asp Lys Ser Arg Trp Gln
450                 455                 460

Glu Gly Asn Val Phe Ser Cys Ser Val Met His Glu Ala Leu His Asn
465                 470                 475                 480

His Tyr Thr Gln Lys Ser Leu Ser Leu Ser Leu Gly Lys
                485                 490

<210> SEQ ID NO 92
<211> LENGTH: 486
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 92

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Asn Tyr Phe Trp Gly Trp Ile Arg Gln Ser Pro Gly Lys Gly Leu Glu
        35                  40                  45

Trp Ile Gly Ser Ile Asp Tyr Ser Gly Tyr Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Asn
                85                  90                  95

Cys Ala Arg His Lys Ala Ala Thr Ala Asp Phe Asp Tyr Arg Gly Gln
            100                 105                 110

Gly Thr Leu Val Thr Val Ser Ser Gly Gly Gly Gly Ser Gly Gly Gly
```

```
            115                 120                 125
Gly Ser Gln Val Gln Leu Val Glu Ser Gly Gly Val Val Gln Pro
130                 135                 140

Gly Arg Ser Leu Arg Leu Ser Cys Ala Ala Ser Gly Phe Ser Phe Ser
145                 150                 155                 160

Arg Tyr Gly Met His Trp Val Arg Gln Ala Pro Gly Lys Gly Leu Glu
                165                 170                 175

Gly Val Ala Val Ile Trp Tyr Asp Gly Ser Asn Arg Tyr Tyr Ala Asp
                180                 185                 190

Ser Val Lys Gly Arg Phe Thr Ile Ser Arg Asp Asn Ser Lys Asn Thr
            195                 200                 205

Leu Tyr Leu Gln Met Asn Ser Leu Arg Ala Glu Asp Thr Ala Val Tyr
210                 215                 220

Tyr Cys Ala Arg Glu Pro Arg Ile Gly Tyr Tyr Glu Ser Ser Gly
225                 230                 235                 240

Tyr Tyr Ser Leu Asp Tyr Arg Gly Gln Gly Thr Leu Val Thr Val Ser
                245                 250                 255

Ser Glu Ser Lys Tyr Gly Pro Pro Cys Pro Pro Cys Pro Ala Pro Glu
            260                 265                 270

Ala Ala Gly Gly Pro Ser Val Phe Leu Phe Pro Pro Lys Pro Lys Asp
                275                 280                 285

Thr Leu Met Ile Ser Arg Thr Pro Glu Val Thr Cys Val Val Val Asp
290                 295                 300

Val Ser Gln Glu Asp Pro Glu Val Gln Phe Asn Trp Tyr Val Asp Gly
305                 310                 315                 320

Val Glu Val His Asn Ala Lys Thr Lys Pro Arg Glu Glu Gln Phe Asn
                325                 330                 335

Ser Thr Tyr Arg Val Val Ser Val Leu Thr Val Leu His Gln Asp Trp
            340                 345                 350

Leu Asn Gly Lys Glu Tyr Lys Cys Lys Val Ser Asn Lys Gly Leu Pro
                355                 360                 365

Ser Ser Ile Glu Lys Thr Ile Ser Lys Ala Lys Gly Gln Pro Arg Glu
            370                 375                 380

Pro Gln Val Tyr Thr Leu Pro Pro Ser Gln Glu Met Thr Lys Asn
385                 390                 395                 400

Gln Val Ser Leu Ser Cys Ala Val Lys Gly Phe Tyr Pro Ser Asp Ile
                405                 410                 415

Ala Val Glu Trp Glu Ser Asn Gly Gln Pro Glu Asn Asn Tyr Lys Thr
                420                 425                 430

Thr Pro Pro Val Leu Asp Ser Asp Gly Ser Phe Phe Leu Val Ser Arg
            435                 440                 445

Leu Thr Val Asp Lys Ser Arg Trp Gln Glu Gly Asn Val Phe Ser Cys
450                 455                 460

Ser Val Met His Glu Ala Leu His Asn His Tyr Thr Gln Lys Ser Leu
465                 470                 475                 480

Ser Leu Ser Leu Gly Lys
                485

<210> SEQ ID NO 93
<211> LENGTH: 486
<212> TYPE: PRT
<213> ORGANISM: Artificial Sequence
<220> FEATURE:
<221> NAME/KEY: source
<223> OTHER INFORMATION: /note="Description of Artificial Sequence:
```

-continued

Synthetic polypeptide"

<400> SEQUENCE: 93

```
Gln Val Gln Leu Val Glu Ser Gly Gly Val Val Gln Pro Gly Arg
1               5                   10                  15

Ser Leu Arg Leu Ser Cys Ala Ala Ser Gly Phe Ser Phe Ser Arg Tyr
            20                  25                  30

Gly Met His Trp Val Arg Gln Ala Pro Gly Lys Gly Leu Glu Gly Val
        35                  40                  45

Ala Val Ile Trp Tyr Asp Gly Ser Asn Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Pro Arg Ile Gly Tyr Tyr Tyr Glu Ser Ser Gly Tyr Tyr
            100                 105                 110

Ser Leu Asp Tyr Arg Gly Gln Gly Thr Leu Val Thr Val Ser Ser Gly
        115                 120                 125

Gly Gly Gly Ser Gly Gly Gly Ser Gln Leu Gln Leu Gln Glu Ser
130                 135                 140

Gly Pro Gly Leu Val Lys Pro Ser Glu Thr Leu Ser Leu Thr Cys Thr
145                 150                 155                 160

Val Ser Gly Gly Ser Ile Ser Ser Ser Asn Tyr Phe Trp Gly Trp Ile
                165                 170                 175

Arg Gln Ser Pro Gly Lys Gly Leu Glu Trp Ile Gly Ser Ile Asp Tyr
            180                 185                 190

Ser Gly Tyr Thr Tyr Tyr Asn Pro Ser Leu Lys Ser Arg Val Thr Ile
        195                 200                 205

Ser Val Asp Thr Ser Lys Asn Gln Phe Ser Leu Lys Leu Ser Ser Val
    210                 215                 220

Thr Ala Ala Asp Thr Ala Val Tyr Asn Cys Ala Arg His Lys Ala Ala
225                 230                 235                 240

Thr Ala Asp Phe Asp Tyr Arg Gly Gln Gly Thr Leu Val Thr Val Ser
                245                 250                 255

Ser Glu Ser Lys Tyr Gly Pro Pro Cys Pro Pro Cys Pro Ala Pro Glu
            260                 265                 270

Ala Ala Gly Gly Pro Ser Val Phe Leu Phe Pro Pro Lys Pro Lys Asp
        275                 280                 285

Thr Leu Met Ile Ser Arg Thr Pro Glu Val Thr Cys Val Val Val Asp
290                 295                 300

Val Ser Gln Glu Asp Pro Glu Val Gln Phe Asn Trp Tyr Val Asp Gly
305                 310                 315                 320

Val Glu Val His Asn Ala Lys Thr Lys Pro Arg Glu Glu Gln Phe Asn
                325                 330                 335

Ser Thr Tyr Arg Val Val Ser Val Leu Thr Val Leu His Gln Asp Trp
            340                 345                 350

Leu Asn Gly Lys Glu Tyr Lys Cys Lys Val Ser Asn Lys Gly Leu Pro
        355                 360                 365

Ser Ser Ile Glu Lys Thr Ile Ser Lys Ala Lys Gly Gln Pro Arg Glu
    370                 375                 380

Pro Gln Val Tyr Thr Leu Pro Pro Ser Gln Glu Glu Met Thr Lys Asn
385                 390                 395                 400
```

```
Gln Val Ser Leu Ser Cys Ala Val Lys Gly Phe Tyr Pro Ser Asp Ile
                405                 410                 415

Ala Val Glu Trp Glu Ser Asn Gly Gln Pro Glu Asn Asn Tyr Lys Thr
            420                 425                 430

Thr Pro Pro Val Leu Asp Ser Asp Gly Ser Phe Phe Leu Val Ser Arg
        435                 440                 445

Leu Thr Val Asp Lys Ser Arg Trp Gln Glu Gly Asn Val Phe Ser Cys
    450                 455                 460

Ser Val Met His Glu Ala Leu His Asn His Tyr Thr Gln Lys Ser Leu
465                 470                 475                 480

Ser Leu Ser Leu Gly Lys
                485

<210> SEQ ID NO 94
<211> LENGTH: 50
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: SITE
<222> LOCATION: (1)..(50)
<223> OTHER INFORMATION: /note="This sequence may encompass 1-10 'Gly
      Gly Gly Gly Ser' repeating units"
<220> FEATURE:
<221> NAME/KEY: source
<223> OTHER INFORMATION: /note="See specification as filed for detailed
      description of substitutions and preferred embodiments"

<400> SEQUENCE: 94

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
                20                  25                  30

Gly Gly Ser Gly Gly Gly Gly Ser Gly Gly Gly Gly Ser Gly Gly Gly
            35                  40                  45

Gly Ser
    50

<210> SEQ ID NO 95
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Penta-His tag"

<400> SEQUENCE: 95

His His His His His
1               5
```